United States Patent
Singh et al.

(10) Patent No.: US 9,458,456 B2
(45) Date of Patent: Oct. 4, 2016

(54) METHODS AND COMPOSITIONS FOR THE DIAGNOSIS, CLASSIFICATION, AND TREATMENT OF CANCER

(75) Inventors: Ajay Pratap Singh, Mobile, AL (US); Sanjeev Srivastava, Mobile, AL (US); Seema Singh, Mobile, AL (US)

(73) Assignee: UNIVERSITY OF SOUTH ALABAMA, Mobile, AL (US)

( * ) Notice: Subject to any disclaimer, the term of this patent is extended or adjusted under 35 U.S.C. 154(b) by 7 days.

(21) Appl. No.: 14/007,938

(22) PCT Filed: Mar. 30, 2012

(86) PCT No.: PCT/US2012/031574
§ 371 (c)(1),
(2), (4) Date: Sep. 26, 2013

(87) PCT Pub. No.: WO2012/135696
PCT Pub. Date: Oct. 4, 2012

(65) Prior Publication Data
US 2014/0045920 A1    Feb. 13, 2014

Related U.S. Application Data

(60) Provisional application No. 61/516,312, filed on Apr. 1, 2011.

(51) Int. Cl.
*C12N 15/113* (2010.01)
*C12Q 1/68* (2006.01)
*G01N 33/574* (2006.01)
*G01N 33/50* (2006.01)

(52) U.S. Cl.
CPC ......... *C12N 15/113* (2013.01); *C12N 15/1135* (2013.01); *C12Q 1/6886* (2013.01); *G01N 33/5011* (2013.01); *G01N 33/57434* (2013.01); *G01N 33/57438* (2013.01); *C12N 2310/11* (2013.01); *C12N 2310/111* (2013.01); *C12N 2310/14* (2013.01); *C12N 2310/141* (2013.01); *C12N 2310/531* (2013.01); *C12Q 2600/158* (2013.01)

(58) Field of Classification Search
USPC ........... 435/6.1, 6.19, 91.1, 91.31, 455, 6.11, 435/375; 514/44, 1, 2; 536/23.1, 24.5
See application file for complete search history.

(56) References Cited

U.S. PATENT DOCUMENTS

| | | |
|---|---|---|
| 4,945,050 A | 7/1990 | Sanford et al. |
| 5,036,006 A | 7/1991 | Sanford et al. |
| 5,100,792 A | 3/1992 | Sanford et al. |
| 5,459,127 A | 10/1995 | Felgner et al. |
| 5,580,859 A | 12/1996 | Felgner et al. |
| 5,589,466 A | 12/1996 | Felgner et al. |
| 5,824,519 A | 10/1998 | Norris et al. |
| 6,271,359 B1 | 8/2001 | Norris et al. |
| 2006/0030787 A1 | 2/2006 | Quay |
| 2007/0031881 A1 | 2/2007 | Boman |
| 2009/0004668 A1* | 1/2009 | Chen ............... C12N 15/111 435/6.14 |
| 2010/0028365 A1 | 2/2010 | Chant et al. |
| 2010/0093835 A1* | 4/2010 | McSwiggen et al. ...... 514/44 A |
| 2010/0169990 A1 | 7/2010 | Clarke |
| 2011/0076681 A1* | 3/2011 | Waterhouse et al. ............ 435/6 |
| 2011/0272346 A1* | 11/2011 | Descamps et al. ........... 210/513 |
| 2013/0022609 A1* | 1/2013 | Wang .................. A61K 31/337 424/141.1 |

FOREIGN PATENT DOCUMENTS

| | | |
|---|---|---|
| WO | WO 92/05263 | 4/1992 |
| WO | WO 94/21807 | 9/1994 |
| WO | WO 94/26914 | 11/1994 |
| WO | WO 95/18863 | 7/1995 |
| WO | WO 95/21931 | 8/1995 |
| WO | WO 96/17823 | 6/1996 |
| WO | WO 96/25508 | 8/1996 |
| WO | WO 02/44321 | * 5/2002 |
| WO | WO 2006/020071 | 2/2006 |

OTHER PUBLICATIONS

Romero-Benitez et al, Toxicol. & Appl. Pharmacol., vol. 194, pp. 230-238 (2004).*
Liu et al, Biochem. Pharmacol., vol. 51, pp. 1545-1551 (1996).*
Holen et al, (Nucleic Acids Res., vol. 30, No. 8, 1757-1766 (2002).*
Doench et al, Genes & Development, vol. 18, No. 5, pp. 504-511 (2004).*
International Search Report dated Mar. 30, 2012 received in International Application No. PCT/US2012/031574.
Attard et al., Characterization of ERG, AR and PTEN gene status in circulating tumor cells from patients with castration-resistant prostate cancer. Cancer Res. (2009) 69(7):2912-2918.
Beard et al. Transcription Mapping of Mouse Adenovirus Type 1 Early Region 3, Virol., (1990) 75: 81-90.
Bhardwaj et al, "Modulation of protein phosphatase 2A activity alters androgen-independent growth of prostate cancer cells: therapeutic implications". Mol Cancer Ther. (2011) 10(5):720-731.
Biroccio et al., "c-Myb and Bcl-x Overexpression Predicts Poor Prognosis in Colorectal Cancer: Clinical and Experimental Findings". Am J Pathol. (2001) 158(4):1289-1299.
Calabretta et al., "Normal and leukemic hematopoietic cells manifest differential sensitivity to inhibitory effects of c-myb antisense oligodeoxynucleotides: an in vitro study relevant to bone marrow purging". Proc Natl Acad Sci U S A i(1991) 88(6):2351-2355.
Cesi et al., "TGFbeta-induced c-Myb affects the expression of EMT-associated genes and promotes invasion of ER+ breast cancer cells". Cell Cycle. (2011) 10(23):4149-4161.
Chaturvedi et al., "MUC4 Mucin Potentiates Pancreatic Tumor Cell Proliferation, Survival, and Invasive Properties and Interferes with its Interaction to Extracellular Matrix Proteins", Mol Cancer Res. (2007) 5:309-20.

(Continued)

*Primary Examiner* — Jane Zara
(74) *Attorney, Agent, or Firm* — Knobbe, Martens, Olson & Bear LLP

(57) ABSTRACT

Some embodiments of the present technology relate to methods and compositions for the diagnosis and treatment of cancer. Some embodiments include methods and compositions for the diagnosis and treatment of castration-resistant prostate cancer. Some embodiments include methods and compositions for the diagnosis and treatment of pancreatic cancer.

25 Claims, 36 Drawing Sheets

(56) References Cited

OTHER PUBLICATIONS

Chen et al., "Interleukin 6 Activates Androgen Receptor-Mediated Gene Expression through a Signal Transducer and Activator of Transcription 3-dependent Pathway in LNCaP Prostate Cancer Cells", Cancer Res. (2000) 60(8):2132-2135.

Chen et al., "Transcription factor c-Myb promotes the invasion of hepatocellular carcinoma cells via increasing osteopontin expression". J Exp Clin Cancer Res. (2010) 29:172.

Cheng et al., "Short Hairpin RNA Knockdown of the Androgen Receptor Attenuates Ligand-independent Activation and Delays Tumor Progression". Cancer Res. (2006) 66(21):10613-10620.

Culig et al., "Mutant Androgen Receptor Detected in an Advanced-stage Prostatic Carcinoma is Activated by Adrenal Androgens and Progesterone". Mol Endocrinol. (1993) 7(12):1541-1550.

Curiel et al., High-Efficiency Gene Transfer Mediated by Adenovirus Coupled to DNA—Polylysine Complexes, Hum. Gene Ther. (1992) 3(2): 147-154.

Dean et al. Electroporation as a method for high-level nonviral gene transfer to the lung, Gene Ther. (2003) 10: 1608-1615.

Edwards et al., "Gene Amplifications Associated with the Development of Hormone-resistant Prostate Cancer". Clin Cancer Res. (2003) 9(14): 5271-5281.

Ellis et al., "Characterization of a Novel Androgen-sensitive, Prostate-specific Antigen-producing Prostatic Carcinoma Xenograft: LuCaP 23". Clin Cancer Res. (1996) 2(6):1039-1048.

Eto et al., C16 ceramide accumulates following androgen ablation in LNCaP prostate cancer cells. Prostate (2003) 57(1):66-79.

Feldman et al., The development of androgen-independent prostate cancer. Nat Rev Cancer. (2001) 1(1):34-45.

Felgner et al. Lipofection: A highly efficient, lipid-mediated DNA-transfection procedure, Proc. Natl. Acad. Sci. USA. (1987) 84: 7413-7417.

Felgner et al., Cationic Liposome-mediated transfection. Nature (1989) 337:387-388.

Goeddel; Systems for Heterologous Gene Expression. Academic Press, San Diego, Calif. Methods in Enzymology (1990) 185:3-7.

Gonda et al., Expression of myb, myc and fos proto-oncogenes during the differentiation of a murine myeloid leukaemia. Nature (1984) 310(5974): 249-251.

Hernandez-Munain et al., c-Myb and Core-binding Factor/PEBP2 Display Functional Synergy but Bind Independently to Adjacent Sites in the T-Cell Receptor delta Enhancer. Mol Cell Biol. (1995) 15(6): 3090-3099.

Hess et al., c-Myb is an essential downstream target for homeobox-mediated transformation of hematopoietic cells. Blood (2006) 108(1):297-304.

Hijiya et al., Biologic and therapeutic significance of MYB expression in human melanoma. Proc Natl Acad Sci U S A (1994) 91(10):4499-4503.

Hobisch et al. "Interleukin-6 regulates prostate-specific protein expression in prostate carcinoma cells by activation of the androgen receptor". Cancer Res.(1998) 58(20):4640-4645.

Jemal et al., Cancer statistics: 2010. CA Cancer J Clin. (2010) 60(5):277-300.

Jennbacken et al., Prostate cancer progression into androgen independency is associated with alterations in cell adhesion and invasivity. Prostate (2006) 66(15):1631-1640.

Kanei-Ishii et al., c-Myb-induced trans-Activation Mediated by Heat Shock Elements without Sequence-specific DNA Binding of c-Myb. J Biol Chem. (1994) 269(22):15768-15775.

Kaplitt et al., Expression of a Functional Foreign Gene in Adult Mammalian Brain following in Vivo Transfer via a Herpes Simplex Virus Type 1 Defective Viral Vector, Mol Cell Neurosci. (1991) 2: 320-330.

Karafiat et al., Transcription factor c-Myb is involved in the regulation of the epithelial-mesenchymal transition in the avian neural crest. Cell Mol Life Sci. (2005) 62(21):2516-2525.

Kauraniemi et al., MYB Oncogene Amplification in Hereditary BRCA1 Breast Cancer. Cancer Res. (2000) 60:5323-8.

Kim et al., Electro-gene therapy of collagen-induced arthritis by using an expression plasmid for the soluble p75 tumor necrosis factor receptor-Fc fusion protein, Gene Ther. (2003) 10: 1216-1224.

Knudsen et al., Multiple $G_1$ Regulatory Elements Control the Androgen-dependent Proliferation of Prostatic Carcinoma Cells. J Biol Chem. (1998) 273(32):20213-20222.

La Salle et al., An Adenovirus Vector for Gene Transfer into Neurons and Glia in the Brain, Science (1993) 259(5097): 988-990.

Lebkowski et al., Adeno-associated Virus: A Vector System for Efficient Introduction and Integration of DNA into a Variety of Mammalian Cell Types, Mol Cell Biol. (1988) 8(10): 3988-3996.

Lidonnici et al., Requirement of c-Myb for $p210^{BCR/ABL}$-dependent transformation of hematopoietic progenitors and leukemogenesis. Blood (2008) 111(9):4771-4779.

Locke et al., Androgen levels increase by intratumoral de novo steroidogenesis during progression of castration-resistant prostate cancer. Cancer Res. (2008) 68(15):6407-6415.

Lohr et al., Effective Tumor Therapy with Plasmid-encoded Cytokines Combined with in Vivo Electroporation, Cancer Res. (2001) 61: 3281-3284.

Machy et al., Gene transfer from targeted liposomes to specific lymphoid cells by electroporation. Proc. Natl. Acad. Sci. USA (1988) 85(21):8027-8031.

Malaterre et al., c-Myb is required for progenitor cell homeostasis in colonic crypts. Proc Natl Acad Sci U S A (2007) 104(10):3829-3834.

Melani et al., Inhibition of proliferation by c-myb antisense oligodeoxynucleotides in colon adenocarcinoma cell lines that express c-myb. Cancer Res. (1991) 51(11):2897-2901.

Miller et al., Improved Retroviral Vectors for Gene Transfer and Expression, BioTechniques. (1989) 7(9): 980-990.

Miyazaki et al., Telomestatin impairs glioma stem cell survival and growth through the disruption of telomeric G-quadruplex and inhibition of the proto-oncogene, c-Myb. Clin Cancer Res. (2012) 18(5):1268-1280.

Mucenski et al., A functional c-myb gene is required for normal murine fetal hepatic hematopoiesis. Cell (1991) 65(4):677-689.

Müller et al., c-myb transactivates the human cyclin A1 promoter and induces cyclin A1 gene expression. Blood (1999) 94(12):4255-4262.

Nakano et al., Cytokine Gene Therapy for Myocarditis by in vivo Electroporation, Hum Gene Ther. (2001) 12: 1289-1297.

Oelgeschläger et al., C/EBP, c-Myb, and PU.1 cooperate to regulate the neutrophil elastase promoter. Mol Cell Biol. (1996) 16(9):4717-4725.

Ohkawa et al., Activities of HIV-RNA targeted ribozymes transcribed from a 'shot-gun' type ribozyme-trimming plasmid, Oxford University Press, Nucleic Acids Symp. Ser. (1992) 27: 5-6.

Park et al., Large-scale molecular mapping of human c-myb locus: c-myb proto-oncogene is not involved in 6q-abnormalities of lymphoid tumors. Oncogene. (1992) 7(8):1603-1609.

Persson et al., Recurrent fusion of MYB and NFIB transcription factor genes in carcinomas of the breast and head and neck. Proc Natl Acad Sci U S A (2009) 106(44):18740-18744.

Pitsch et al., Inhibition of smooth muscle cell proliferation and migration in vitro by antisense oligonucleotide to c-myb. J Vasc Surg. (1996) 23(5):783-791.

Ramsay et al., MYB function in normal and cancer cells. Nat Rev Cancer. (2008) 8(7):523-534.

Salomoni et al., Resistance to apoptosis in CTLL-2 cells constitutively expressing c-Myb is associated with induction of BCL-2 expression and Myb-dependent regulation of bcl-2 promoter activity. Proc Natl Acad Sci U S A (1997) 94(7):3296-3301.

Samulski et al., A Recombinant Plasmid from which an Infectious Adeno-associated Virus Genome can be excised in vitro and its use to study Viral Replication, J Virol.(1987) 61(10): 3096-3101.

Samulski et al., Helper-Free Stocks of Recombinant Adeno-Associated Viruses: Normal Integration does not require Viral Gene Expression, J Virol. (1989) 63(9): 3822-3828.

(56) References Cited

OTHER PUBLICATIONS

Schröder, F.H. Progress in understanding androgen-independent prostate cancer (AIPC): a review of potential endocrine-mediated mechanisms. Eur Urol. (2008) 53(6):1129-1137.
Shankar et al., Pseudopodial actin dynamics control epithelial-mesenchymal transition in metastatic cancer cells. Cancer Res. (2010) 70(9):3780-3790.
Shapiro L.H., Myb and Ets proteins cooperate to transactivate an early myeloid gene. J Biol Chem. (1995) 270(15):8763-8771.
Singh et al., Inhibition of MUC4 expression suppresses pancreatic tumor cell growth and metastasis. Cancer Res. (2004) 64:622-630.
Singh et al., EMT, cancer stem cells and drug resistance: an emerging axis of evil in the war on cancer. Oncogene (2010) 29(34):4741-4751.
Singh et al., CXCL12-CXCR4 signalling axis confers gemcitabine resistance to pancreatic cancer cells: a novel target for therapy. Br J Cancer. (2010) 103(11):1671-1679.
Stamey et al., Prostate specific antigen in the diagnosis and treatment of adenocarcinoma of the prostate. IV. Anti-androgen treated patients. J Urol. (1989) 141(5):1088-1090.
Stratford-Perricaudet et al. Widespread long-term Gene Transfer to Mouse Skeletal Muscles and Heart, J Clin Invest. (1992) 90: 626-630.
Sun et al., miR-99 family of MicroRNAs suppresses the expression of prostate-specific antigen and prostate cancer cell proliferation. Cancer Res. (2011) 71(4):1313-1324.
Taira et al., Construction of a novel RNA-transcript-trimming plasmid which can be used both in vitro in place of run-off and (G)-free transcriptions and in vivo as multi-sequences transcription vectors. Nucleic Acids Res. (1991) 19(19):5125-5130.
Tanno et al., Expression of Slug is regulated by c-Myb and is required for invasion and bone marrow homing of cancer cells of different origin. J Biol Chem. (2010) 285(38):29434-29445.
Thompson et al., c-Myb down-regulation is associated with human colon cell differentiation, apoptosis, and decreased Bcl-2 expression. Cancer Res. (1998) 58(22):5168-5175.
Torelli et al., Expression of c-myb protooncogene and other cell cycle-related genes in normal and neoplastic human colonic mucosa. Cancer Res. (1987) 47(20):5266-5269.
Ulmer et al., Heterologous Protection Against Influenza by Injection of DNA Encoding a Viral Protein, Science (1993) 259(5102): 1745-1748.
Ventura et al., Activation of HIV-specific ribozyme activity by self-cleavage, Nucleic Acids Res., (1993) 21(14): 3249-3255.
Wallrapp et al., Characterization of a high copy number amplification at 6q24 in pancreatic cancer identifies c-myb as a candidate oncogene. Cancer Res. (1997) 57(15):3135-3139.
Wilkins et al., Estrogen prevents sustained COLO-205 human colon cancer cell growth by inducing apoptosis, decreasing c-myb protein, and decreasing transcription of the anti-apoptotic protein bcl-2. Tumour Biol. (2010) 31(1):16-22.
Williams et al., Introduction of foreign genes into tissues of living mice by DNA-coated microprojectiles, Proc. Natl. Acad. Sci. USA. (1991) 88: 2726-2730.
Wilson et al. Hepatocyte-directed Gene Transfer in Vivo Leads to Transient Improvement of Hypercholesterolemia in Low Density Lipoprotein Receptor-deficient Rabbits, J Biol Chem. (1992) 267(2): 963-967.
Wu et al., Receptor-mediated Gene Delivery and Expression in Vivo, J Biol Chem.(1988) 263(29): 14621-14624.
Yeung et al., Regions of prostate-specific antigen (PSA) promoter confer androgen-independent expression of PSA in prostate cancer cells. J Biol Chem. (2000) 275(52):40846-40855.
Young et al., Effect of a DNA nuclear targeting sequence on gene transfer and expression of plasmids in the intact vasculature, Gene Ther, (2003) 10: 1465-1470.
Yuan et al., c-Myb promotes the survival of CD4+CD8+ double-positive thymocytes through upregulation of Bcl-xL. J Immunol. (2010) 184(6):2793-2804.
Zorbas et al., c-Myb is critical for murine colon development. Oncogene (1999) 18(42):5821-5830.

* cited by examiner

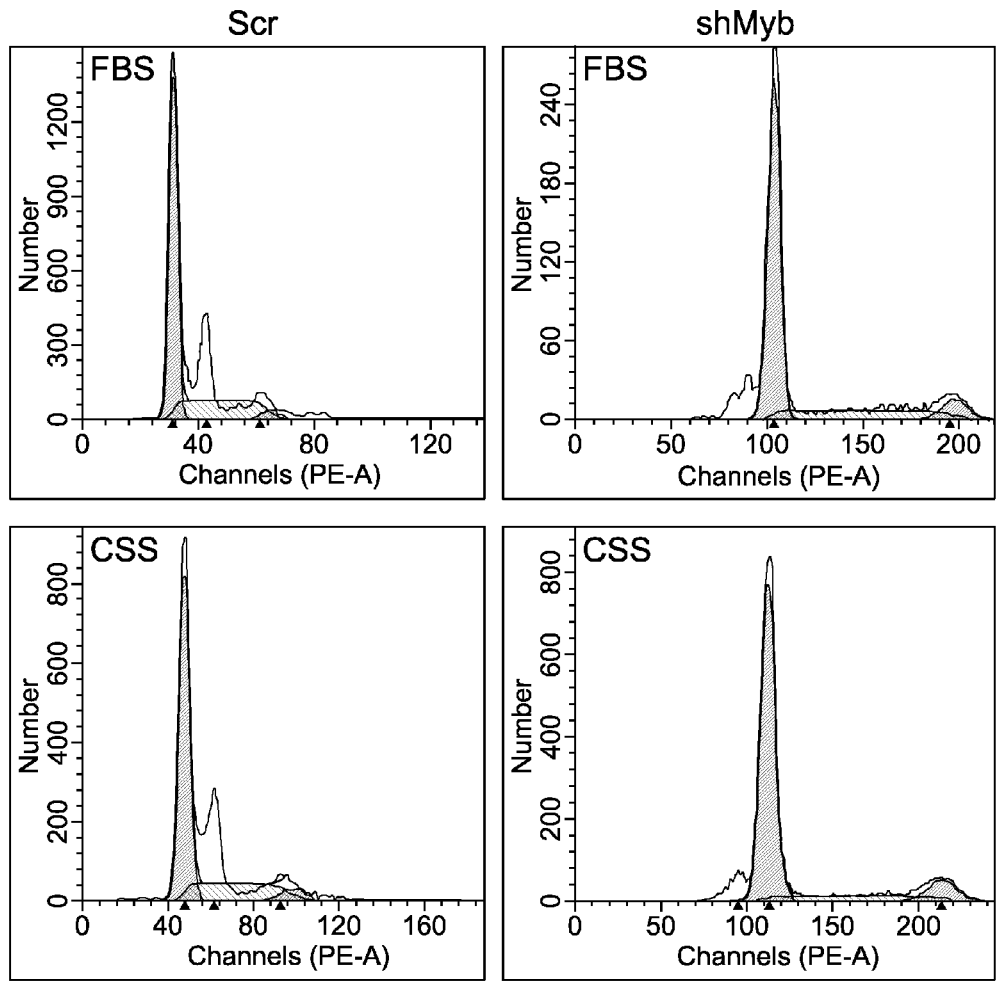
FIG. 4A - continued

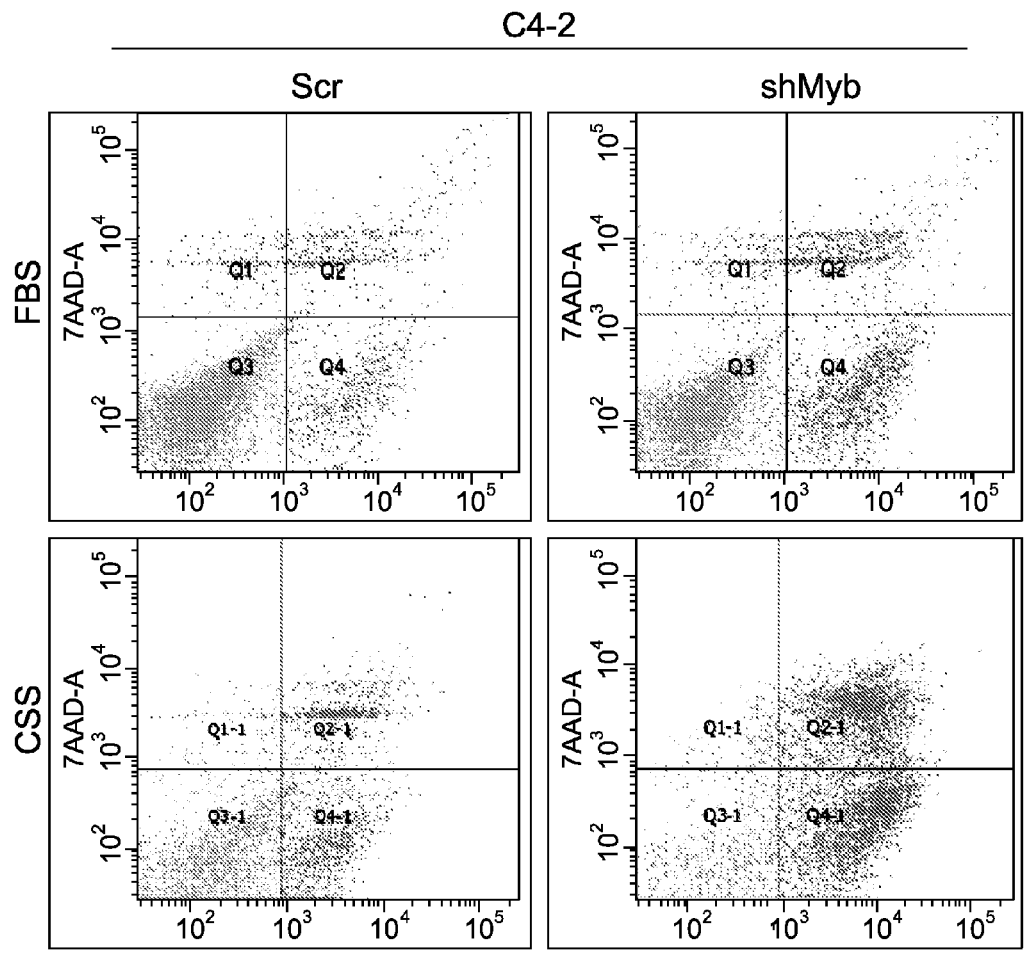
FIG. 4B - continued

SEQUENCE LISTING

<160> NUMBER OF SEQ ID NOS: 6

<210> SEQ ID NO 1
<211> LENGTH: 23
<212> TYPE: DNA
<213> ORGANISM: Artificial Sequence
<220> FEATURE:
<223> OTHER INFORMATION: primer

<400> SEQUENCE: 1
tcaggaaact tcttctgctc aca                                    23

<210> SEQ ID NO 2

-continued

```
<211> LENGTH: 18
<212> TYPE: DNA
<213> ORGANISM: Artificial Sequence
<220> FEATURE:
<223> OTHER INFORMATION: primer

<400> SEQUENCE: 2
aggttcccag gtactgct                                                 18

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
gctgtgtggc aaagtccaag                                               20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
ggtcaggctc ctggaagata                                               20

<210> SEQ ID NO 5
<211> LENGTH: 3309
<212> TYPE: DNA
<213> ORGANISM: Homo Sapiens

<400> SEQUENCE: 5
aatatcaacc tgtttcctcc tcctccttct cctcctcctc cgtgacctcc tcctcctctt     60
tctcctgaga aacttcgccc cagcggtgcg gagcgccgct cgcagccgg ggagggacgc     120 aggcaggcgg cgggcagcgg gaggcggcag cccggtgcgg tccccgcggc tctcggcgga    180
gccccgcgcc cgccgcgcca tggcccgaag accccggcac agcatatata gcagtgacga    240
ggatgatgag gactttgaga tgtgtgacca tgactatgat gggctgcttc ccaagtctgg    300
aaagcgtcac ttggggaaaa caaggtggac ccgggaagag gatgaaaaac tgaagaagct    360
ggtggaacag aatggaacag atgactggaa agttattgcc aattatctcc gaatcgaac    420 agatgtgcag tgccagcacc gatggcagaa agtactaaac cctgagctca tcaagggtcc    480
ttggaccaaa gaagaagatc agagagtgat agagcttgta cagaaatacg gtccgaaacg    540
ttggtctgtt attgccaagc acttaaaggg gagaattgga aaacaatgta gggagaggtg    600
gcataaccac ttgaatccag aagttaagaa aacctcctgg acagaagagg aagacagaat    660
tatttaccag gcacacaaga gactggggaa cagatgggca gaaatcgcaa agctactgcc    720
tggacgaact gataatgcta tcaagaacca ctggaattct acaatgcgtc ggaaggtcga    780
acaggaaggt tatctgcagg agtcttcaaa agccagccag ccagcagtgg ccacaagctt    840
ccagaagaac agtcatttga tgggttttgc tcaggctccg cctacagctc aactccctgc    900
cactggccag cccactgtta caacgactta ttcctattac cacatttctg aagcacaaaa    960
tgtctccagt catgttccat accctgtagc gttacatgta aatatagtca atgtccctca   1020
gccagctgcc gcagccattc agagacacta taatgatgaa gaccctgaga aggaaaagcg   1080
aataaaggaa ttagaattgc tcctaatgtc aaccgagaat gagctaaaag gacagcagac   1140
```

```
acagaaccac acatgcagct accccgggtg gcacagcacc accattgccg accacaccag    1200
acctcatgga gacagtgcac ctgtttcctg tttgggagaa caccactcca ctccatctct    1260
gccagcggat cctggctccc tacctgaaga aagcgcctcg ccagcaaggt gcatgatcgt    1320
ccaccagggc accattctgg ataatgttaa gaacctctta gaatttgcag aaacactcca    1380
atttatagat tctttcttaa acacttccag taaccatgaa aactcagact tggaaatgcc    1440
ttctttaact tccaccccc tcattggtca caaattgact gttacaacac catttcatag    1500
agaccagact gtgaaaactc aaaaggaaaa tactgttttt agaaccccag ctatcaaaag    1560
gtcaatctta gaaagctctc caagaactcc tacaccattc aaacatgcac ttgcagctca    1620
agaaattaaa tacggtcccc tgaagatgct acctcagaca ccctctcatc tagtagaaga    1680
tctgcaggat gtgatcaaac aggaatctga tgaatctgga attgttgctg agtttcaaga    1740
aaatggacca cccttactga agaaaatcaa acaagaggtg gaatctccaa ctgataaatc    1800
aggaaacttc ttctgctcac accactggga agggggacagt ctgaataccc aactgttcac    1860
gcagacctcg cctgtggcag atgcaccgaa tattcttaca agctccgttt taatggcacc    1920
agcatcagaa gatgaagaca atgttctcaa agcatttaca gtacctaaaa acaggtccct    1980
ggcgagcccc ttgcagcctt gtagcagtac ctgggaacct gcatcctgtg gaaagatgga    2040
ggagcagatg acatcttcca gtcaagctcg taaatacgtg aatgcattct cagcccggac    2100
gctggtcatg tgagacattt ccagaaaagc attatggttt tcagaacact tcaagttgac    2160
ttgggatata tcattcctca acatgaaact tttcatgaat gggagaagaa cctattttg     2220
ttgtggtaca acagttgaga gcagcaccaa gtgcatttag ttgaatgaag tcttcttgga    2280
tttcacccaa ctaaaaggat ttttaaaaat aaataacagt cttacctaaa ttattaggta    2340
atgaattgta gccagttgtt aatatcttaa tgcagatttt tttaaaaaaa acataaaatg    2400
atttatctgt atttttaaagg atccaacaga tcagtatttt ttcctgtgat gggttttttg    2460
aaatttgaca cattaaaagg tactccagta tttcactttt ctcgatcact aaacatatgc    2520
atatattttt aaaaatcagt aaaagcatta ctctaagtgt agacttaata ccatgtgaca    2580
tttaatccag attgtaaatg ctcatttatg gttaatgaca ttgaaggtac atttattgta    2640
ccaaaccatt ttatgagttt tctgttagct tgctttaaaa attattactg taagaaatag    2700
ttttataaaa aattatattt ttattcagta atttaatttt gtaaatgcca aatgaaaaac    2760
gtttttttgct gctatggtct tagcctgtag acatgctgct agtatcagag gggcagtaga    2820
gcttggacag aaagaaaaga aacttggtgt taggtaattg actatgcact agtatttcag    2880
acttttttaat tttatatata tatacatttt ttttccttct gcaatacatt tgaaaacttg    2940
tttgggagac tctgcatttt ttattgtggt ttttttgtta ttgttggttt atacaagcat    3000
gcgttgcact tcttttttgg gagatgtgtg ttgttgatgt tctatgtttt gttttgagtg    3060
tagcctgact gttttataat ttgggagttc tgcatttgat ccgcatcccc tgtggtttct    3120
aagtgtatgg tctcagaact gttgcatgga tcctgtgttt gcaactgggg agacagaaac    3180
tgtggttgat agccagtcac tgccttaaga acatttgatg caagatggcc agcactgaac    3240
ttttgagata tgacggtgta cttactgcct tgtagcaaaa taaagatgtg cccttatttt    3300
acctacaaa                                                            3309
```

<210> SEQ ID NO 6
<211> LENGTH: 29
<212> TYPE: DNA

```
<213> ORGANISM: Artificial Sequence
<220> FEATURE:
<223> OTHER INFORMATION: shRNA

<400> SEQUENCE: 6
cgttggtctg ttattgccaa gcacttaaa                                              29
```

METHODS AND COMPOSITIONS FOR THE DIAGNOSIS, CLASSIFICATION, AND TREATMENT OF CANCER

CROSS-REFERENCE TO RELATED APPLICATIONS

This application is the U.S. National Phase of Application No. PCT/US2012/031574 entitled "METHODS AND COMPOSITIONS FOR THE DIAGNOSIS, CLASSIFICATION, AND TREATMENT OF CANCER" filed Mar. 30, 2012 and published in English on Oct. 4, 2012 as WO2012/135696 which claims the benefit of U.S. Provisional Application No. 61/516,312 filed Apr. 1, 2011 entitled "C-MYB: A THERAPEUTIC TARGET AND A FUNCTIONAL BIOMARKER FOR PREDICTING DISEASE AGGRESSIVENESS/RECURRENCE/THERAPEUTIC RESISITANCE IN PROSTATE CANCER" which is incorporated herein by reference in its entirety.

STATEMENT REGARDING FEDERALLY SPONSORED R&D

This invention was made with government support under Grant No. W81XWH-09-1-0137 awarded by Department of Defense/U.S. Army, and CA137513 awarded by NIH/NCl. The government has certain rights in the invention.

REFERENCE TO SEQUENCE LISTING

The present application is being filed along with a Sequence Listing in electronic format. The Sequence Listing is provided as a file entitled USA_013WO.TXT, created Mar. 23, 2012, which is approximately 5 KB in size. The information in the electronic format of the Sequence Listing is incorporated herein by reference in its entirety.

FIELD OF THE INVENTION

Some embodiments of the present technology relate to methods and compositions for the diagnosis and treatment of cancer. Some embodiments include methods and compositions for the diagnosis and treatment of hormone-refractory prostate cancer. Some embodiments include methods and compositions for the diagnosis and treatment of pancreatic cancer.

BACKGROUND OF THE INVENTION

Cancers such as prostate cancer and pancreatic cancer are lethal disorders and major causes of death in the United States. In particular, prostate cancer is the most commonly diagnosed malignancy and second leading cause of cancer-related deaths in men in the United States (1). Effective treatment of early-stage localized disease involves surgery, such as radical prostatectomy, or radiation therapy; for advanced metastatic disease, androgen-deprivation therapy (ADT) is the first line of intervention. After an initial clinical response, prostate tumors relapse in a majority of cases as castration-resistant tumors, resulting in poor prognosis (2). Such a transition has been attributed to a variety of mechanisms that include AR overexpression, ligand-independent activation and other AR-independent mechanisms (3-6). Indeed, the development of prostate cancer and subsequent progression to castration-resistance is a complex process that may involve multiple genetic and epigenetic changes promoting proliferation, survival and aggressive behavior of prostate cancer cells (7). Accordingly, there is a need to development further diagnostic tools and therapies such disorders.

Pancreatic cancer is one of the most lethal malignancies. The overall median survival after diagnosis is 2-8 months, and only 1-4% of all patients with pancreatic adenocarcinoma survive 5 years after diagnosis (Bardeesy N, et al., Nat Rev Cancer 2002; 2:897-909; and Singh A P, et al., Cancer Res 2004; 64:622-30). According to an estimate of the American Cancer Society, 43,140 Americans were diagnosed with pancreatic cancer in 2010 and 36,800 died from it, marking this malignancy as the fourth leading cause of cancer deaths in the United States (Jemal A, et al., CA Cancer J Clin 2010; 60:277-300). The poor outcome from pancreatic cancer is due to late diagnosis and lack of effective therapy for treatment. In majority of cases, the disease is diagnosed at a stage when it is locally advanced or has already metastasized to distant organs. In that scenario, chemotherapy is considered as an option, but the effects are usually modest due to chemo-resistance (Arumugam T, et al., Cancer Res 2009; 69:5820-8).

SUMMARY OF THE INVENTION

Some embodiments of the methods and compositions provided herein include a method for evaluating the presence or stage of a cancer in a subject comprising measuring the expression level of a nucleic acid encoding c-Myb or a fragment thereof or the expression level of c-Myb protein or a fragment thereof or the activity of c-Myb protein in a sample obtained from the subject.

Some embodiments also include comparing the expression level of said nucleic acid encoding c-Myb or a fragment thereof or the expression level of said c-Myb protein or a fragment thereof or the activity of c-Myb protein in said sample to the expression level of said nucleic acid encoding c-Myb or a fragment thereof or the expression level of said c-Myb protein or a fragment thereof or the activity of c-Myb protein in normal tissue, tissue from a known cancer, or tissue from a known stage of cancer.

Some embodiments also include comparing the expression level of said nucleic acid encoding c-Myb or a fragment thereof or the expression level of said c-Myb protein or a fragment thereof or the activity of c-Myb protein in said sample to the level of expression of said nucleic acid encoding c-Myb or a level of expression of c-Myb protein or the activity of c-Myb protein known to be indicative of normal tissue, cancer, or a particular stage of cancer.

In some embodiments, an increased level of expression of said c-Myb protein or a fragment thereof or said nucleic acid encoding said c-Myb protein or a fragment thereof or the activity of c-Myb protein indicates the presence or stage of a cancer.

Some embodiments also include measuring the expression level of a nucleic acid encoding at least one marker or the expression level of at least one marker protein in addition to the expression level of said nucleic acid encoding c-Myb or a fragment thereof or the expression level of said c-Myb protein or a fragment thereof or the activity of c-Myb protein in said sample.

Some embodiments also include comparing the expression level of a nucleic acid encoding at least one marker or the expression level of at least one marker protein in said sample to the expression level of a nucleic acid encoding at least one marker or the expression level of at least one marker protein in normal tissue, tissue from a known cancer, or tissue from a known stage of cancer.

Some embodiments also include comparing the expression level of a nucleic acid encoding at least one marker or the expression level of at least one marker protein in said sample to the level of expression of said nucleic acid encoding at least one marker or the expression level of at least one marker protein known to be indicative of normal tissue, cancer or a particular stage of cancer.

In some embodiments, the at least one marker is selected from the group consisting of PSA, cyclin A1, cyclin D1, cyclin E1, Bcl-xL, Bcl2, N-cadherin, vimentin, slug, snail, twist, p27/KIP1, p21/WAF1, Bax, and CXCR4. In some embodiments, an increased level of expression of a nucleic acid encoding at least one marker or at least one marker protein indicates the presence or stage of a cancer, wherein the marker is selected from the group consisting of PSA, cyclin A1, cyclin D1, cyclin E1, Bcl-xL, Bcl2, N-cadherin, vimentin, slug, snail, and twist. In some embodiments, decreased level of expression of a nucleic acid encoding at least one marker or at least one marker protein indicates the presence or stage of a cancer, wherein the marker is selected from the group consisting of p27/KIP1, p21/WAF1, Bax, and CXCR4.

In some embodiments, the nucleic acid encoding c-Myb or a fragment thereof is an mRNA or a fragment thereof.

In some embodiments, the cancer is pancreatic cancer.

In some embodiments, the cancer is prostate cancer. In some embodiments, the cancer is castration-resistant prostate cancer. In some embodiments, the cancer is androgen-dependent prostate cancer.

In some embodiments, the sample is an ex vivo sample.

In some embodiments, the subject is a mammal. In some embodiments, the subject is a human.

Some embodiments of the methods and compositions provided herein include a method for increasing the sensitivity of a neoplastic cell to a chemotherapeutic agent comprising reducing the expression level of a nucleic acid encoding c-Myb or the expression level of c-Myb protein in the cell or reducing activity of c-Myb protein.

In some embodiments, the level of a nucleic acid encoding c-Myb or the level of c-Myb protein or the activity of c-Myb protein is reduced by contacting the cell with a sufficient amount of an isolated nucleic acid to increase the sensitivity of said cell to said chemotherapeutic agent, wherein said isolated nucleic acid is selected from a small hairpin RNA (shRNA), a small interfering RNA (siRNA), a micro RNA (miRNA), an antisense polynucleotide, and a ribozyme.

In some embodiments, the isolated nucleic acid comprises a sequence encoding c-Myb or a fragment thereof, a sequence encoding antisense c-Myb or a fragment thereof, or an antisense nucleic acid complementary to a sequence encoding c-Myb or a fragment thereof. In some embodiments, the isolated nucleic acid comprises SEQ ID NO:06.

In some embodiments, the neoplastic cell is a pancreatic cancer cell.

In some embodiments, the neoplastic cell is a prostate cancer cell. In some embodiments, the neoplastic cell is a castration-resistant prostate cancer cell. In some embodiments, the neoplastic cell is an androgen-dependent prostate cancer cell.

In some embodiments, the chemotherapy comprises administering a chemotherapeutic agent. In some embodiments, the chemotherapeutic agent is selected from the group consisting of docetaxel, and paclitaxel.

In some embodiments, the nucleic acid encoding c-Myb or a fragment thereof is an mRNA or a fragment thereof.

In some embodiments, the cell is a mammalian cell. In some embodiments, the cell is a human cell. In some embodiments, the cell is in vivo. In some embodiments, the cell is in vitro.

Some embodiments of the methods and compositions provided herein include a method for reducing cell cycle progression in a cell comprising reducing the expression level of a nucleic acid encoding c-Myb or the expression level of c-Myb protein or the activity of c-Myb protein in the cell.

In some embodiments, the level of a nucleic acid encoding c-Myb or the level of c-Myb protein or the activity of c-Myb protein is reduced by contacting the cell with a sufficient amount of an isolated nucleic acid to reduce cell cycle progression of said cell, wherein said isolated nucleic acid is selected from a small hairpin RNA (shRNA), a small interfering RNA (siRNA), a micro RNA (miRNA), an antisense polynucleotide, and a ribozyme.

Some embodiments of the methods and compositions provided herein include a method for reducing apoptosis resistance in a cell comprising reducing the expression level of a nucleic acid encoding c-Myb or the expression level of c-Myb protein or the activity of c-Myb protein in the cell.

In some embodiments, the level of a nucleic acid encoding c-Myb or the level of c-Myb protein or the activity of c-Myb protein is reduced by contacting the cell with a sufficient amount of an isolated nucleic acid to reduce apoptosis resistance in the cell, wherein said isolated nucleic acid is selected from a small hairpin RNA (shRNA), a small interfering RNA (siRNA), a micro RNA (miRNA), an antisense polynucleotide, and a ribozyme.

Some embodiments of the methods and compositions provided herein include a method for reducing or increasing expression of cell cycle or survival associated proteins in a cell comprising reducing the expression level of a nucleic acid encoding c-Myb or the expression level of c-Myb protein or the activity of c-Myb protein in the cell.

In some embodiments, the level of a nucleic acid encoding c-Myb or the level of c-Myb protein or the activity of c-Myb protein is reduced by contacting the cell with a sufficient amount of an isolated nucleic acid to reduce or increase expression of cell cycle or survival associated proteins in the cell, wherein said isolated nucleic acid is selected from a small hairpin RNA (shRNA), a small interfering RNA (siRNA), a micro RNA (miRNA), an antisense polynucleotide, and a ribozyme.

Some embodiments of the methods and compositions provided herein include a method for reducing motility or the invasive potential of a cell comprising reducing the expression level of a nucleic acid encoding c-Myb or the expression level of c-Myb protein or the activity of c-Myb protein in the cell.

In some embodiments, the level of a nucleic acid encoding c-Myb or the level of c-Myb protein or the activity of c-Myb protein is reduced by contacting the cell with a sufficient amount of an isolated nucleic acid to reduce motily or the invasive potential of the cell, wherein said isolated nucleic acid is selected from a small hairpin RNA (shRNA), a small interfering RNA (siRNA), a micro RNA (miRNA), an antisense polynucleotide, and a ribozyme.

Some embodiments of the methods and compositions provided herein include a method for increasing cell-cell interactions between more than one cell comprising reducing the expression level of a nucleic acid encoding c-Myb or the expression level of c-Myb protein or the activity of c-Myb protein in the cell.

In some embodiments, the level of a nucleic acid encoding c-Myb or the level of c-Myb protein or the activity of c-Myb protein is reduced by contacting the cell with a sufficient amount of an isolated nucleic acid to increase cell-cell interactions between the more than one cell, wherein said isolated nucleic acid is selected from a small hairpin RNA (shRNA), a small interfering RNA (siRNA), a micro RNA (miRNA), an antisense polynucleotide, and a ribozyme.

Some embodiments of the methods and compositions provided herein include a method for inhibiting an epithelial to mesenchymal transition by a cell comprising reducing the expression level of a nucleic acid encoding c-Myb or the expression level of c-Myb protein or the activity of c-Myb protein in the cell.

In some embodiments, the level of a nucleic acid encoding c-Myb or the level of c-Myb protein or the activity of c-Myb protein is reduced by contacting the cell with a sufficient amount of an isolated nucleic acid to inhibit an epithelial to mesenchymal transition by the cell, wherein said isolated nucleic acid is selected from a small hairpin RNA (shRNA), a small interfering RNA (siRNA), a micro RNA (miRNA), an antisense polynucleotide, and a ribozyme.

Some embodiments of the methods and compositions provided herein include a method for inhibiting c-myc or CXCR expression by a cell comprising reducing the expression level of a nucleic acid encoding c-Myb or the expression level of c-Myb protein or the activity of c-Myb protein in the cell.

In some embodiments, the level of a nucleic acid encoding c-Myb or the level of c-Myb protein or the activity of c-Myb protein is reduced by contacting the cell with a sufficient amount of an isolated nucleic acid to inhibit c-myc or CXCR expression by the cell, wherein said isolated nucleic acid is selected from a small hairpin RNA (shRNA), a small interfering RNA (siRNA), a micro RNA (miRNA), an antisense polynucleotide, and a ribozyme.

In some embodiments, the isolated nucleic acid comprises a sequence encoding c-Myb or a fragment thereof, a sequence encoding antisense c-Myb or a fragment thereof, or an antisense nucleic acid complementary to a sequence encoding c-Myb or a fragment thereof. In some embodiments, the isolated nucleic acid comprises SEQ ID NO:06.

In some embodiments, the neoplastic cell is a pancreatic cancer cell.

In some embodiments, the neoplastic cell is a prostate cancer cell. In some embodiments, the neoplastic cell is a castration-resistant prostate cancer cell. In some embodiments, the neoplastic cell is an androgen-dependent prostate cancer cell.

In some embodiments, the nucleic acid encoding c-Myb or a fragment thereof is an mRNA or a fragment thereof.

In some embodiments, the cell is a mammalian cell. In some embodiments, the cell is a human cell. In some embodiments, the cell is in vivo. In some embodiments, the cell is in vitro.

Some embodiments of the methods and compositions provided herein include a method for treating or ameliorating cancer in a subject comprising reducing the expression level of a nucleic acid encoding c-Myb or the expression level of c-Myb protein or the activity of c-Myb protein in a cell of the subject.

In some embodiments, the level of a nucleic acid encoding c-Myb or the level of c-Myb protein or the activity of c-Myb protein is reduced by contacting the cell with an isolated nucleic acid selected from a small hairpin RNA (shRNA), a small interfering RNA (siRNA), a micro RNA (miRNA), an antisense polynucleotide, and a ribozyme.

In some embodiments, the isolated nucleic acid comprises a sequence encoding c-Myb or a fragment thereof, a sequence encoding antisense c-Myb or a fragment thereof, or an antisense nucleic acid complementary to a sequence encoding c-Myb or a fragment thereof. In some embodiments, the isolated nucleic acid comprises SEQ ID NO:06.

In some embodiments, the cell is a pancreatic cancer cell.

In some embodiments, the cell is a prostate cancer cell. In some embodiments, the cell is a castration-resistant prostate cancer cell. In some embodiments, the cell is an androgen-dependent prostate cancer cell.

In some embodiments, the nucleic acid encoding c-Myb or a fragment thereof is an mRNA or a fragment thereof.

In some embodiments, the subject is a mammal. In some embodiments, the subject is human.

Some embodiments of the methods and compositions provided herein include a method for killing or retarding the growth of at least one cell comprising reducing the level of a nucleic acid encoding c-Myb or a fragment thereof or the level of c-Myb protein or a fragment thereof or the activity of c-Myb protein in the cell; and contacting the cell with an effective amount of a therapeutic compound, wherein the effective amount is reduced compared to a cell wherein the level of a nucleic acid encoding c-Myb or a fragment thereof or the level of c-Myb protein or a fragment thereof or the activity of c-Myb protein is not reduced.

In some embodiments, the level of a nucleic acid encoding c-Myb or a fragment thereof or the level of c-Myb protein or a fragment thereof or the activity of c-Myb protein is reduced by contacting the cell with an isolated nucleic acid selected from a small hairpin RNA (shRNA), a small interfering RNA (siRNA), a micro RNA (miRNA), an antisense polynucleotide, and a ribozyme.

In some embodiments, the isolated nucleic acid comprises a sequence encoding c-Myb or a fragment thereof, a sequence encoding antisense c-Myb or a fragment thereof, or an antisense nucleic acid complementary to a sequence encoding c-Myb or a fragment thereof.

In some embodiments, the isolated nucleic acid comprises SEQ ID NO:06.

In some embodiments, the therapeutic compound comprises a chemotherapeutic agent. In some embodiments, the chemotherapeutic agent is selected from the group consisting of docetaxel, and paclitaxel.

In some embodiments, the at least one cell comprises at least one neoplastic cell.

In some embodiments, the cell is a pancreatic cancer cell.

In some embodiments, the cell is a prostate cancer cell. In some embodiments, the cell is a castration-resistant prostate cancer cell. In some embodiments, the cell is an androgen-dependent prostate cancer cell.

In some embodiments, the nucleic acid encoding c-Myb or a fragment thereof is an mRNA or a fragment thereof.

In some embodiments, the subject is a mammal. In some embodiments, the subject is a human.

In some embodiments, the cell is in vivo. In some embodiments, the cell is in vitro.

Some embodiments of the methods and compositions provided herein include a method for reducing the dosage of a therapeutic compound needed to treat a disorder in a subject comprising reducing the level of a nucleic acid encoding c-Myb or the level of c-Myb protein or the activity of c-Myb protein in a cell of the subject.

In some embodiments, the level of a nucleic acid encoding c-Myb or the level of c-Myb protein or the activity of c-Myb protein is reduced by contacting the cell with an isolated nucleic acid selected from a small hairpin RNA (shRNA), a small interfering RNA (siRNA), a micro RNA (miRNA), an antisense polynucleotide, and a ribozyme.

In some embodiments, the isolated nucleic acid comprises a sequence encoding c-Myb or a fragment thereof, a sequence encoding antisense c-Myb or a fragment thereof, or an antisense nucleic acid complementary to a sequence encoding c-Myb or a fragment thereof. In some embodiments, the nucleic acid comprises SEQ ID NO:06.

In some embodiments, the therapeutic compound comprises a chemotherapeutic agent. In some embodiments, the chemotherapeutic agent is selected from the group consisting of docetaxel, and paclitaxel.

In some embodiments, the cell comprises a neoplastic cell.

In some embodiments, the cell is a pancreatic cancer cell.

In some embodiments, the cell is a prostate cancer cell. In some embodiments, the cell is a castration-resistant prostate cancer cell. In some embodiments, the cell is an androgen-dependent prostate cancer cell.

In some embodiments, the nucleic acid encoding c-Myb or a fragment thereof is an mRNA or a fragment thereof.

In some embodiments, the subject is a mammal. In some embodiments, the subject is a human.

Some embodiments of the methods and compositions provided herein include a method for identifying a therapeutic compound comprising contacting a target cell with a test compound; and determining whether the test compound reduces the level of a nucleic acid encoding c-Myb or a fragment thereof or the level of c-Myb protein or a fragment thereof or the activity of c-Myb protein in the target cell.

Some embodiments also include comparing the level of a nucleic acid encoding c-Myb or a fragment thereof or the level of c-Myb protein or a fragment thereof or the activity of c-Myb protein in a target cell which has not been contacted with the test compound to the level of a nucleic acid encoding c-Myb or a fragment thereof or the level of c-Myb protein or a fragment thereof or the activity of c-Myb protein in a target cell contacted with the test compound.

Some embodiments also include determining whether the test compound reduces the level of a nucleic acid encoding PSA or a fragment thereof in the target cell.

Some embodiments also include comparing the level of a nucleic acid encoding PSA or a fragment thereof in a target cell which has not been contacted with the test compound to the level of a nucleic acid encoding PSA or a fragment thereof in a target cell contacted with the test compound.

Some embodiments also include determining whether the test compound reduces the level of a nucleic acid encoding CXCR4 or a fragment thereof or the level of CXCR4 protein or a fragment thereof in the target cell.

Some embodiments also include comparing the level of a nucleic acid encoding CXCR4 or a fragment thereof or the level of CXCR4 protein or a fragment thereof in a target cell which has not been contacted with the test compound to the level of a nucleic acid encoding CXCR4 or a fragment thereof or the level of CXCR4 protein or a fragment thereof in a target cell contacted with the test compound.

In some embodiments, the target cell comprises a neoplastic cell.

In some embodiments, the target cell is a pancreatic cancer cell.

In some embodiments, the target cell is a prostate cancer cell. In some embodiments, the target cell is a castration-resistant prostate cancer cell. In some embodiments, the target cell is an androgen-dependent prostate cancer cell.

In some embodiments, the nucleic acid encoding c-Myb or a fragment thereof is an mRNA or a fragment thereof.

In some embodiments, the target cell is a mammalian cell. In some embodiments, the target cell is a human cell.

Some embodiments of the methods and compositions provided herein include a method for identifying a therapeutic compound comprising contacting a target cell expressing c-Myb and androgen receptor with a test compound and determining whether said test compound reduces the formation of a complex comprising c-Myb and said androgen receptor.

In some embodiments, the target cell comprises a neoplastic cell. In some embodiments, the target cell is a prostate cancer cell. In some embodiments, the target cell is a castration-resistant prostate cancer cell. In some embodiments, the target cell is an androgen-dependent prostate cancer cell.

In some embodiments, the nucleic acid encoding c-Myb or a fragment thereof is an mRNA or a fragment thereof.

In some embodiments, the target cell is a mammalian cell. In some embodiments, the target cell is a human cell.

Some embodiments of the methods and compositions provided herein include a method for assessing the potential effectiveness of a test nucleic acid as a therapeutic agent comprising determining whether the test nucleic acid reduces the level of a nucleic acid encoding c-Myb or a fragment thereof or the level of c-Myb protein or a fragment thereof or the activity of c-Myb protein in a target cell, wherein the test nucleic acid is identified as having potential effectiveness as a therapeutic agent if the test nucleic acid reduces the level of the nucleic acid encoding c-Myb or a fragment thereof or the level of the c-Myb protein or a fragment thereof or the activity of c-Myb protein in said target cell.

Some embodiments also include determining whether the test nucleic acid reduces the level of a nucleic acid encoding PSA or a fragment thereof in the target cell.

Some embodiments also include comprising comparing the level of a nucleic acid encoding PSA or a fragment thereof in a target cell which has not been contacted with the test nucleic acid to the level of a nucleic acid encoding PSA or a fragment thereof in a target cell contacted with the test nucleic acid.

Some embodiments also include comprising determining whether the test nucleic acid reduces the level of a nucleic acid encoding CXCR4 or a fragment thereof or the level of CXCR4 protein or a fragment thereof in the target cell.

Some embodiments also include comprising comparing the level of a nucleic acid encoding CXCR4 or a fragment thereof or the level of CXCR4 protein or a fragment thereof in a target cell which has not been contacted with the test nucleic acid to the level of a nucleic acid encoding CXCR4 or a fragment thereof or the level of CXCR4 protein or a fragment thereof in a target cell contacted with the test nucleic acid.

In some embodiments, the target cell comprises a neoplastic cell.

In some embodiments, the target cell is a pancreatic cancer cell.

In some embodiments, the target cell is a prostate cancer cell. In some embodiments, the target cell is a castration-resistant prostate cancer cell. In some embodiments, the target cell is an androgen-dependent prostate cancer cell.

In some embodiments, the nucleic acid encoding c-Myb or a fragment thereof is an mRNA or a fragment thereof.

In some embodiments, the target cell is a mammalian cell. In some embodiments, the target cell is a human cell.

Some embodiments of the methods and compositions provided herein include a nucleic acid identified as having potential effectiveness as a therapeutic agent by any method provided herein.

Some embodiments of the methods and compositions provided herein include an isolated nucleic acid comprising a sequence encoding c-Myb or a fragment thereof, a sequence encoding antisense c-Myb or a fragment thereof, or a nucleic acid complementary to a sequence encoding c-Myb or a fragment thereof, wherein the nucleic acid reduces the level of a nucleic acid encoding c-Myb or the level of c-Myb protein in a cell.

In some embodiments, the isolated nucleic acid is selected from a small hairpin RNA (shRNA), a small interfering RNA (siRNA), a micro RNA (miRNA), an antisense polynucleotide, and a ribozyme.

In some embodiments, the isolated nucleic acid comprises SEQ ID NO:06.

Some embodiments of the methods and compositions provided herein include a vector comprising any one of the isolated nucleic acids provided herein.

Some embodiments of the methods and compositions provided herein include a cell comprising any one of the isolated nucleic acids provided herein.

Some embodiments of the methods and compositions provided herein include a pharmaceutical composition comprising any one of the isolated nucleic acids provided herein, and a pharmaceutically acceptable carrier.

Some embodiments of the methods and compositions provided herein include use of an isolated nucleic acid for increasing the sensitivity of a neoplastic cell to chemotherapy, wherein the isolated nucleic acid reduces the expression level of a nucleic acid encoding c-Myb or the expression level of c-Myb protein or the activity of c-Myb protein in the cell.

In some embodiments, the isolated nucleic acid is selected from a small hairpin RNA (shRNA), a small interfering RNA (siRNA), a micro RNA (miRNA), an antisense polynucleotide, and a ribozyme.

In some embodiments, the isolated nucleic acid comprises a sequence encoding c-Myb or a fragment thereof, a sequence encoding antisense c-Myb or a fragment thereof, or an antisense nucleic acid complementary to a sequence encoding c-Myb or a fragment thereof.

In some embodiments, the isolated nucleic acid comprises SEQ ID NO:06.

In some embodiments, the neoplastic cell is a pancreatic cancer cell.

In some embodiments, the neoplastic cell is a prostate cancer cell. In some embodiments, the neoplastic cell is a castration-resistant prostate cancer cell. In some embodiments, the neoplastic cell is an androgen-dependent prostate cancer cell.

In some embodiments, the chemotherapy comprises the administration of a chemotherapeutic agent.

In some embodiments, the chemotherapeutic agent is selected from the group consisting of docetaxel, and paclitaxel.

In some embodiments, the nucleic acid encoding c-Myb or a fragment thereof is an mRNA or a fragment thereof.

In some embodiments, the cell is a mammalian cell. In some embodiments, the cell is a human cell. In some embodiments, the cell is in vivo. In some embodiments, the cell is in vitro.

Some embodiments of the methods and compositions provided herein include use of an isolated nucleic acid for treating or ameliorating cancer in a subject, wherein the isolated nucleic acid reduces the expression level of a nucleic acid encoding c-Myb or the expression level of c-Myb protein or the activity of c-Myb protein in a cell of the subject.

In some embodiments, the isolated nucleic acid is selected from a small hairpin RNA (shRNA), a small interfering RNA (siRNA), a micro RNA (miRNA), an antisense polynucleotide, and a ribozyme.

In some embodiments, the isolated nucleic acid comprises a sequence encoding c-Myb or a fragment thereof, a sequence encoding antisense c-Myb or a fragment thereof, or an antisense nucleic acid complementary to a sequence encoding c-Myb or a fragment thereof. In some embodiments, the nucleic acid comprises SEQ ID NO:06.

In some embodiments, the cell is a pancreatic cancer cell.

In some embodiments, the cell is a prostate cancer cell. In some embodiments, the cell is a castration-resistant prostate cancer cell. In some embodiments, the cell is an androgen-dependent prostate cancer cell.

Some embodiments also include the use of a chemotherapeutic agent to treat said subject. In some embodiments, the chemotherapeutic agent is selected from the group consisting of docetaxel, and paclitaxel.

In some embodiments, the nucleic acid encoding c-Myb or a fragment thereof is an mRNA or a fragment thereof.

In some embodiments, the subject is a mammal. In some embodiments, the subject is human.

Some embodiments of the methods and compositions provided herein include use of an isolated nucleic acid for killing or retarding the growth of at least one cell, wherein the isolated nucleic acid reduces the level of a nucleic acid encoding c-Myb or the level of c-Myb protein or the activity of c-Myb protein in the cell; and the cell is contacted with an effective amount of a therapeutic compound, wherein the effective amount is reduced compared to a cell wherein the level of a nucleic acid encoding c-Myb or the level of c-Myb protein or the activity of c-Myb protein is not reduced.

In some embodiments, the isolated nucleic acid is selected from a small hairpin RNA (shRNA), a small interfering RNA (siRNA), a micro RNA (miRNA), an antisense polynucleotide, and a ribozyme.

In some embodiments, the isolated nucleic acid comprises a sequence encoding c-Myb or a fragment thereof, a sequence encoding antisense c-Myb or a fragment thereof, or an antisense nucleic acid complementary to a sequence encoding c-Myb or a fragment thereof. In some embodiments, the nucleic acid comprises SEQ ID NO:06.

In some embodiments, the therapeutic compound comprises a chemotherapeutic agent. In some embodiments, the chemotherapeutic agent is selected from the group consisting of docetaxel, and paclitaxel.

In some embodiments, the one cell comprises a neoplastic cell.

In some embodiments, the cell is a pancreatic cancer cell.

In some embodiments, the cell is a prostate cancer cell. In some embodiments, the cell is a castration-resistant prostate cancer cell. In some embodiments, the cell is an androgen-dependent prostate cancer cell.

In some embodiments, the nucleic acid encoding c-Myb or a fragment thereof is an mRNA or a fragment thereof.

In some embodiments, the subject is a mammal. In some embodiments, the subject is a human. In some embodiments, the cell is in vivo. In some embodiments, the cell is in vitro.

Some embodiments of the methods and compositions provided herein include use of an isolated nucleic acid for reducing the dosage of a therapeutic compound needed to treat a disorder in a subject, wherein the level of a nucleic acid encoding c-Myb or the level of c-Myb protein or the activity of c-Myb protein is reduced in a cell of the subject.

In some embodiments, the isolated nucleic acid is selected from a small hairpin RNA (shRNA), a small interfering RNA (siRNA), a micro RNA (miRNA), an antisense polynucleotide, and a ribozyme.

In some embodiments, the isolated nucleic acid comprises a sequence encoding c-Myb or a fragment thereof, a sequence encoding antisense c-Myb or a fragment thereof, or an antisense nucleic acid complementary to a sequence encoding c-Myb or a fragment thereof. In some embodiments, the nucleic acid comprises SEQ ID NO:06.

In some embodiments, the therapeutic compound comprises a chemotherapeutic agent. In some embodiments, the chemotherapeutic agent is selected from the group consisting of docetaxel, and paclitaxel.

In some embodiments, the cell comprises a neoplastic cell.

In some embodiments, the cell is a pancreatic cancer cell.

In some embodiments, the cell is a prostate cancer cell. In some embodiments, the cell is a castration-resistant prostate cancer cell. In some embodiments, the cell is an androgen-dependent prostate cancer cell.

In some embodiments, the nucleic acid encoding c-Myb or a fragment thereof is an mRNA or a fragment thereof.

In some embodiments, the subject is a mammal. In some embodiments, the subject is a human.

BRIEF DESCRIPTION OF THE DRAWINGS

FIG. 1A shows quantitative analysis of Myb transcripts in normal/benign human prostate epithelial (RWPE1 and RWPE2) and cancer (LNCaP, C4-2, DU145, and PC3) cell lines. Real-time PCR assay was performed on reverse-transcribed RNA using Myb and GAPDH (internal control) primers. Relative quantities of Myb-specific PCR product was determined using the 2-ΔΔCT method. Bars represent the mean±S.D (n=3); *, p<0.05. FIG. 1B shows immunoblot analysis of Myb and β-actin (internal control) in prostate cell lines. Quantitative evaluation was done by densitometry. Bars represent the mean of fold ratio±S.D (n=3); *, p<0.05. Negligible Myb expression was observed in normal/benign human prostate epithelial cells, while, expression of Myb was significantly higher in AI (C4-2, DU145, and PC3) cells as compared to AD (LNCaP) prostate cancer cells. FIG. 1C shows an immunofluorescence analysis of Myb expression and sub-cellular localization in lineage associated LNCaP (AD) and C4-2 (AI) cells. Following fixation, cells were probed with rabbit anti-Myb monoclonal antibody and subsequently incubated with TRITC conjugated goat anti-rabbit secondary antibodies. Immunostained cells were visualized under Nikon Eclipse TE2000-U fluorescent microscope. An overexpression of Myb was observed in C4-2 prostate cancer cells with predominant nuclear and diffused cytoplasmic localization.

FIG. 2A shows an immunoblot analysis of Myb expression in stable pooled populations of Myb overexpressing LNCaP (LNCaP-Myb), Myb-silenced C4-2 (C4-2-shMyb) and their respective empty vector (LNCaP-Neo)- and scrambled-shRNA (C4-2-Src)-transfected control lines. β-actin was used as an internal control. FIG. 2B shows growth kinetics measurements of LNCaP-Myb and C4-2-shMyb cells along with their respective controls. Cells ($1\times10^4$) were seeded in 6-well plates and growth monitored by counting of the cells every day for 8 days. Growth curve represents the data from triplicate experiments (mean±S.D). Cell growth was increased (~29.4%) in LNCaP-Myb and decreased in C4-2 sh-Myb (~37.6%) as compared to their respective controls, when compared on 8th day. FIG. 2C shows population doubling time (PDT) was calculated as described in materials and methods herein. Bars represent mean±S.D. (n=3); *, p<0.05. FIG. 2D shows a soft agar colony forming assay was performed as described in materials and methods. Bars represent the mean of total number of colonies in 10 random view fields±S.D (n=3); *, p<0.05. Myb overexpressing (LNCaP-Myb and C4-2-Scr) cells were more clonogenic (~4.98-fold and ~2.4-fold, respectively) as compared to low Myb-expressing (LNCaP-Neo and C4-2-shMyb) prostate cancer cells.

FIG. 3A depicts cells seeded at low density ($1\times10^3$ cells/well) in steroidsupplemented (FBS) and -reduced (CSS) media. After 2 weeks, colonies were stained with crystal violet, and visualized and photographed using imaging system. Bars represented mean±S.D. n=3; *, p<0.05. Myb overexpression is associated with enhanced colony formation and the ability of prostate cancer cells to sustain clonogenic potential under androgen-reduced condition. FIG. 3B shows PSA and AR expression under steroid supplemented and -reduced condition in Myb-overexpressing or -silenced prostate cancer cells. Cells were grown in regular (FBS) or steroid-reduced (CSS) media for 48 h and the expression of PSA and AR was examined by immunoblot analysis. Myb-overexpression or -silencing led to induction or repression of PSA expression, respectively, while no effect on AR expression was observed. The expression of both PSA and AR decreased under steroid-reduced condition; however, Myb-overexpressing prostate cancer cells had a greater potency to sustain PSA expression.

FIG. 4A shows a cell cycle analysis. Synchronized cultures of high (LNCaP-Myb and C4-2-Scr) or low Myb (LnCaP-Neo and C4-2-shMyb)-expressing prostate cancer cells were incubated with steroid-supplemented (FBS) or -reduced (CSS) media for 24 h. Subsequently, distribution of cells in different phases of cell cycle was analyzed by propidium iodide (PI) staining followed by flow cytometry. A greater proportion (1.45- and 1.47-folds, respectively) of Myb-overexpressing cells (LNCaP-Myb and C4-2-Scr) were in the S phase as compared to low Myb-expressing (LNCaP-Neo and C4-2-shMyb) prostate cancer cells. Furthermore, a relatively lesser impact of steroid-deprivation (fold-decrease in % cells in S-phase) was observed in Myb-overexpressing cells (LNCaP-Myb, 1.58-fold; C4-2-Scr, 1.15-fold) as compared to low Myb-expressing (LNCaP-Neo, 3.50-fold; C4-2-shMyb, 1.98-fold) prostate cancer cells. FIG. 4B shows an apoptosis assay. Myb-overexpressing or -silenced prostate cancer cells along with their respective controls were assessed for apoptosis, when cultured under steroid-supplemented and -reduced conditions for 96 h. Percentage of apoptotic cells were analyzed by flow cytometry using PE Annexin V. Myb-overexpressing cells (LNCaP-Myb, 23.7%; C4-2-Scr, 9.6%) exhibited lesser apoptotic indices as compared to low Myb-expressing cells (LNCaP-Neo, 34.4%; C4-2-shMyb, 20.2%). Data shows that Myb protects the cells from steroid-deprivation induced apoptosis. Steroid-deprivation further enhanced the apoptosis; however, lesser induction was observed in Myb-overexpressing cells (LNCaP-Myb, 1.36- fold; C4-2-Scr, 1.62-fold) as compared to low Myb-expressing cells (LNCaP-Neo, 2.02-fold; C4-2-shMyb, 2.13-fold).

Figure 5:
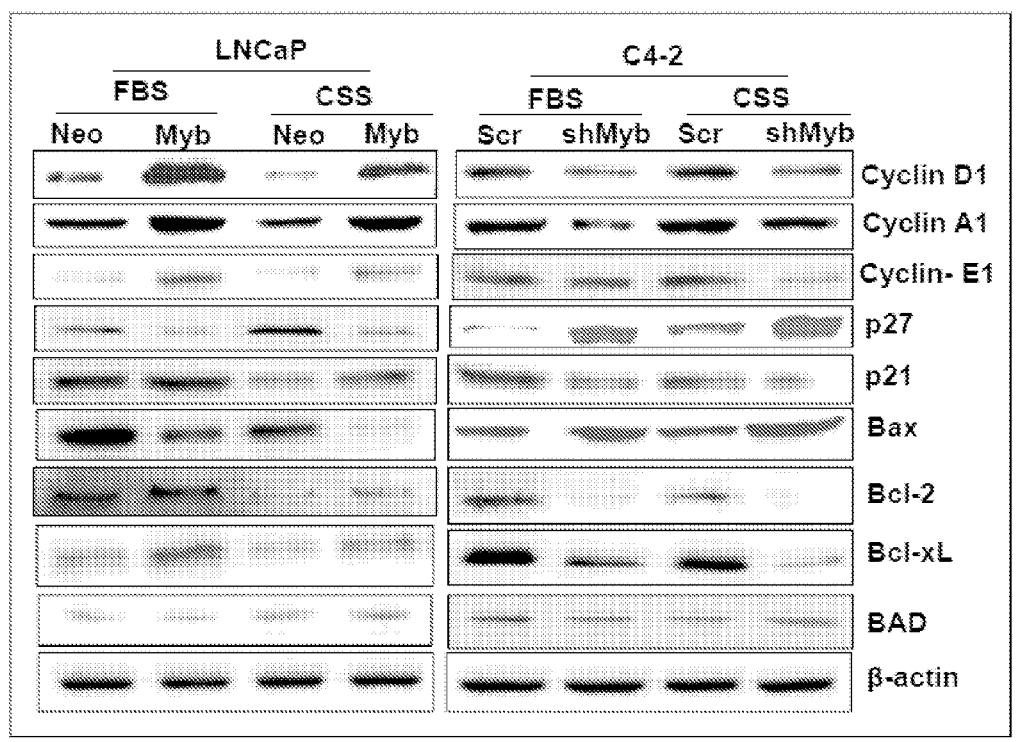

FIG. 5 shows Myb alters the expression of proteins associated with cell-cycle and apoptosis. Myb-overexpressing (LNCaP-Myb) or -silenced (C4-2-shMyb) cells along with their control (LNCaP-Neo and C4-2-Scr, respectively) cells were examined for the expression of various cell-cycle and survival-associated proteins under steroid-supplemented and reduced condition. β-actin was used as an internal control. Myb-overexpressing (LNCaPMyb) cells exhibited an induced expression of cyclins (A1, D1, E1), p21 (cyclin inhibitor), and anti-apoptotic Bcl-2 and Bcl-xL proteins, while a decreased expression of p27 (cyclin inhibitor) and pro-apoptotic Bax was observed. Likewise, silencing of Myb in C4-2 cells led to down-modulation of cyclin d (A1, D1, E1), p21, Bcl-2 and Bcl-xL and upregulation of p27 and Bax under both steroid-supplemented and -reduced conditions. No change, however, was observed in the expression of pro-apoptotic, BAD.

Figure 6A:
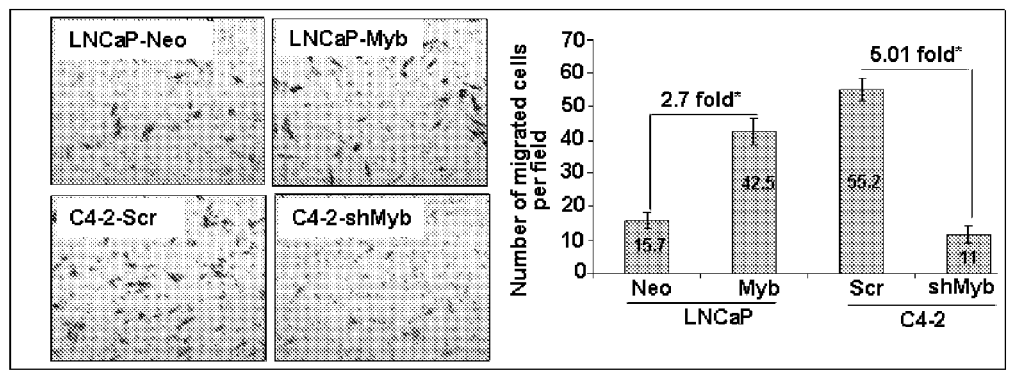
Figure 6B:
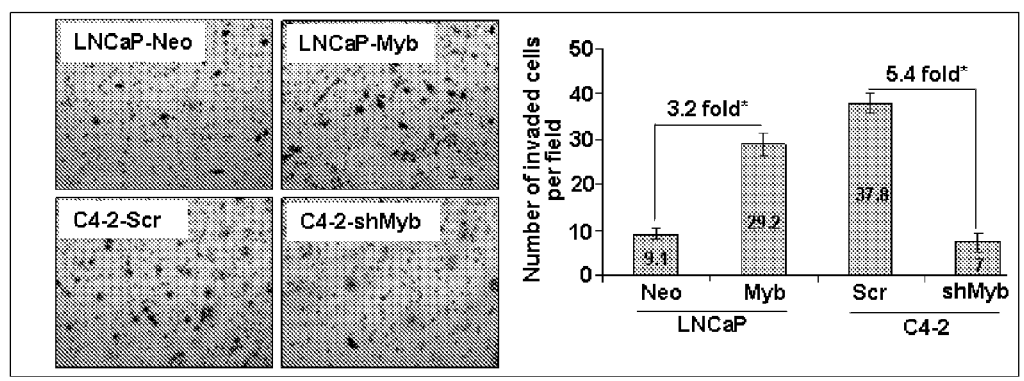
Figure 6C:
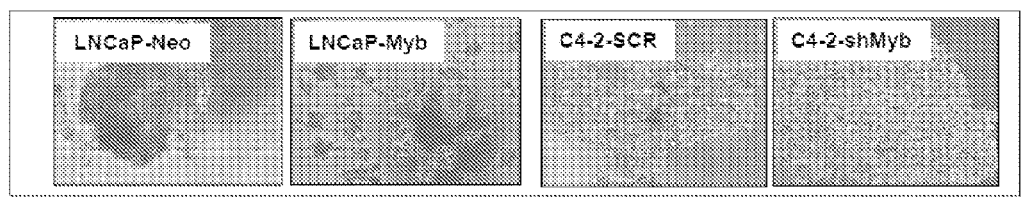

FIG. 6A, FIG. 6B, FIG. 6C show the role of Myb in motility, invasion and homotypic cell-cell interaction. Cells were seeded on noncoated or Matrigel-coated membranes for motility (FIG. 6A) and invasion (FIG. 6B) assays, respectively, and incubated for 16 h. Media containing 10% FBS in the lower chamber was used as a chemoattractant. Cells that had migrated or invaded through the membrane/ Matrigel to the bottom of the insert were fixed, stained and counted in 10 random view fields. Bars represent the mean±S.D (n=3) of number of migrated or invaded cells per field; *, p<0.05. LNCaP-Myb and C4-2-Scr cells were more motile (2.7- and 5.01-folds, respectively) as compared to LNCaP-Neo and C4-2-shMyb cells. Similarly, LNCaP-Myb and C4-2-Scr cells exhibited greater invasive potential (3.2 and 5.4-folds, respectively) as compared to LNCaP-Neo and C4-2-shMyb cells. FIG. 6C shows the effect on cell-cell interaction determined by hanging drop assay. Overexpression of Myb was associated with diminished cell-cell interaction in both LNCaP and C4-2 prostate cancer cells.

Figure 7A:
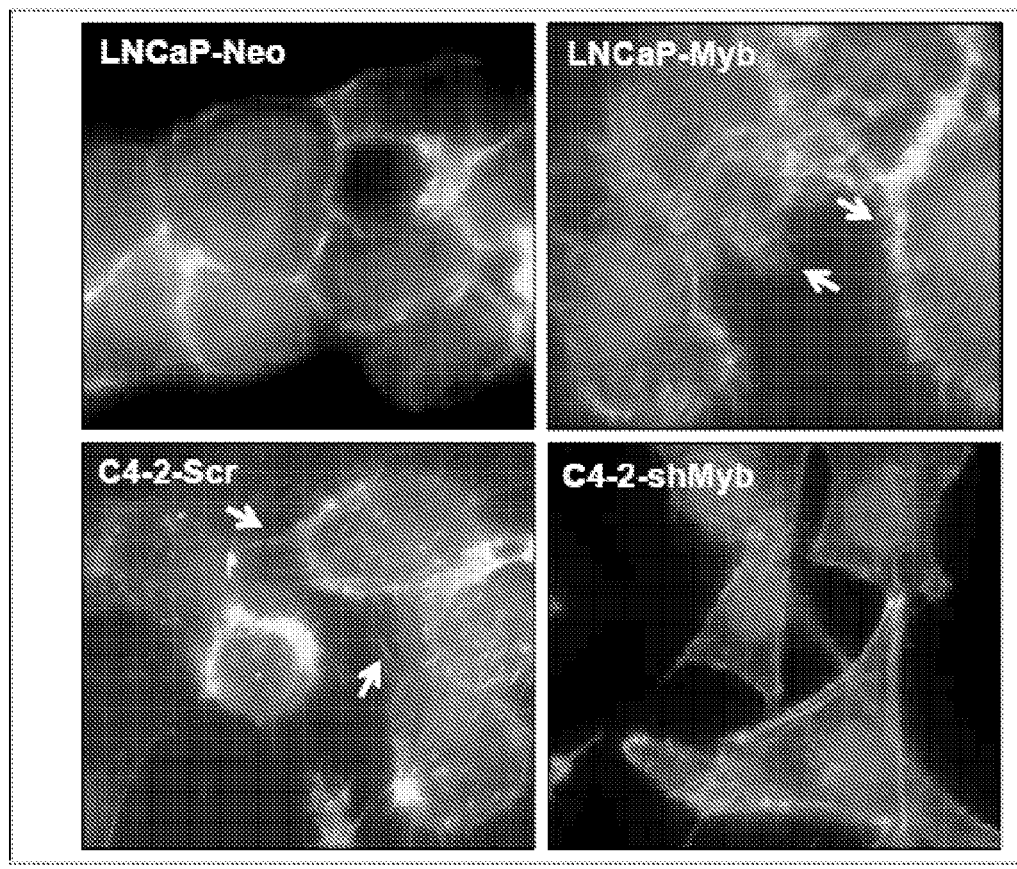
Figure 7B:
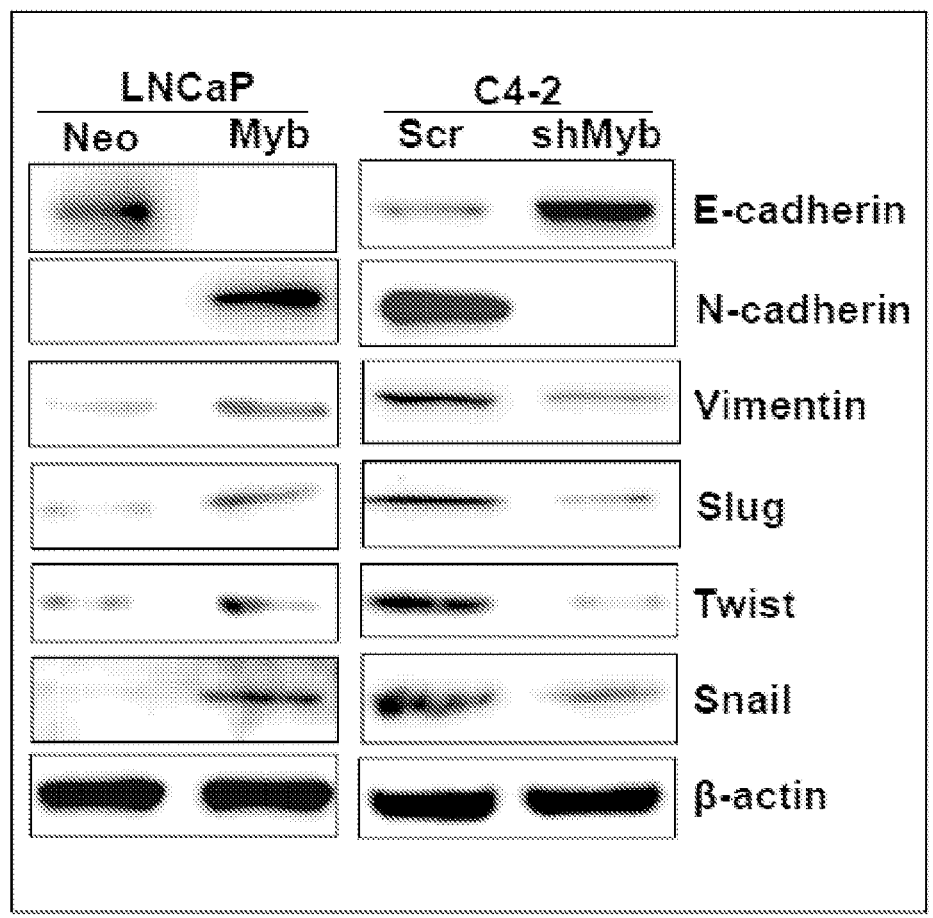

FIG. 7A and FIG. 7B show Myb overexpression induces epithelial to mesenchymal transition (EMT). FIG. 7A shows actin organization examined as a measure of EMT in Myb-overexpressing or -silenced prostate cancer cells. Cells were grown on glass coverslips, fixed and stained with Alexa Fluor 488-conjugated phalloidin. Cells were then analyzed and photographed using fluorescent microscope. Myb-overexpressing (LNCaP-Myb and C4-2-Scr) cells exhibited several filopodial and lamellipodia-like projections as compared to low Mybexpressing (LNCaP-Neo and C4-2-shMyb) cells. FIG. 7B shows expression profiles of various epithelial (E-cadherin) and mesenchymal (N-cadherin, Vimentin, Slug, Snail and Twist) examined in Myb-overexpressing or -silenced cells by immunoblot analyses. Myb overexpression was associated with loss of epithelial and gain of mesenchymal markers, indicating its role in EMT.

Figure 8:
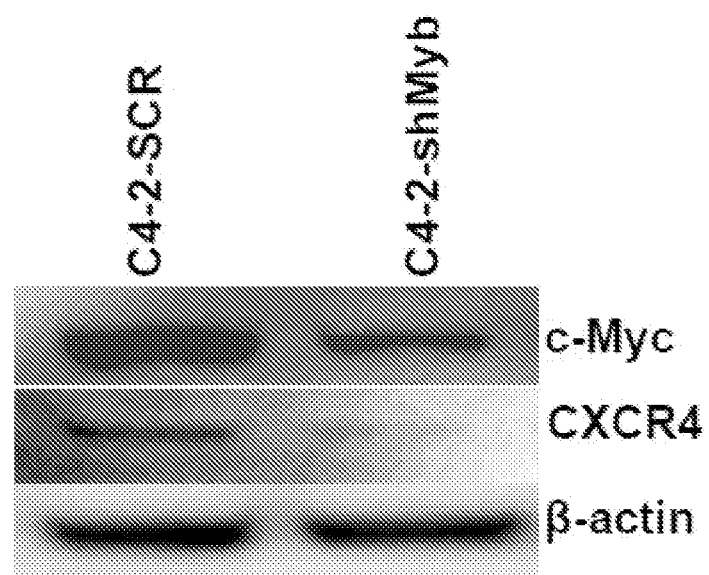

FIG. 8 shows the expression of c-Myc and CXCR4 in C4-2-SCR cells, and C4-2 shMyb cells.

Figure 9:
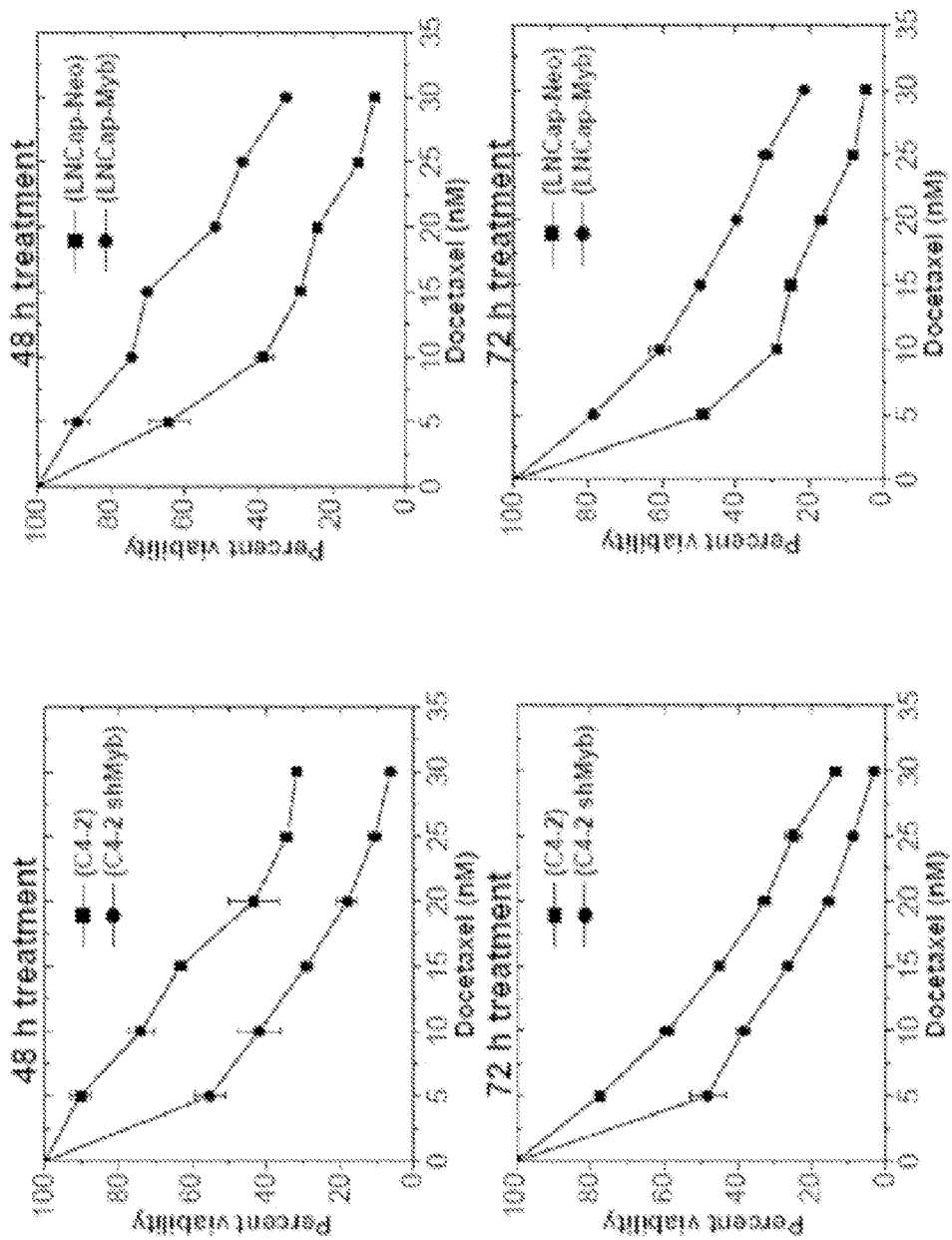

FIG. 9 shows the effect of increasing concentrations of Docetaxel on cell viability on C4-2, C4-2 shMyb, LNCaP-Neo, and LNCaP-Myb cells.

Figure 10:
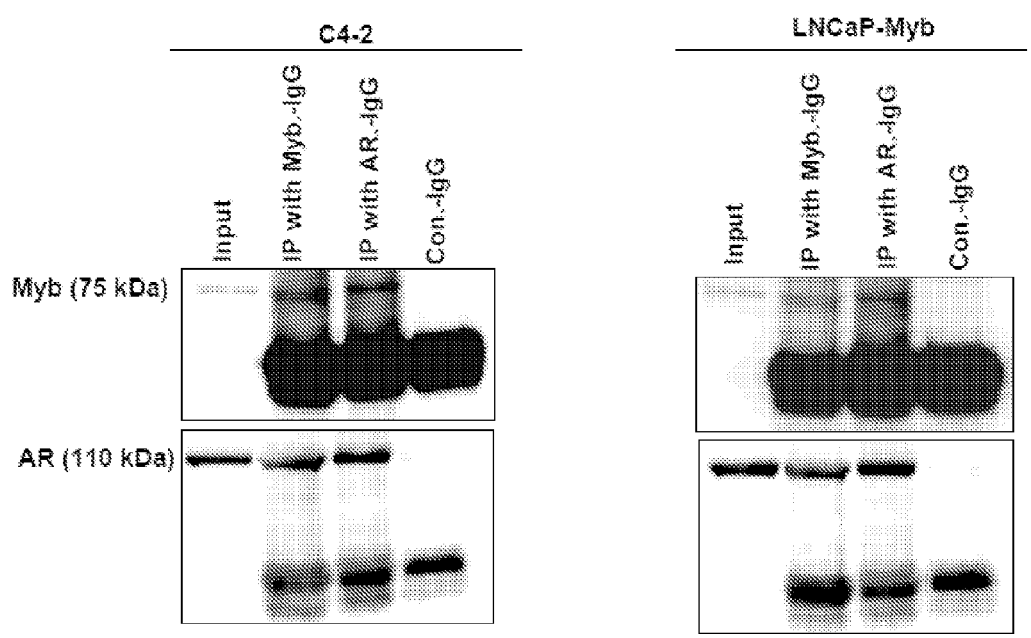

FIG. 10 shows the results of co-immunoprecipitation assays performed using C4-2 cells, and LNCaP-Myb cells with anti-Myb (rabbit monoclonal) and anti-AR (rabbit polyclonal) antibodies.

Figure 11A:
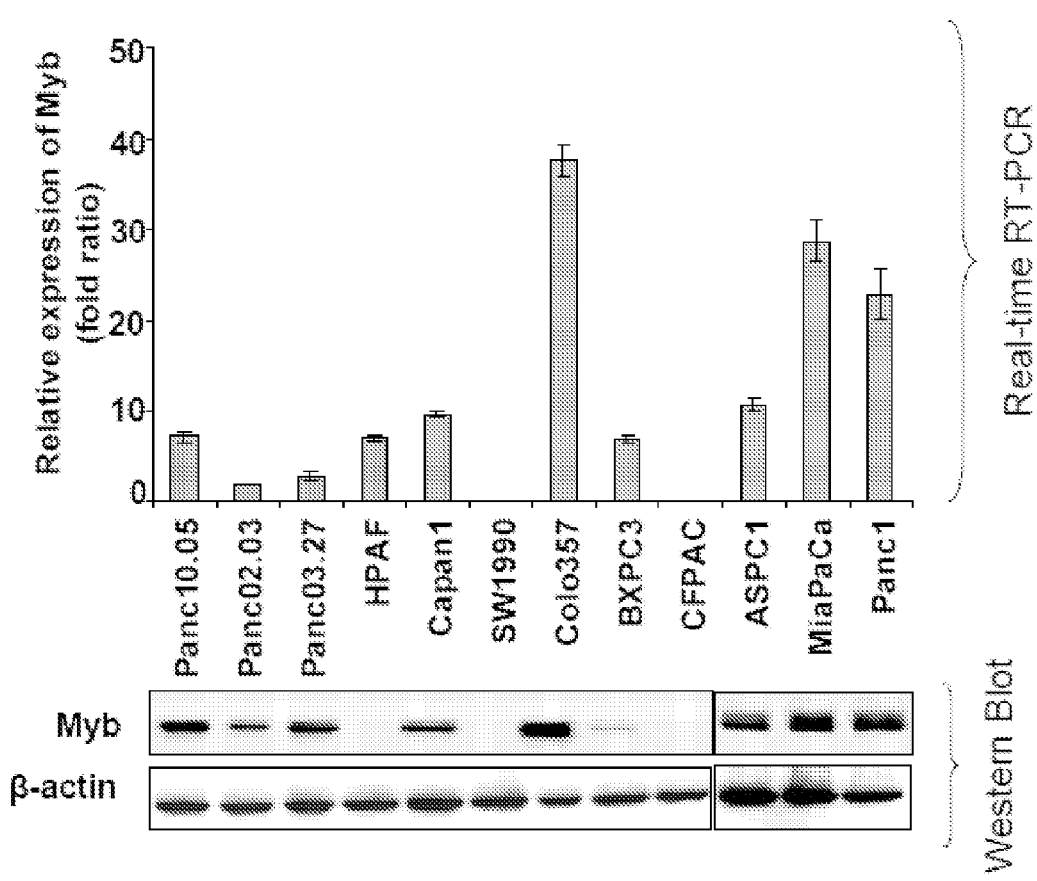
Figure 11B:
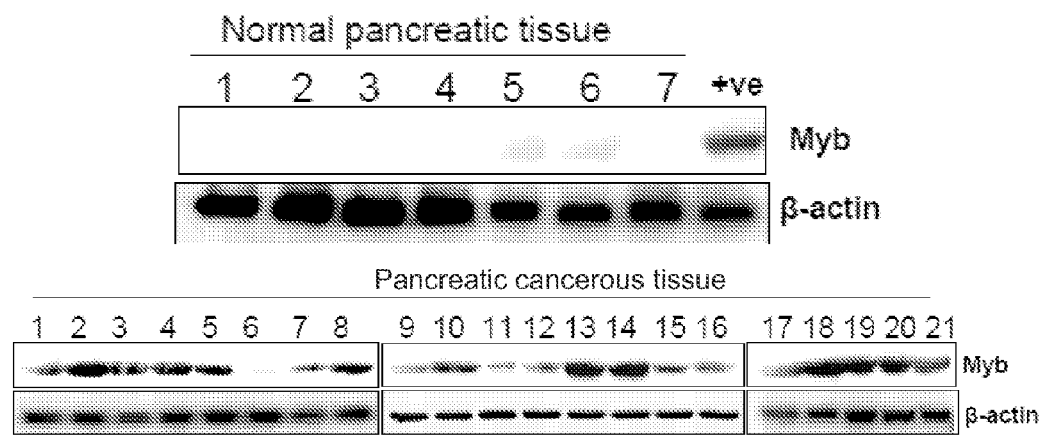
Figure 11C:
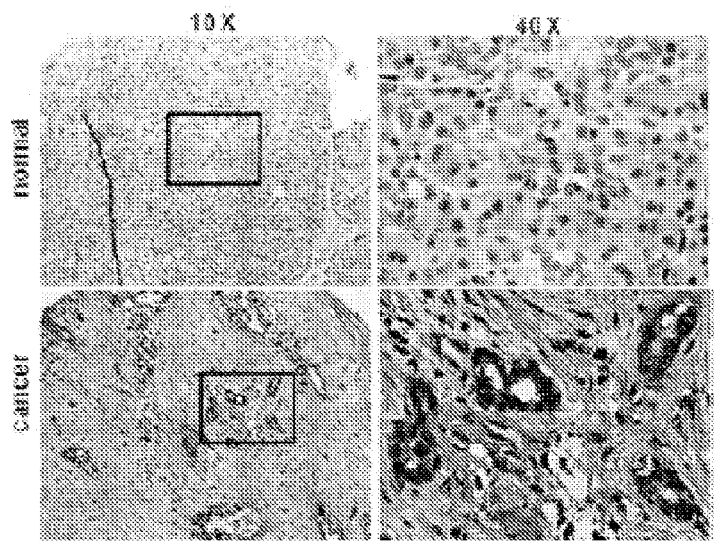

FIGS. 11A, 11B, 11C depict expression of Myb in pancreatic cancer cell lines. FIG. 11A shows a graph providing results from a real-time RT-PCR analysis. FIG. 11B shows a Western blot of normal and malignant tissues. FIG. 11C shows paraffin-embedded tissue sections on a pancreatic cancer test tissue-array.

Figure 12A:
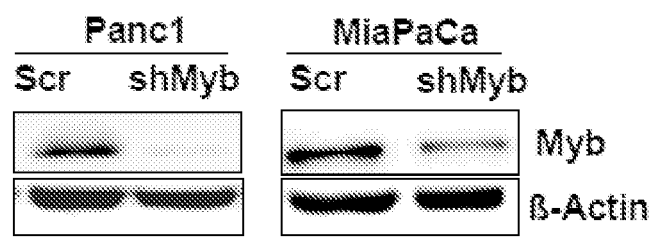
Figure 12B:
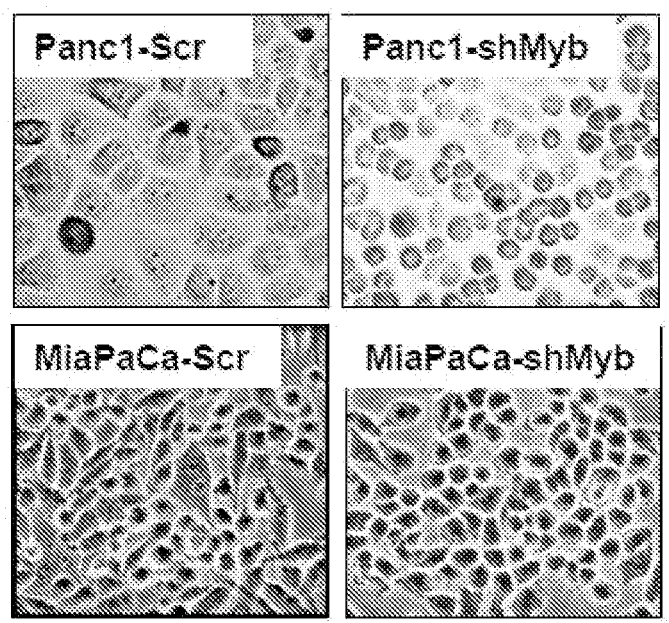
Figure 12C:
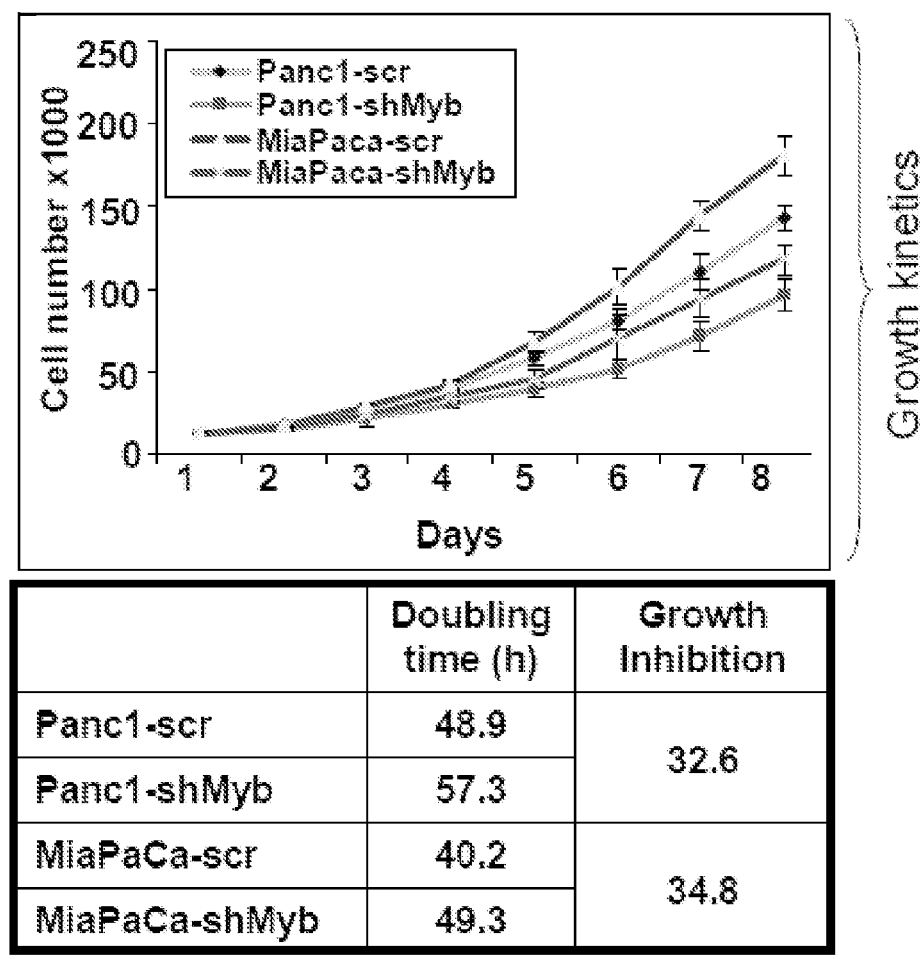

FIG. 12A shows an immunoblot assay in which stable Myb targeted shRNA-expressing or scrambled-shRNA-expressing populations (pooled) of Panc1 cells were generated and silencing of Myb expression was examined by immunoblot assay. Beta-actin was used as an internal control. FIG. 12B shows control and Myb-silenced Panc1 cells imaged under a light microscope (magnification ×100). FIG. 12C shows growth of Myb knockdown (Panc1-shMyb) and control (Panc1-Scr) cells was monitored (by cell counting) each day for 8 days to assess their growth kinetics.

Figure 13A:
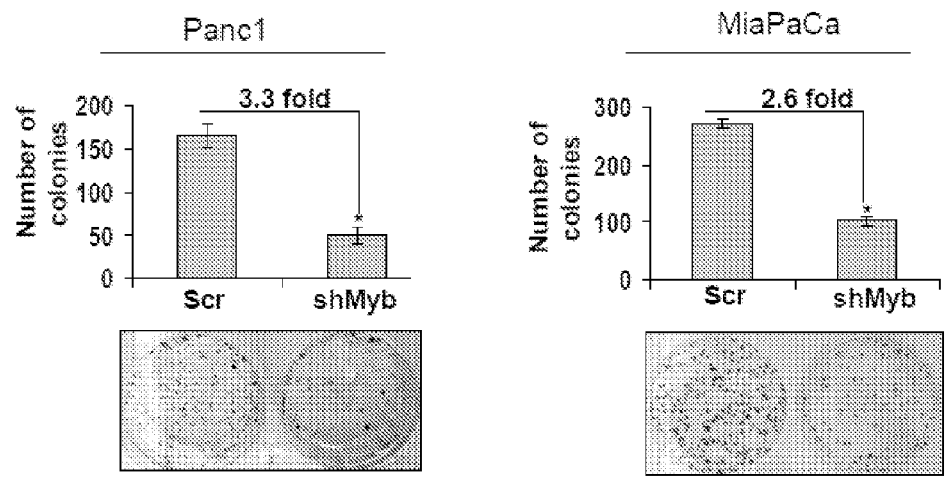
Figure 13B:
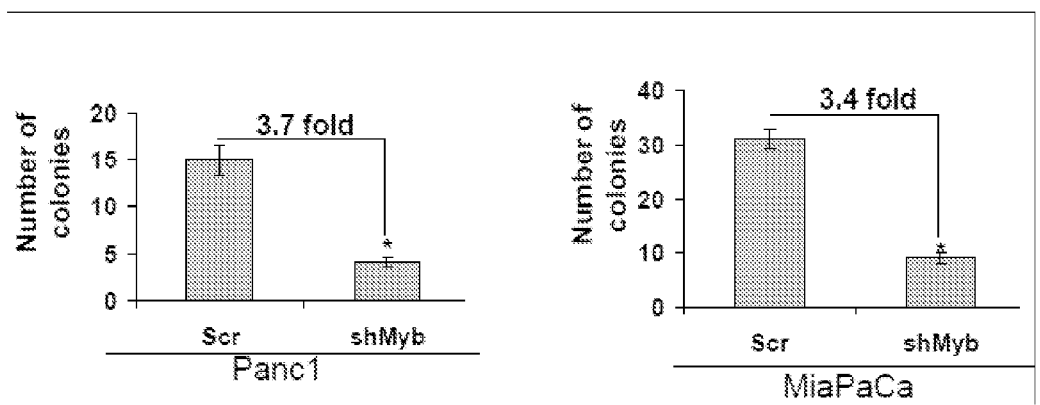

FIG. 13A depicts the results of an anchorage-dependent clonogenicity assay FIG. 13B depicts the results of an anchorage independent clonogenicity assay.

Figure 14A:
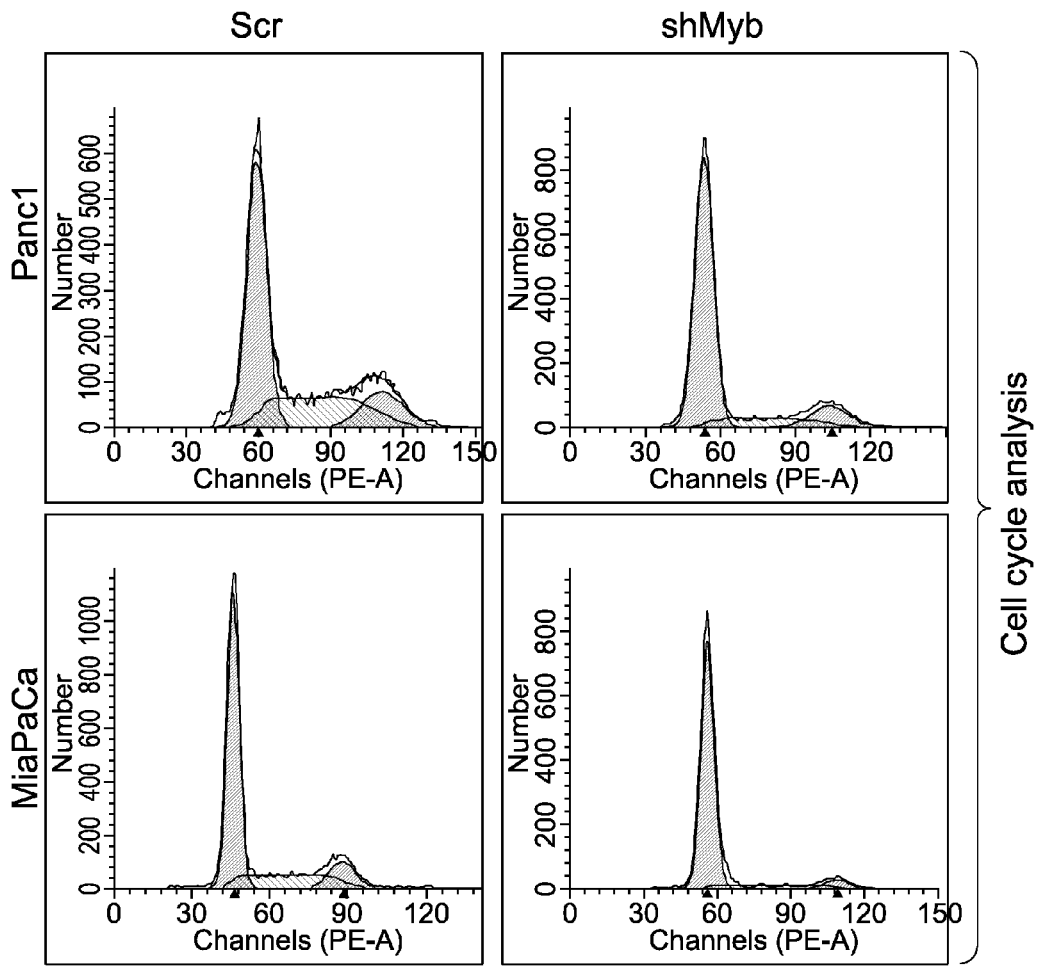
Figure 14B:
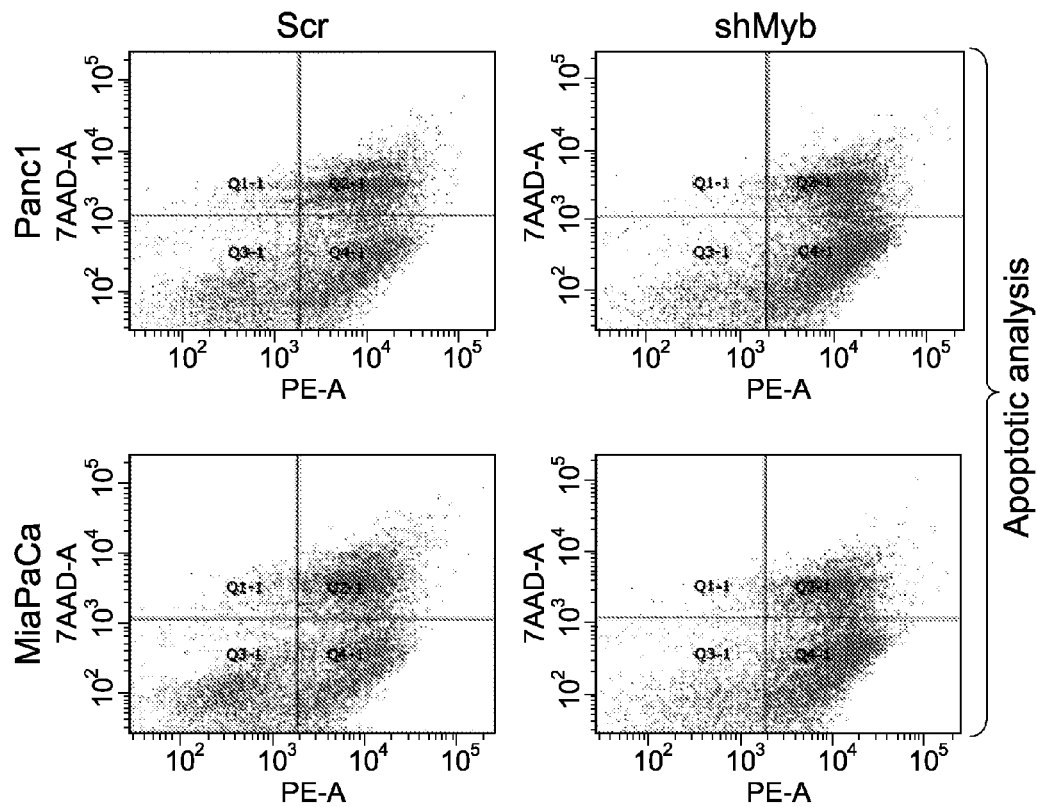

FIG. 14A depicts a cell cycle analysis in which Myb-silenced Panc1 & MiaPaCa cells along with their respective controls were synchronized, incubated in regular culture medium, and the distribution of cells in different phases of cell cycle analyzed FIG. 14B depicts an apoptosis assay in which control and Myb-silenced Panc1 & MiaPaCa cells were assessed for apoptosis.

Figure 15:
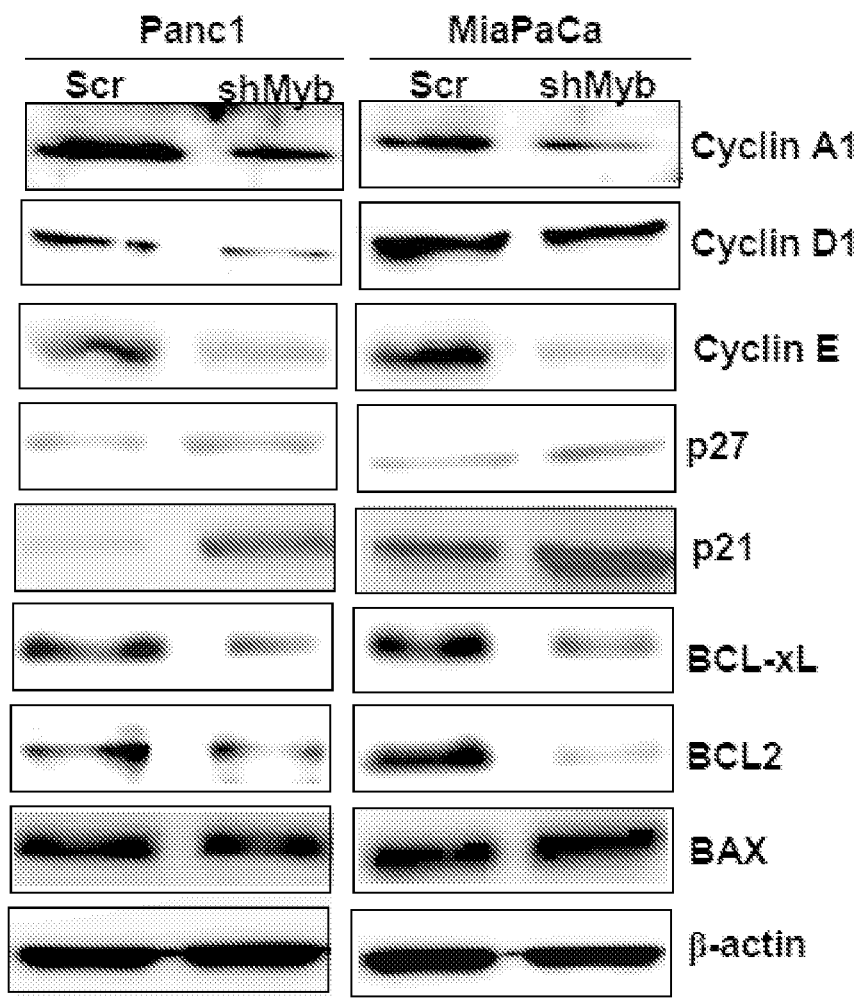

FIG. 15 shows a Western blot of Myb expression in Panc1 and MiaPaCa cells.

Figure 16:
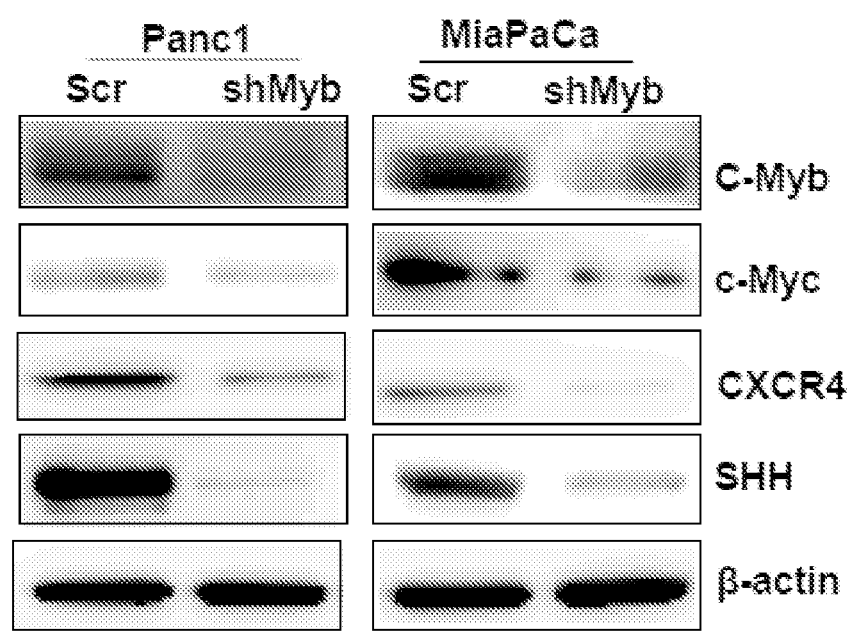

FIG. 16 shows a Western blot of Myb expression in Panc1 and MiaPaCa cells.

Figure 17A:
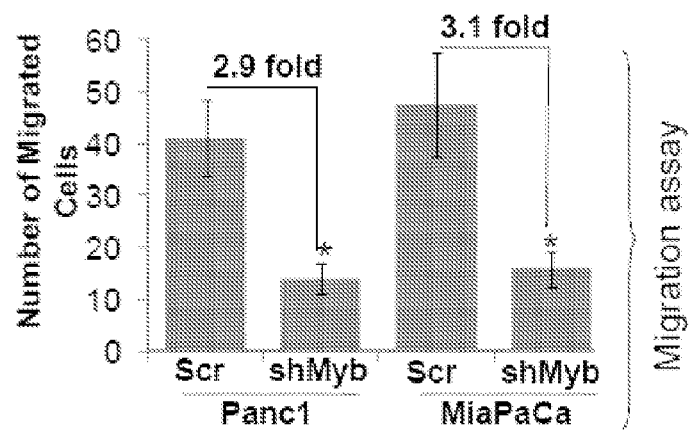
Figure 17B:
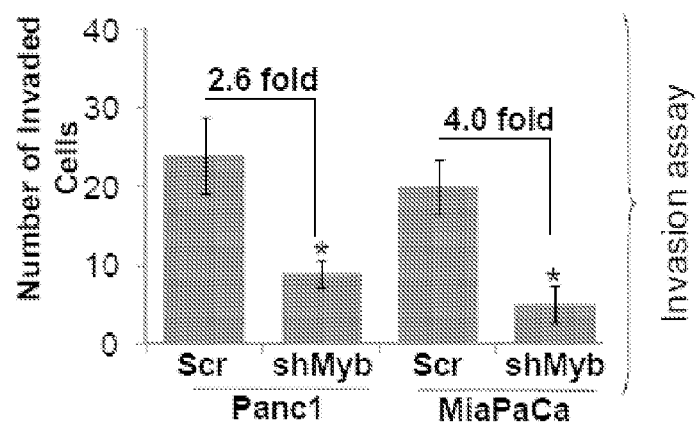
Figure 17C:
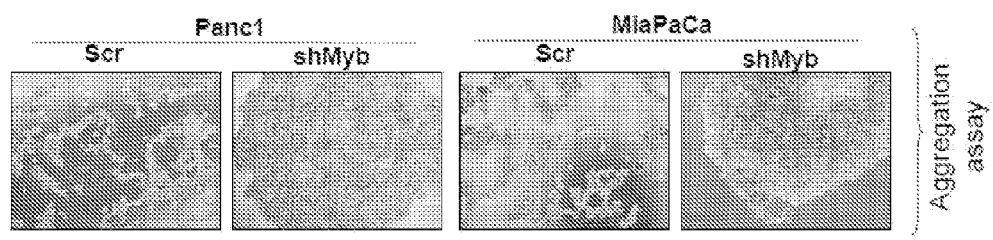

FIG. 17A shows a graph of the results from a migration assay. FIG. 17B shows a graph of the results from an invasion assay. FIG. 17C shows photomicrographs of the results of a hanging drop assay.

Figure 18A:
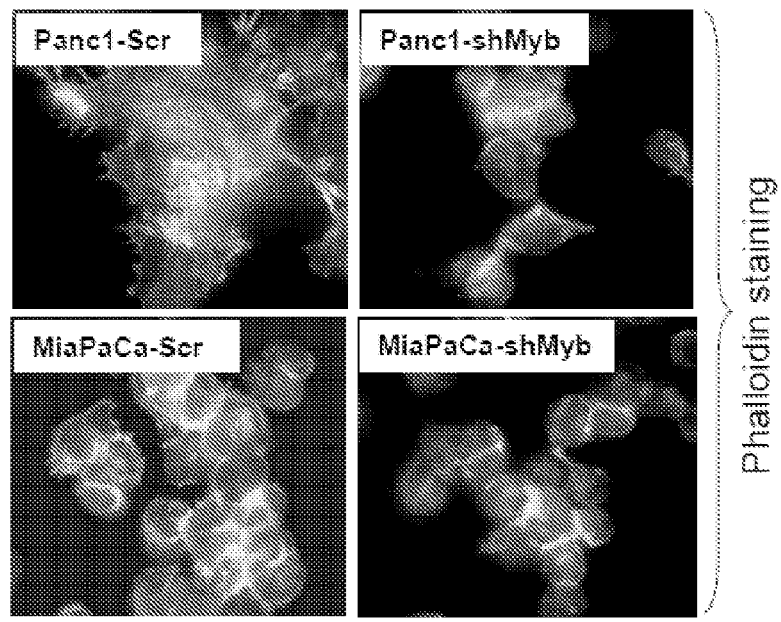
Figure 18B:
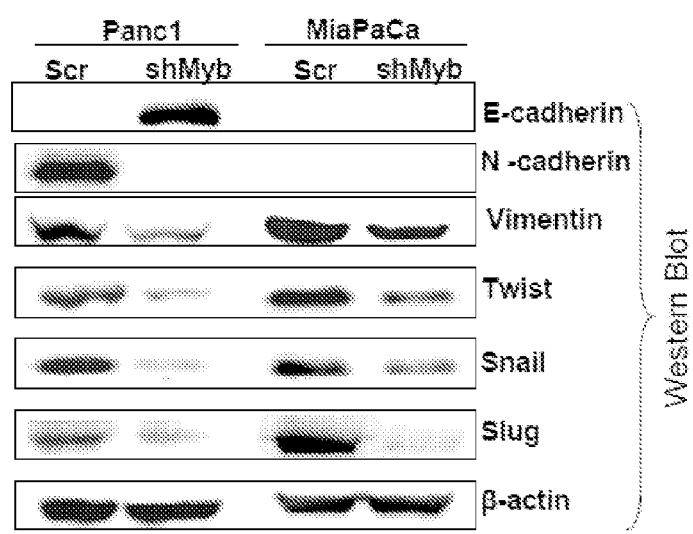

FIG. 18A shows photomicrographs of cells stained with Alexa Fluor 488-conjugated phalloidin. FIG. 18B shows a Western blot analysis of the Expression profiles of various epithelial (E-cadherin) and mesenchymal markers (N-cadherin, Vimentin, Slug, Snail and Twist) were examined in Myb-silenced and control cells.

Figure 19A:
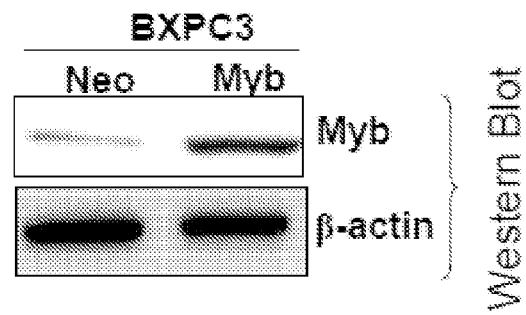
Figure 19B:
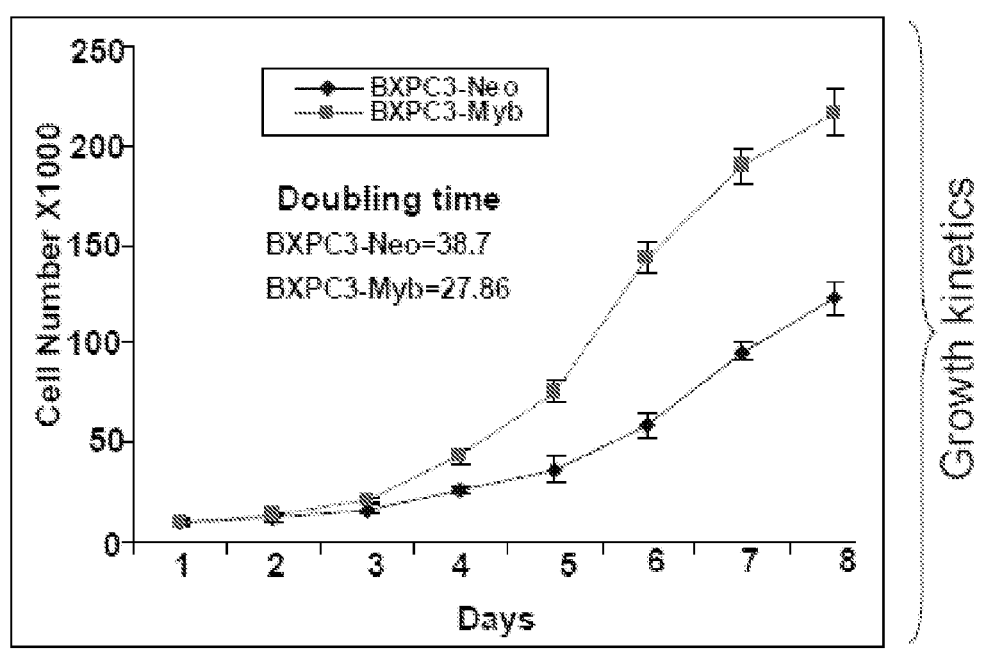

FIG. 19A shows a Western blot of Myb expression in BXPC3 cells. FIG. 19B shows a graph relating to the growth rate of BXPC3 cells.

Figure 20A:
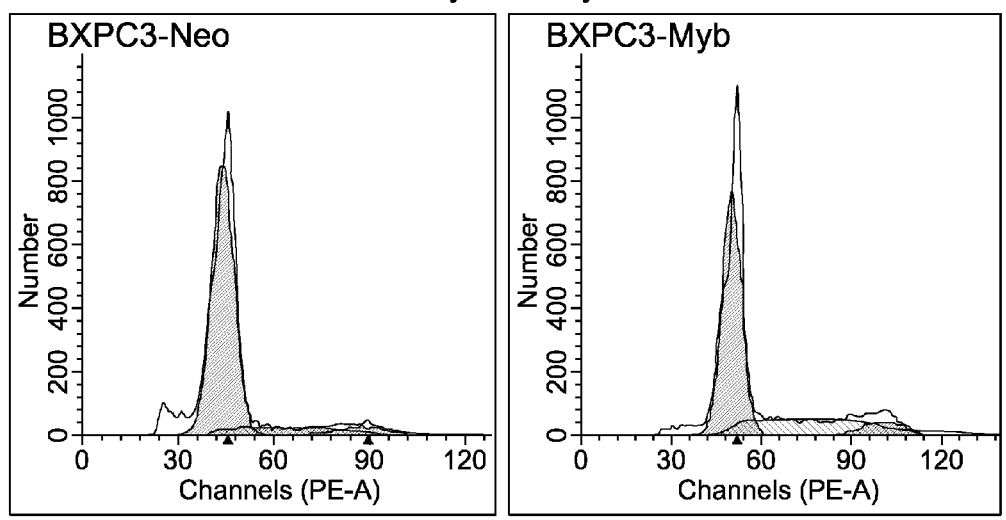
Figure 20B:
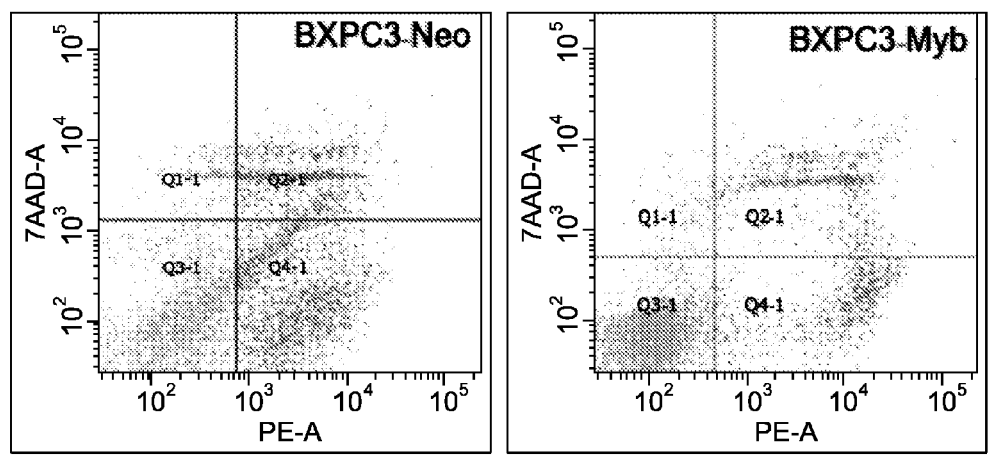

FIG. 20A depicts a cell cycle analysis of Myb overexpressing BXPC3 cells along with their respective controls in which the cells were synchronized then incubated in regular culture medium for 24 h, and the distribution of cells in different phases of cell cycle analyzed by propidium iodide (PI) staining and flow cytometry. FIG. 20B depicts an apoptosis assay in which control and Myb overexpressing BXPC3 cells were assessed for apoptosis.

Figure 21:
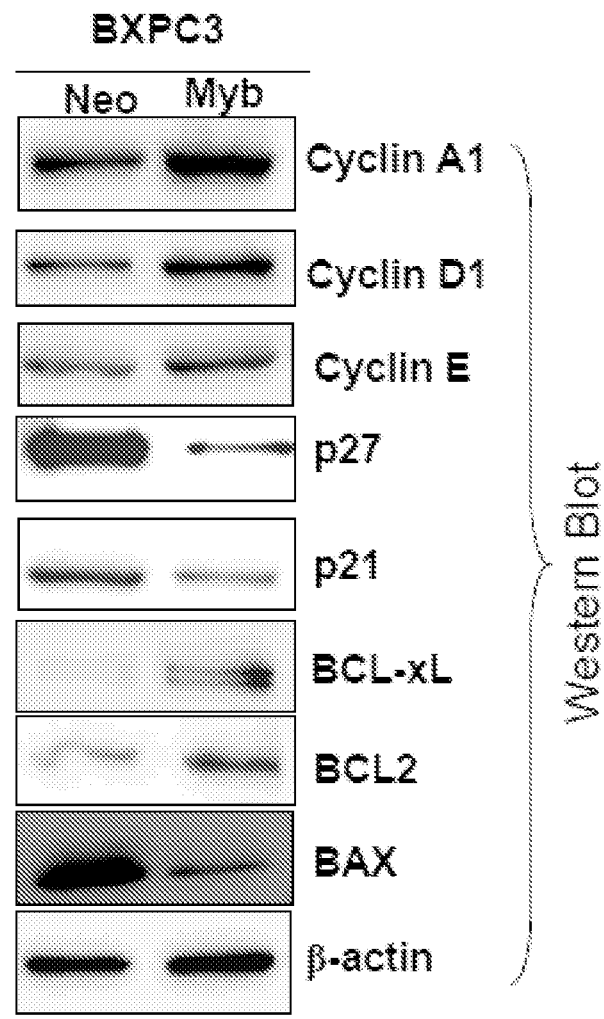

FIG. 21 shows a Western blot analysis of cell-cycle and survival-associated proteinsin BXPC3-Myb and BXPC3-Neo cells.

Figure 22A:
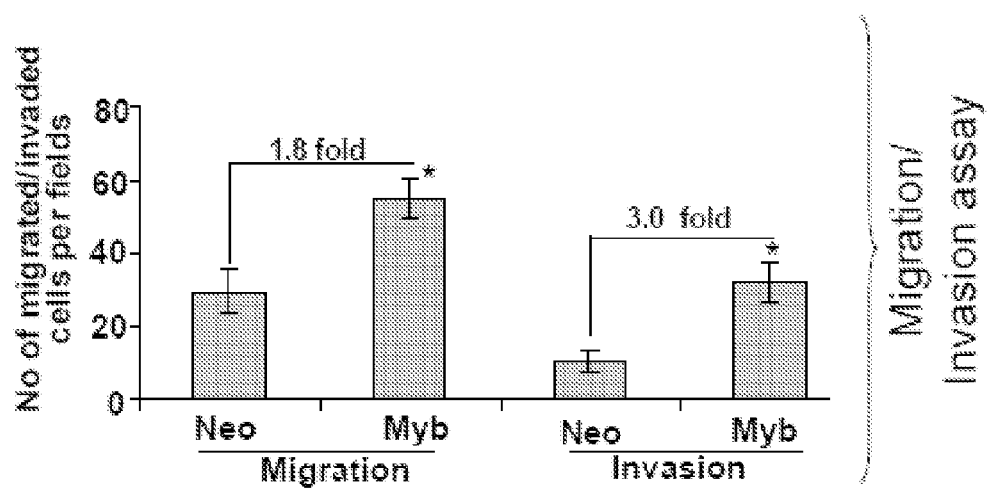
Figure 22B:
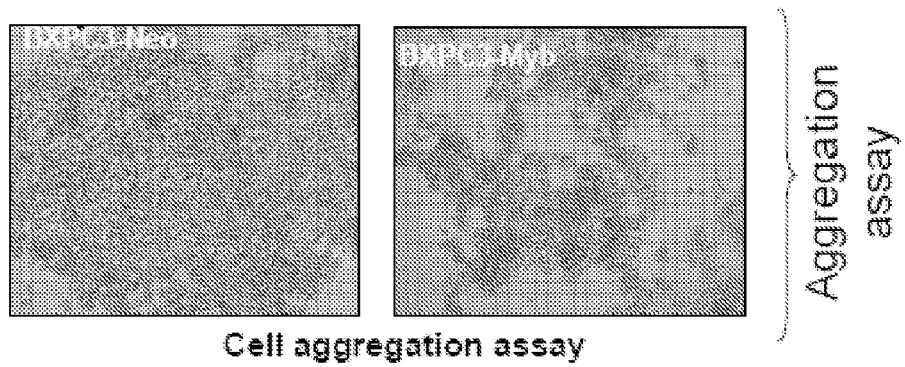

FIG. 22A shows graphs of a migration assay and an invasion assay. FIG. 22B shows photomicrographs of a cell aggregation assay.

Figure 23:
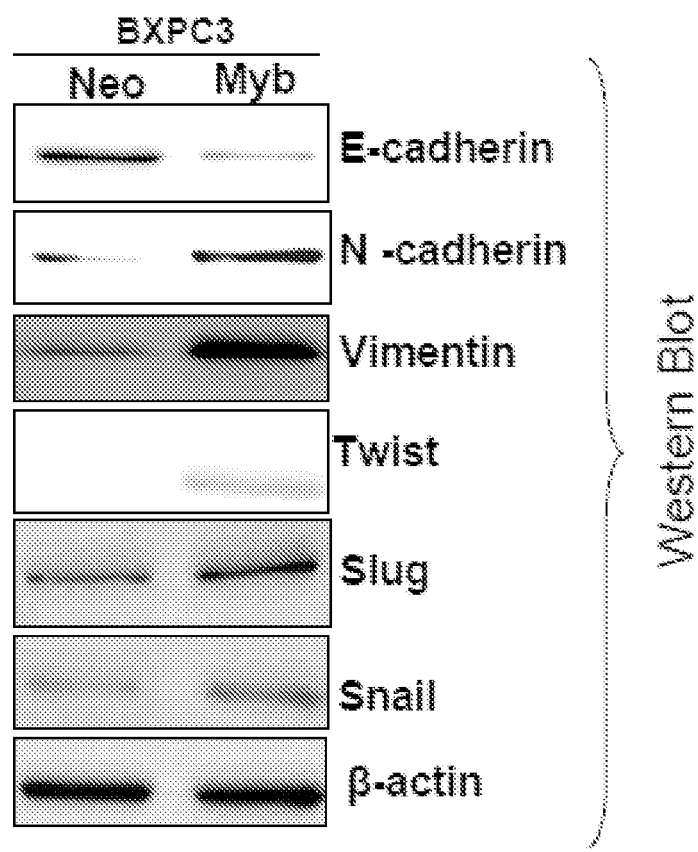

FIG. 23 shows a Western blot for the expression profiles of various epithelial (E-cadherin) and mesenchymal markers (N-cadherin, Vimentin, Slug, Snail and Twist) in BXPC3-Myb and BXPC3-Neo cells.

DETAILED DESCRIPTION

Some embodiments of the present technology relate to methods and compositions for the diagnosis and treatment of cancer. Some embodiments include methods and compositions for the diagnosis and treatment of hormone-refractory prostate cancer. Some embodiments include methods and compositions for the diagnosis and treatment of pancreatic cancer.

Myb is a transcription factor known to regulate the expression of several genes that play crucial roles during cellular proliferation, differentiation and survival (9). Its role has also been demonstrated in hematopoietic and some solid malignancies along with a recent report associating its amplification with hormone-refractory prostate cancer (8; 12-14). However, the contribution of Myb in the pathogenesis of cancers such as pancreatic cancer and prostate cancer has remained unexplored. The studies described herein demonstrate, for the first time, pathologically relevant functions of Myb in pancreatic cancer and prostate cancer. Some of the findings described herein strongly support the role of Myb overexpression in prostate cancer potentiating prostate cancer growth, castration-resistant progression and aggressive tumor phenotypes. This notion is based on (i) overexpression of Myb in prostate cancer cells with relatively greater expression in hormone-refractory cells, (ii) Myb-induced promotion of growth and clonogenicity of prostate cancer cells, (iii) Myb-supported androgen-independence and induction of PSA expression, (iv) enhanced tumor motility and invasion, and loss of homotypic interaction of Myb-overexpressing tumor cells, and (v) Myb-induced epithelial to mesenchymal transition. These findings underscore the significance of Myb as a novel molecular target in prostate cancer potentially controlling the progression to hormone therapy-resistant aggressive phenotypes.

Emergence of hormone-independent disease following androgen-deprivation therapy is a major clinical problem for the reason that the relapsed disease also does not respond well to alternative therapies (29). Therefore, characterization of Myb as a novel target promoting androgen-independence and aggressiveness of prostate cancer cells is highly significant. Multiple mechanisms have been proposed for castration-resistant progression of prostate cancer (7). The data presented herein provide a mechanism in which Myb overexpression promotes androgen-independence by sustaining cell cycle progression and preventing apoptosis under androgen-deprived condition. Importantly, the data also show an induced expression of PSA in Myb-overexpressing prostate cancer cells. This is of great significance, as PSA is an androgen-responsive gene and its serum levels are being used for prostate cancer screening and monitoring of the disease after androgen ablation therapy (27; 28). It is believed that relapse of PSA after androgen-deprivation therapy is due to reactivation of AR signaling through AR overexpression, mutations, altered expression of AR coregulators, intracrine signaling, etc. (5; 6; 33). Nonetheless, in other reports, additional AR-independent mechanisms of PSA upregulation have also been suggested (34; 35). As the data here shows no noticeable change in AR expression upon Myb modulation, Myb either induces PSA expression in an AR independent manner or sustain AR signaling through yet unidentified mechanisms. PSA promoter contains multiple Myb-binding sites, therefore, it is possible that Myb induces PSA expression through direct transcriptional upregulation. Alternatively, Myb may cooperate with AR to promote and sustain PSA expression under androgen-supplemented and -depleted conditions, respectively. In fact, it has been shown earlier that Myb cooperates with other transcription factors, such as C/EBP, Ets, CBF and PU.1 to regulate gene expression (36-38). Therefore, it will be of great interest to examine the combinatorial actions of Myb and AR in prostate cancer.

Normal cell growth is maintained and modulated by both proliferative and apoptotic signals and disruption of their balance contributes to the oncogenic process. It has been reported previously that androgen supports survival and proliferation of prostate cancer cells, and its ablation leads to cell-cycle arrest and induction of apoptosis (29; 39; 40). During the castration-resistant progression, prostate cancer cells are able to bypass these growth checkpoints due to overexpression of cyclins and/or anti-apoptotic proteins and/or loss of cell cycle inhibitors and/or pro-apoptotic proteins (2; 7). Data presented herein demonstrate that Myb overexpression induces the expression of cell cycle- and survival-associated proteins and is sufficient to sustain their levels under androgen depleted condition to support cell growth. In corroboration with these observations, it has been reported earlier that Myb upregulates the expression of cyclin A1 in myeloid leukemia cells (41). A reduced expression of cyclin E1 is also reported in Myb-mutant mouse strains causing a proliferation defect (42). A significant overexpression of Bcl-xL was also observed in Myb-overexpressing colon cancer cells correlating with enhanced tumorigenicity in mice xenograft model (43). Myb is also shown to promote the survival of CD4+CD8+ double-positive thymocytes through upregulation of Bcl-xL (44). In other studies, an association of Bcl-2 with Myb has also been reported in T-lymphocytes (45), and colon tissue (16), and cancer cells (23; 46).

Myb, a cellular progenitor of v-Myb oncogenes, was previously identified among the genes that are amplified at higher frequency in hormone-refractory prostate cancer. Applicant has investigated the functional role of Myb in prostate cancer. Using both gain- and loss-of function approaches, Applicant has discovered that Myb promotes growth and androgen-independence of prostate cancer cells, and confers aggressive phenotype by facilitating epithelial to mesenchymal transition (EMT).

Myb is one of several genes amplified at higher frequency in hormone-refractory prostate cancer (8). Myb, also referred as c-Myb, is the cellular progenitor of the v-Myb oncogenes carried by the chicken retroviruses AMV and E26 that cause acute myeloblastic leukemia or erythroblastosis (9). Myb encodes for a transcription factor, which activates gene expression in most cases by binding to the responsive promoter regions, the Myb binding sites. In some cases, activation by Myb can also occur independent of its DNA binding (10). Earlier reports suggested a restricted expression of Myb in the immature hematopoietic cells of all lineages, which decreased as the cells differentiated (11). Later on, Myb expression was also reported in other tissues as well as in hematological and other solid malignancies (12-15). Functional studies in hematopoietic cells have suggested that Myb plays a role in maintaining the undifferentiated proliferative state of immature cells (16). Myb-knockout mice died at embryonic stage and exhibited an essential loss of most blood cell lineages (17). Studies have shown that Myb activity is essential for continued proliferation and survival of acute and chronic myeloid leukemias (AML and CML) (18; 19) and reduced Myb levels can, in fact, impair the transformation by other leukaemogenic oncogenes (18; 20). Myb confers its oncogenic activity by regulating the expression of a wide array of target genes and a pathogenic role of Myb has also been suggested in melanoma, head and neck, breast and colon cancers (21-23).

Some of the studies provided herein show Myb expression in all prostate cancer cell lines (LNCaP, C4-2, PC3 and DU145) examined, whereas Myb was negligibly expressed in normal/benign prostate epithelial cells (RWPE1 and RWPE2). Notably, Myb was significantly upregulated, both at transcript (>60-fold) and protein (>15-fold) levels, in castration-resistant (C4-2) cells as compared to androgen-dependent (LNCaP) prostate cancer cells of the same genotypic lineage. Using loss- and gain-of function approaches, a role of Myb in androgen-independence of prostate cancer cells was demonstrated. Myb promoted and sustained cell cycle progression and survival under androgen-supplemented and -deprived conditions, respectively, through induction of cyclins (A1, D1, and E1), Bcl-xL and Bcl2, and downregulation of p27 and Bax. Interestingly, Myb overexpression was also associated with enhanced prostate-specific antigen (PSA) expression. The data provided herein shows that Myb potentiated motility and invasion, and decreased homotypic interactions of prostate cancer cells. Myb overexpression was also associated with actin reorganization leading to the formation of filopodia-like cellular protrusions. Immunoblot analyses demonstrated gain of mesenchymal and loss of epithelial markers, and vice versa, in Myb-overexpressing LNCaP, and -silenced C4-2 cells, respectively, indicating a role of Myb in epithelial to mesenchymal transition. Altogether, the studies described herein provide the first experimental evidence for a functional role of Myb in growth, malignant behavior and androgen independence of prostate cancer cells.

Methods for Evaluating the Presence or Stage of a Cancer

Some methods and compositions provided herein relate to evaluating the presence or stage of a cancer, such as pancreatic cancer and prostate cancer, such as castration-resistant prostate cancer. In some embodiments, castration-resistant prostate cancer includes hormone-refractory prostate cancer. In some embodiments, castration-resistant prostate cancer includes cells that are androgen-independent. In some embodiments, castration-resistant prostate cancer includes cells that may produce androgens and in which androgen-receptor signaling is active, for example, in an intracrine manner. In some embodiments, the stage of cancer or metastatic potential of a cancer is assessed by measuring the level of a nucleic acid encoding c-Myb or fragment thereof, such as an mRNA encoding c-Myb, or the level of c-Myb protein or fragment thereof or the activity of c-Myb protein in a biological sample. A fragment of a polynucleotide sequence will be understood to include any nucleotide fragment having, for example, at least about 5 successive nucleotides, at least about 12 successive nucleotides, at least about 15 successive nucleotides, at least about 18 successive nucleotides, or at least about 20 successive nucleotides of the sequence from which it is derived. An upper limit for a fragment can include, for example, the total number of nucleotides in a full-length sequence encoding a particular polypeptide. A fragment of a polypeptide sequence will be understood to include any polypeptide fragment having, for example, at least about 5 successive residues, at least about 12 successive residues, at least about 15 successive residues, at least about 18 successive residues, or at least about 20 successive residues of the sequence from which it is derived. An upper limit for a fragment can include, for example, the total number of residues in a full-length sequence of a particular polypeptide.

In some embodiments, the level of nucleic acid encoding c-Myb, such as an mRNA encoding c-Myb, or the level of c-Myb protein or the activity of c-Myb protein in a biological sample is compared to that of a control sample indicative of non-cancerous tissues, or a particular stage of cancer. Alternatively, the level of nucleic acid encoding c-Myb, such as an mRNA encoding c-Myb, or the level of c-Myb protein or the activity of c-Myb protein in a biological sample may be compared to the level of nucleic acid encoding c-Myb, such as an mRNA encoding c-Myb, or the level of c-Myb protein or the activity of c-Myb protein known to be indicative of cancer or a particular stage of cancer, or to a level known to be indicative of non-cancerous tissue. Some embodiments include removing a sample from a subject's body. For example, in some embodiments, measuring and comparing can be done ex vivo. In some embodiments an increased level of a nucleic acid encoding c-Myb, such as an mRNA encoding c-Myb, or increased level of c-Myb protein or increased activity of c-Myb protein in a sample is indicative of the presence of a cancer, such as pancreatic cancer or prostate cancer. In some embodiments an increased level of a nucleic acid encoding c-Myb, such as an mRNA encoding c-Myb, or increased level of c-Myb protein or increased activity of c-Myb protein in a sample is indicative of a hormone-refractory cancer, such as hormone-refractory prostate cancer.

In some embodiments, an increase in the level of a nucleic acid encoding c-Myb, such as an mRNA encoding c-Myb, or an increase in c-Myb protein or an increase in activity of c-Myb protein in a test sample compared to the level of a nucleic acid encoding c-Myb, such as an mRNA encoding c-Myb, or c-Myb protein or the activity of c-Myb protein in a non-cancer control sample or a level known to be indicative of normal non-cancerous tissue of at least about 2-fold greater, about 3-fold greater, about 5-fold greater, about 10-fold greater, about 20-fold greater, about 30-fold greater, about 40-fold greater, about 50-fold greater, about 60-fold greater, about 70-fold greater, about 80-fold greater, about 90-fold greater, or more, is indicative of the presence of a cancer, or the stage of a cancer. In some such embodiments, the increase is indicative of the presence of pancreatic cancer. In some such embodiments, the increase is indicative of the presence of prostate cancer, for example, hormone-refractory prostate cancer. As used herein, a hormone-refractory cancer includes castration-resistant cells.

In some embodiments, the level of a nucleic acid encoding a marker or level of a protein marker in addition to the level of a nucleic acid encoding c-Myb, such as an mRNA encoding c-Myb, or the level of c-Mybprotein, or the activity of c-Myb protein is measured. Examples of additional markers include prostate specific antigen (PSA), cyclin A1, cyclin D1, cyclin E1, Bcl-xL, Bcl2, N-cadherin, vimentin, slug, snail, twist, p27/KIP1, p21/WAF1, Bax, and CXCR4. Some embodiments include measuring the expression level of a nucleic acid encoding at least one marker or the expression level of at least one marker protein in addition to the expression level of said nucleic acid encoding c-Myb, such as an mRNA encoding c-Myb, or the expression level of said c-Myb protein in said sample. In some such embodiments, the levels of at least 2 additional markers, at least 3 additional markers, at least 4 additional markers, at least 5 additional markers, at least 6 additional markers, at least 7 additional markers, at least 8 additional markers, at least 9 additional markers, and at least 10 additional markers, are measured.

In addition to measuring the level of a nucleic acid encoding c-Myb, such as an mRNA encoding c-Myb or the level of c-Myb protein or the activity of c-Myb protein in sample, some embodiments further include comparing the expression level of a nucleic acid encoding at least one marker or the expression level of at least one marker protein in a sample to the expression level of a nucleic acid encoding at least one marker or the expression level of at least one marker protein in normal tissue, or tissue from a known stage of cancer. In some embodiments, an increased level of expression of a nucleic acid encoding at least one marker or at least one marker protein such as a marker including PSA, cyclin A1, cyclin D1, cyclin E1, Bcl-xL, Bcl2, N-cadherin, vimentin, slug, snail, and twist in conjunction with an increased level of a nucleic acid encoding c-Myb, such as an mRNA encoding c-Myb or an increased level in c-Myb protein or increased activity of c-Myb protein, indicates the presence or stage of a cancer, such as pancreatic cancer or prostate cancer, such as castration-resistant prostate cancer. In some embodiments a decreased level of expression of a nucleic acid encoding at least one marker or at least one marker protein, such as a marker including p27/KIP1, p21/WAF1, Bax, and CXCR4, indicates the presence or stage of a cancer.

A biological sample can be any sample suitable for measuring the level of a nucleic acid encoding c-Myb, such as an mRNA encoding c-Myb, or for measuring c-Myb protein or the activity of c-Myb protein. For example, the biological sample can include blood, sera, sputum urine and tumor biopsies, including epithelial cells, pancreatic cancer cells and prostate cancer cells obtained from a patient.

Expression levels can be measured by various methods, such as levels of mRNA, levels of protein, and levels of biological activity of a protein or mRNA. Polynucleotide primers and probes may be used to detect the level of mRNA encoding c-Myb or an additional marker protein, which is also indicative of the presence or stage of a cancer. In general, a nucleic acid encoding c-Myb or an additional marker sequence may be present at a level that is increased or decreased at least two-fold, preferably three-fold, and more in tumor tissue than in normal tissue of the same type from which the tumor arose. Expression levels of a particular marker sequence in tissue types different from that in which the tumor arose are irrelevant in certain diagnostic embodiments since the presence of tumor cells can be confirmed by observation of predetermined differential expression levels, e.g., about 2-fold, 5-fold, etc, in tumor tissue to expression levels in normal tissue of the same type.

In some embodiments, in conjunction with an increase in the level of a nucleic acid encoding c-Myb or the level of c-Myb protein or the activity of c-Myb protein, a decrease in the levels of expression of a marker or nucleic acid encoding a marker, such as p27/KIP1, p21/WAF1, Bax, and CXCR4, in a sample relative to expression levels in normal tissue, or tissue from less advanced stages of cancer, can indicate the stage or metastatic potential of a cancer, such as pancreatic cancer or prostate cancer, such as castration-resistant prostate cancer. In such embodiments, the decrease in the level of expression of a marker protein or nucleic acid encoding a marker protein can be about 2-fold, 5-fold, 10-fold, 100-fold, or more. In some embodiments, in conjunction with an increase in the level of a nucleic acid encoding c-Myb or the level of c-Myb protein or the activity of c-Myb protein, an increase in the level of expression in a sample of a marker protein or a nucleic acid encoding a marker protein such as PSA cyclin A1, cyclin D1, cyclin E1, Bcl-xL, Bcl2, N-cadherin, vimentin, slug, snail, and twist, relative to expression levels in normal tissue, or tissue from less advanced stages of cancer, can indicate the stage or metastatic potential of a cancer, such as pancreatic cancer or prostate cancer, such as castration-resistant prostate cancer. In such embodiments, the increase in the level of expression of a marker protein or nucleic acid encoding a marker protein can be about 2-fold, 5-fold, 10-fold, 100-fold, or more.

Protein levels in a sample may be measured by a variety of methods. There are a variety of assay formats known to those of ordinary skill in the art for using a binding agent to detect polypeptide markers in a sample. See, e.g., Harlow and Lane, Antibodies: A Laboratory Manual, Cold Spring Harbor Laboratory, 1988. For example, the level of a protein may be determined by (a) contacting a biological sample obtained from a subject with a binding agent; (b) detecting in the sample a level of polypeptide that binds to the binding agent; and (c) comparing the level of polypeptide with a predetermined cut-off value.

In some embodiments, an assay includes the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. In such embodiments, the binding agent can comprise an antibody or fragment thereof specific to c-Myb or other marker described herein. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length c-Myb proteins and polypeptide portions thereof to which the binding agent binds, for example the c-Myb protein or additional markers described herein.

The solid support may be any material known to those of ordinary skill in the art to which the binding agent may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 µg, and preferably about 100 ng to about 1 µg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12-A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art may be used, such as bovine serum albumin or TWEEN 20. (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with breast cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% TWEEN 20. The second antibody, which contains a reporter group, may then be added to the solid support. Reporter groups are well known in the art. The detection reagent is then incubated with the immobilized antibody-polypeptide complex for an amount of time sufficient to detect the bound detection reagent. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the level of a marker such as c-Myb protein or an additional protein marker described herein, the signal detected from the reporter group that remains bound to the solid support is generally compared to a signal that corresponds to a predetermined cut-off value. In one embodiment, the cut-off value for the detection of a cancer is the average mean signal obtained when the immobilized antibody is incubated with samples from patients without the cancer. In general, a sample generating a signal that is three standard deviations above or below the predetermined cut-off value is considered positive for the cancer. For example, an increased level of c-Myb protein or an additional marker upregulated by c-Myb may be indicative of the presence of cancer or the stage of cancer. Similarly, a reduced level of c-Myb protein or an additional marker downregulated by c-Myb may be indicative of the presence of cancer or the stage of cancer. In some embodiments, the cut-off value is determined using a Receiver Operator Curve, according to the method of Sackett et al., Clinical Epidemiology: A Basic Science for Clinical Medicine, Little Brown and Co., 1985, p. 106-7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described herein. In the strip test format, one end of the membrane to which binding agent is bound is immersed in a solution containing the sample. The sample migrates along the membrane through a region containing second binding agent and to the area of immobilized binding agent. The amount of immobilized antibody indicates the presence, or stage of a cancer. Typically, the concentration of second binding agent at that site generates a pattern, such as a line, that can be read visually. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 µg, and more preferably from about 50 ng to about 500 ng. Such tests can typically be performed with a very small amount of biological sample.

Methods to determine the presence and/or level of a nucleic acid in a sample are well known in the art. Examples include PCR, quantative methods of PCR, such as real time PCR, and Northern blot analysis. Techniques for both PCR based assays and hybridization assays are well known in the art (see, for example, Mullis et al., Cold Spring Harbor Symp. Quant. Biol., 51:263, 1987; Erlich ed., PCR Technology, Stockton Press, NY, 1989).

In some embodiments, the methods and compositions described herein may be used to identify the progression of cancer, such as pancreatic cancer or prostate cancer, such as castration-resistant prostate cancer. In such embodiments, assays as described herein for the diagnosis of a cancer may be performed over time, and the change in the level of reactive polypeptide(s) or polynucleotide(s) evaluated. For example, the assays may be performed every month for a period of 6 months to 1 year, and thereafter performed as needed. In general, a cancer is progressing in those patients in whom the level of polypeptide or polynucleotide detected changes over time. For example, a cancer, such as pancreatic cancer or prostate cancer may be progressing where levels of expression of markers such as p27/KIP1, p21/WAF1, Bax, and CXCR4 are decreasing, and/or levels of expression of markers such as PSA, cyclin A1, cyclin D1, cyclin E1, Bcl-xL, Bcl2, N-cadherin, vimentin, slug, snail, and twist are increasing. In some embodiments, the level of expression of a marker can be used to determine the progression of a cancer, such as pancreatic cancer or prostate cancer, such as castration-resistant prostate cancer.

Certain in vivo diagnostic assays may be performed directly on a tumor. One such assay involves contacting tumor cells with a binding agent, for example, an isolated antibody or fragment thereof, specific for c-Myb. The bound binding agent may then be detected directly or indirectly via a reporter group. Such binding agents may also be used in histological applications. Alternatively, polynucleotide probes may be used within such applications.

Multiple markers may be assayed within a given sample. It will be apparent that binding agents specific for different markers provided herein may be combined within a single assay. Further, multiple primers or probes may be used concurrently. The selection of markers may be based on routine experiments to determine combinations that results in optimal sensitivity. In addition, or alternatively, assays for tumor proteins provided herein may be combined with assays for other known tumor antigens.

Methods and Compositions to Reduce Levels of c-Myb

Some embodiments relate to compositions and/or methods for reducing activity of the pathways that include c-Myb. In some embodiments, the level of c-Myb protein or the level of a nucleic encoding c-Myb or the activity of c-Myb protein can be reduced in the cell of a subject. Methods to reduce the level of c-Myb protein or the level of a nucleic encoding c-Myb or the activity of c-Myb protein in a cell or a subject can be useful to kill or retard the growth of a cell, to treat or ameliorate certain disorders in a subject, to increase the sensitivity of a cell to therapeutic agents, or to reduce the dosage of a therapeutic agent required to treat a disorder in a subject.

In some embodiments, the methods or compositions described herein result in a decrease of the amounts of c-Myb protein or a nucleic acid encoding c-Myb, such as endogenous c-Myb, or an mRNA encoding c-Myb, or the activity of c-Myb protein within a cell. In some embodiments, the methods or compositions described herein provide a decrease in c-Myb protein or a decrease in a nucleic acid encoding c-Myb or the activity of c-Myb protein within a cell of at least about 10%, at least about 20%, at least about 30%, at least about 40%, at least about 50%, at least about 60%, at least about 70%, at least about 80%, at least about 90%, and at least about 100%.

The level of c-Myb protein or the level of a nucleic encoding c-Myb or the activity of c-Myb protein can be reduced using RNA interference or antisense technologies. RNA interference is an efficient process whereby double-stranded RNA (dsRNA), also referred to herein as siRNAs (small interfering RNAs) or ds siRNAs (double-stranded small interfering RNAs), induces the sequence-specific degradation of targeted mRNA in animal or plant cells (Hutvagner, G. et al. (2002) Curr. Opin. Genet. Dev. 12:225-232); Sharp, P. A. (2001) Genes Dev. 15:485-490).

In mammalian cells, RNA interference can be triggered by various molecules, including 21-nucleotide duplexes of siRNA (Chiu, Y.-L. et al. (2002) Mol. Cell. 10:549-561. Clackson, T. et al. (1991) Nature 352:624-628; Elbashir, S. M. et al. (2001) Nature 411:494-498), or by micro-RNAs (miRNA), functional small-hairpin RNA (shRNA), or other dsRNAs which can be expressed in vivo using DNA templates with RNA polymerase III promoters (Zheng, B. J. (2004) Antivir. Ther. 9:365-374; Paddison, P. J. et al. (2002) Genes Dev. 16:948-958; Lee, N. S. et al. (2002) Nature Biotechnol. 20:500-505; Paul, C. P. et al. (2002) Nature Biotechnol. 20:505-508; Tuschl, T. (2002) Nature Biotechnol. 20:446-448; Yu, J.-Y. et al. (2002) Proc. Natl. Acad. Sci. USA 99(9):6047-6052; McManus, M. T. et al. (2002) RNA 8:842-850; Sui, G. et al. (2002) Proc. Natl. Acad. Sci. USA 99(6):5515-5520, each of which are incorporated herein by reference in their entirety).

The scientific literature is replete with reports of endogenous and exogenous gene expression silencing using siRNA, highlighting their therapeutic potential (Gupta, S. et al. (2004) PNAS 101:1927-1932; Takaku, H. (2004) Antivir Chem. Chemother 15:57-65; Pardridge, W. M. (2004) Expert Opin. Biol. Ther. 4(7):1103-1113; Shen, W.-G. (2004) Chin. Med. J. (Engl) 117:1084-1091; Fuchs, U. et al. (2004) Curr. Mol. Med. 4:507-517; Wadhwa, R. et al. (2004) Mutat. Res. 567:71-84; Ichim, T. E. et al. (2004) Am. J. Transplant 4:1227-1236; Jana, S. et al. (2004) Appl. Microbiol. Biotechnol. 65:649-657; Ryther, R. C. C. et al. (2005) Gene Ther. 12:5-11; Chae, S-S. et al. (2004) J. Clin. Invest 114:1082-1089; de Fougerolles, A. et al. (2005) Methods Enzymol. 392:278-296, each of which is incorporated herein by reference in its entirety).

Therapeutic silencing of endogenous genes by systemic administration of siRNAs has been described in the literature (Kim, B. et al. (2004) American Journal of Pathology 65:2177-2185; Soutschek, J. et al. (2004) Nature 432:173-178; Pardridge, W. M. (2004) Expert Opin. Biol. Ther. 4(7):1103-1113, each of which is incorporated herein by reference in its entirety).

siRNAs induce a sequence-specific reduction in expression of a gene by the process of RNAi. Thus, siRNA is the intermediate effector molecule of the RNAi process. Some nucleic acid molecules or constructs provided herein include dsRNA molecules comprising 16-30, e.g., 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the mRNA of c-Myb and the other strand is identical or substantially identical to the first strand. However, it will be appreciated that the dsRNA molecules may have any number of nucleotides in each strand which allows them to reduce the level of c-Myb protein or the level of a nucleic acid encoding c-Myb. The dsRNA molecules provided herein can be chemically synthesized, or can be transcribed in vitro from a DNA template, or in vivo from, e.g., shRNA. The dsRNA molecules can be designed using any method known in the art.

An example method for designing dsRNA molecules is provided in the pSUPER RNAi SYSTEM™ (OligoEngine, Seattle, Wash.). The system provides inducible expression of a siRNA in a transfected cell. To effect silencing of a specific gene, a pSUPERIOR vector is used in concert with a pair of custom oligonucleotides that include a unique 19-nt sequence derived from the mRNA transcript of the gene targeted for suppression (the "N-19 target sequence"). The N-19 target sequence corresponds to the sense strand of the pSUPER-generated siRNA, which in turn corresponds to a 19-nt sequence within the mRNA. In the mechanism of RNAi, the antisense strand of the siRNA duplex hybridizes to this region of the mRNA to mediate cleavage of the molecule. These forward and reverse oligonucleotides are annealed and cloned into the vector so that the desired siRNA duplex can be generated. The sequence of the forward oligonucleotide includes the unique N-19 target in both sense and antisense orientation, separated by a 9-nt spacer sequence. The resulting transcript of the recombinant vector is predicted to fold back on itself to form a 19-base pair stem-loop structure. The stem-loop precursor transcript is quickly cleaved in the cell to produce a functional siRNA (T. R. Brummelkamp, et al, Science 296, 550 (2002)). More example methods are provided in Taxman D. J. et al. (2006) BMC Biotechnol. 6:7; and McIntyre G. J. et al. (2006) BMC Biotechnol. 6:1, each of which is incorporated by reference in its entirety.

Nucleic acids provided herein can include both unmodified siRNAs and modified siRNAs as known in the art. For example, in some embodiments, siRNA derivatives can include siRNA having two complementary strands of nucleic acid, such that the two strands are crosslinked. For example, a 3' OH terminus of one of the strands can be modified, or the two strands can be crosslinked and modified at the 3' OH terminus. The siRNA derivative can contain a single crosslink (e.g., a psoralen crosslink). In some embodiments, the siRNA derivative has at its 3' terminus a biotin molecule (e.g., a photocleavable biotin), a peptide (e.g., a Tat peptide), a nanoparticle, a peptidomimetic, organic compounds (e.g., a dye such as a fluorescent dye), or dendrimer. Modifying siRNA derivatives in this way can improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

Nucleic acids provided herein can include nucleic acids that can be unconjugated or can be conjugated to another moiety, such as a nanoparticle, to enhance a property of the compositions, e.g., a pharmacokinetic parameter such as absorption, efficacy, bioavailability, and/or half-life. The conjugation can be accomplished by methods known in the art, e.g., using the methods of Lambert, G. et al. (2001) Drug Deliv. Rev. 47(1): 99-112 (describes nucleic acids loaded to polyalkylcyanoacrylate (PACA) nanoparticles); Fattal et al. (1998) J. Control Release 53 (1-3): 137-43 (describes nucleic acids bound to nanoparticles); Schwab et al. (1994) Ann. Oncol. 5 Suppl. 4:55-58 (describes nucleic acids linked to intercalating agents, hydrophobic groups, polycations or PACA nanoparticles); and Godard, G. et al. (1995) Eur. J. Biochem. 232(2):404-10 (describes nucleic acids linked to nanoparticles). Because RNAi is believed to progress via at least one single stranded RNA intermediate, the skilled artisan will appreciate that ss-siRNAs (e.g., the antisense strand of a ds-siRNA) can also be designed as described herein and utilized according to the claimed methodologies.

Synthetic siRNAs can be delivered to cells by methods known in the art, including cationic liposome transfection and electroporation. However, these exogenous siRNA generally show short term persistence of the silencing effect (4 to 5 days in cultured cells), which may be beneficial in certain embodiments. To obtain longer term suppression of expression for targeted genes, such as MYB, and to facilitate delivery under certain circumstances, one or more siRNA duplexes, e.g., ds siRNA, can be expressed within cells from recombinant DNA constructs. Such methods for expressing siRNA duplexes within cells from recombinant DNA constructs to allow longer-term target gene suppression in cells are known in the art, including mammalian Pol III promoter systems (e.g., H1 or U6/snRNA promoter systems (Tuschl, T. (2002) Nature Biotechnol. 20:446-448) capable of expressing functional double-stranded siRNAs; (Lee, N. S. et al. (2002) Nature Biotechnol. 20:500-505; Miyagishi, M. and Taira, K. (2002) Nature Biotechnol. 20:497-500; Paul, C. P. et al. (2002) Nature Biotechnol. 20:505-508; Yu, J.-Y. et al. (2002) Proc. Natl. Acad. Sci. USA 99(9):6047-6052; Sui, G. et al. (2002) Proc. Natl. Acad. Sci. USA 99(6):5515-5520). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by an H1 or U6 snRNA promoter can be expressed in cells, and can inhibit target gene expression. Constructs containing siRNA sequence(s) under the control of a T7 promoter also make functional siRNAs when co-transfected into the cells with a vector expressing T7 RNA polymerase (Jacque J.-M. et al. (2002) Nature 418:435-438). A single construct may contain multiple sequences coding for siRNAs, such as multiple regions of the MYB gene, such as a nucleic acid encoding the MYB mRNA, and can be driven, for example, by separate Pol III promoter sites.

Nucleic acids provided herein can include micro RNA (miRNAs) which can regulate gene expression at the post transcriptional or translational level. One common feature of miRNAs is that they are all excised from an approximately 70 nucleotide precursor RNA stem-loop, probably by Dicer, an RNase III-type enzyme, or a homolog thereof. By substituting the stem sequences of the miRNA precursor with miRNA sequence complementary to the target mRNA, a vector construct that expresses the novel miRNA can be used to produce siRNAs to initiate RNAi against specific mRNA targets in mammalian cells (Zheng, B. J. (2004) Antivir. Ther. 9:365-374). When expressed by DNA vectors containing polymerase III promoters, micro-RNA designed hairpins can silence gene expression, such as c-Myb expression.

Viral-mediated delivery mechanisms can also be used to induce specific silencing of targeted genes through expression of siRNA, for example, by generating recombinant adenoviruses harboring siRNA under RNA Pol II promoter transcription control (Xia et al. (2002) Nature Biotechnol. 20(10):1006-10). In vitro infection of cells by such recombinant adenoviruses allows for diminished endogenous target gene expression. Injection of recombinant adenovirus vectors into transgenic mice expressing the target genes of the siRNA results in in vivo reduction of target gene expression. In an animal model, whole-embryo electroporation can efficiently deliver synthetic siRNA into post-implantation mouse embryos (Calegari, F. et al. (2002) Proc. Natl. Acad. Sci. USA 99(22):14236-40). In adult mice, efficient delivery of siRNA can be accomplished by the "high-pressure" delivery technique, a rapid injection (within 5 seconds) of a large volume of siRNA containing solution into animal via the tail vein (Lewis, D. L. (2002) Nature Genetics 32:107-108). Nanoparticles, liposomes and other cationic lipid molecules can also be used to deliver siRNA into animals. A gel-based agarose/liposome/siRNA formulation is also available (Jiamg, M. et al. (2004) Oligonucleotides 14(4):239-48).

Nucleic acids provided herein can include an antisense nucleic acid sequence selected such that it is complementary to the entirety of MYB or to a portion of MYB. In some embodiments, a portion can refer to at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, and at least about 80%, at least about 85%, at least about 90%, at least about 95%. In some embodiments, a portion can refer up to 100%. An example mRNA sequence (SEQ ID NO:05) of human MYB is shown in Table.

TABLE 1

```
   1    aatatcaacc tgtttcctcc tcctccttct cctcctcctc cgtgacctcc tcctcctctt
  61    tctcctgaga aacttcgccc cagcggtgcg gagcgccgct gcgcagccgg ggagggacgc
 121    aggcaggcgg cgggcagcgg gaggcggcag cccggtgcgg tccccgcggc tctcggcgga
 181    gccccgcgcc cgccgcgcca tggcccgaag accccggcac agcatatata gcagtgacga
 241    ggatgatgag gactttgaga tgtgtgacca tgactatgat gggctgcttc ccaagtctgg
 301    aaagcgtcac ttggggaaaa caaggtggac ccgggaagag gatgaaaaac tgaagaagct
 361    ggtggaacag aatggaacag atgactggaa agttattgcc aattatctcc cgaatcgaac
 421    agatgtgcag tgccagcacc gatggcagaa agtactaaac cctgagctca tcaagggtcc
 481    ttggaccaaa gaagaagatc agagagtgat agagcttgta cagaaatacg gtccgaaacg
 541    ttggtctgtt attgccaagc acttaaaggg gagaattgga aaacaatgta gggagaggtg
 601    gcataaccac ttgaatccag aagttaagaa aacctcctgg acagaagagg aagacagaat
 661    tatttaccag gcacacaaga gactggggaa cagatgggca gaaatcgcaa agctactgcc
 721    tggacgaact gataatgcta tcaagaacca ctggaattct acaatgcgtc ggaaggtcga
 781    acaggaaggt tatctgcagg agtcttcaaa agccagccag ccagcagtgg ccacaagctt
 841    ccagaagaac agtcatttga tgggttttgc tcaggctccg cctacagctc aactccctgc
 901    cactggccag cccactgtta acaacgacta ttcctattac cacatttctg aagcacaaaa
 961    tgtctccagt catgttccat accctgtagc gttacatgta aatatagtca atgtccctca
1021    gccagctgcc gcagccattc agagacacta taatgatgaa gaccctgaga aggaaaagcg
1081    aataaaggaa ttagaattgc tcctaatgtc aaccgagaat gagctaaaag gacagcagac
1141    acagaaccac acatgcagct accccgggtg gcacagcacc accattgccg accacaccag
1201    acctcatgga gacagtgcac ctgtttcctg tttgggagaa caccactcca ctccatctct
1261    gccagcggat cctggctccc tacctgaaga aagcgcctcc ccagcaaggt gcatgatcgt
1321    ccaccagggc accattctgg ataatgttaa gaacctctta gaatttgcag aaacactcca
1381    atttatagat tctttcttaa acacttccag taaccatgaa aactcagact tggaaatgcc
1441    ttctttaact tccacccccc tcattggtca caaattgact gttacaacac catttcatag
1501    agaccagact gtgaaaactc aaaaggaaaa tactgttttt agaaccccag ctatcaaaag
1561    gtcaatctta gaaagctctc caagaactcc tacaccattc aaacatgcac ttgcagctca
1621    agaaattaaa tacggtcccc tgaagatgct acctcagaca ccctctcatc tagtagaaga
1681    tctgcaggat gtgatcaaac aggaatctga tgaatctgga attgttgctg agtttcaaga
1741    aaatggacca cccttactga agaaaatcaa acaagaggtg gaatctccaa ctgataaatc
1801    aggaaacttc ttctgctcac accactggga aggggacagt ctgaatacccc aactgttcac
1861    gcagacctcg cctgtggcag atgcaccgaa tattcttaca agctccgttt taatggcacc
1921    agcatcagaa gatgaagaca atgttctcaa agcatttaca gtacctaaaa acaggtccct
1981    ggcgagcccc ttgcagcctt gtagcagtac ctgggaacct gcatcctgtg gaaagatgga
2041    ggagcagatg acatcttcca gtcaagctcg taaatacgtg aatgcattct cagcccggac
2101    gctggtcatg tgagacattt ccagaaaagc attatggttt tcagaacact tcaagttgac
2161    ttgggatata tcattcctca acatgaaact tttcatgaat gggagaagaa cctattttg
2221    ttgtggtaca acagttgaga gcagcaccaa gtgcatttag ttgaatgaag tcttcttgga
2281    tttcacccaa ctaaaaggat ttttaaaaat aaataacagt cttacctaaa ttattaggta
2341    atgaattgta gccagttgtt aatatcttaa tgcagatttt tttaaaaaaa acataaaatg
2401    atttatctgt attttaaagg atccaacaga tcagtatttt ttcctgtgat gggttttttg
2461    aaatttgaca cattaaaagg tactccagta tttcactttt ctcgatcact aaacatatgc
2521    atatattttt aaaaatcagt aaaagcatta ctctaagtgt agacttaata ccatgtgaca
2581    tttaatccag attgtaaatg ctcatttatg gttaatgaca ttgaaggtac atttattgta
2641    ccaaccatt ttatgagttt tctgttagct tgctttaaaa attattactg taagaaatag
2701    ttttataaaa aattatatatt ttattcagta atttaattt gtaaatgcca aatgaaaaac
2761    gttttttgct gctatggtct tagcctgtag acatgctgct agtatcagag gggcagtaga
2821    gcttggacag aaagaaaaga aacttggtgt taggtaattg actatgcact agtatttcag
2881    acttttttaat tttatatata tatacatttt ttttccttct gcaatacatt tgaaaacttg
2941    tttgggagac tctgcatttt ttattgtgt tttttgtta ttgttggttt atacaagcat
3001    gcgttgcact tcttttttgg gagatgtgtg ttgttgatgt tctatgtttt gttttgagtg
3061    tagcctgact gttttataat ttgggagttc tgcatttgat ccgcatcccc tgtggttct
3121    aagtgtatgg tctcagaact gttgcatgga tcctgtgttt gcaactgggg agacagaaac
3181    tgtggttgat agccagtcac tgccttaaga acatttgatg caagatggcc agcactgaac
3241    ttttgagata tgacggtgta cttactgcct tgtagcaaaa taaagatgtg cccttatttt
3301    acctacaaa
```

ACCESSION NM_001130172
VERSION     NM_001130172.1  GI: 194328726

An antisense oligonucleotide can have a length of at least about 5 nucleotides, at least about 7 nucleotides, at least about 10 nucleotides, at least about 15 nucleotides, at least about 20 nucleotides, at least about 25 nucleotides, at least about 30 nucleotides, at least about 35 nucleotides, at least about 40 nucleotides, at least about 45 nucleotides, at least about 50 nucleotides, at least about 55 nucleotides, at least about 60 nucleotides, at least about 65 nucleotides, at least about 70 nucleotides, at least about 75 nucleotides, at least about 80 nucleotides, at least about 85 nucleotides, at least about 90 nucleotides, at least about 95 nucleotides, and at least about 100 nucleotides. An antisense nucleic acid of the invention can be constructed using chemical synthesis and enzymatic ligation reactions using procedures known in the art. For example, an antisense nucleic acid can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation, namely, RNA transcribed from the inserted nucleic acid will be of an antisense orientation to a target nucleic acid of interest. The antisense nucleic acid molecules can be administered to a subject (e.g., systemically or locally by direct injection at a tissue site, or generated in situ such that they hybridize with or bind to cellular mRNA and/or genomic DNA encoding MYB to thereby inhibit its expression. Alternatively, antisense nucleic acid molecules can be modified to target particular cells and then administered systemically. For systemic administration, antisense molecules can be modified such that they specifically bind to receptors or antigens expressed on a selected cell surface, e.g., by linking the antisense nucleic acid molecules to peptides or antibodies that bind to particular cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter can be used.

In some embodiments, antisense oligonucleotide include α-anomeric nucleic acid molecules. An α-anomeric nucleic acid molecule forms specific double-stranded hybrids with complementary RNA in which, contrary to the usual beta-units, the strands run parallel to each other (Gaultier, C. et al. (1987) Nucleic Acids. Res. 15:6625-6641). The antisense nucleic acid molecule can also comprise a 2'-o-methylribonucleotide, or a chimeric RNA-DNA analogue (Inoue, H. et al. (1987) Nucleic Acids Res. 15:6131-6148; Inoue, H. et al. (1987a) FEBS Lett. 215:327-330).

Additional methods or compositions described herein to reduce the level of c-Myb protein or a nucleic acid encoding c-Myb within a cell, such as endogenous c-Myb, or an mRNA encoding c-Myb, can utilize ribozymes. In general, a ribozyme is a catalytic RNA molecule that cleaves RNA in a sequence specific manner. Ribozymes that cleave themselves are known as cis-acting ribozymes, while ribozymes that cleave other RNA molecules are known as trans-acting ribozymes. The term "cis-acting ribozyme sequence" as used herein refers to the sequence of an RNA molecule that has the ability to cleave the RNA molecule containing the cis-acting ribozyme sequence. A cis-acting ribozyme sequence can contain any sequence provided it has the ability to cleave the RNA molecule containing the cis-acting ribozyme sequence. For example, a cis-acting ribozyme sequence can have a sequence from a hammerhead, axhead, or hairpin ribozyme. In addition, a cis-acting ribozyme sequence can have a sequence from a hammerhead, axhead, or hairpin ribozyme that is modified to have either slow cleavage activity or enhanced cleavage activity. For example, nucleotide substitutions can be made to modify cleavage activity (Doudna and Cech, Nature, 418:222-228 (2002)). Examples of ribozyme sequences that can be used with the methods and compositions described herein include those described in U.S. Pat. No. 6,271,359, and U.S. Pat. No. 5,824,519, incorporated by reference in their entireties. One example method for preparing a ribozyme is to synthesize chemically an oligodeoxyribonucleotide with a ribozyme catalytic domain (approximately 20 nucleotides) flanked by sequences that hybridize to the target mRNA. The oligodeoxyribonucleotide is amplified by using the substrate binding sequences as primers. The amplified product is cloned into a eukaryotic expression vector. A ribozyme can be expressed in eukaryotic cells from the appropriate DNA vector. If desired, the activity of the ribozyme may be augmented by its release from the primary transcript by a second ribozyme (Ohkawa et al., Nucleic Acids Symp. Ser., 27: 15-6 (1992); Taira et al., Nucleic Acids Res., 19: 5125-30 (1991); Ventura et al., Nucleic Acids Res., 21, 3249-55 (1993).

Methods of Treatment

Some embodiments relate to compositions and/or methods for treating or ameliorating disorders related to increased levels of expression of c-Myb protein or a nucleic acid encoding c-Myb, such as an mRNA encoding c-Myb or increased activity of c-Myb protein. In some embodiments, treating such disorders can include decreasing the level of a nucleic acid encoding c-Myb in the cell of a subject. In some embodiments, a composition can include an isolated nucleic acid having activity to reduce the levels of c-Myb in a cell of a subject. Examples of such nucleic acids are described herein and include a sequence encoding c-Myb or a fragment thereof, or a sequence encoding antisense c-Myb or a fragment thereof. Such nucleic acids can be useful for RNA interference or antisense technologies. A fragment of a polynucleotide sequence will be understood to include any nucleotide fragment having, for example, at least about 5 successive nucleotides, at least about 12 successive nucleotides, at least about 15 successive nucleotides, at least about 18 successive nucleotides, or at least about 20 successive nucleotides of the sequence from which it is derived. An upper limit for a fragment can include, for example, the total number of nucleotides in a full-length sequence encoding a particular polypeptide. Methods to select for nucleic sequences that have activity to reduce the level of a protein, such as c-Myb protein or the level of a nucleic acid encoding a polypeptide, such as an mRNA encoding c-Myb or the activity of c-Myb protein in a cell or a subject, are also provided herein.

In some embodiments, a nucleic acid having activity to reduce c-Myb protein expression or the level of a nucleic acid encoding c-Myb or the activity of c-Myb protein in a cell of a subject is further operably linked to a regulatory sequence. Regulatory sequences include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990), the disclosure of which is incorporated herein by reference in its entirety. Regulatory sequences include those which direct constitutive expression of a nucleotide sequence in many types of host cell and those which direct expression of the nucleotide sequence only in certain host cells (e.g., tissue-specific regulatory sequences). Tissue specific promoters may be used to effect transcription in specific tissues or cells so as to reduce potential toxicity or undesirable effects to non-targeted tissues. For example, promoters such as the PSA, probasin, prostatic acid phosphatase or prostate-specific glandular kallikrein (hK2) may be used to target gene expression in the prostate. Similarly, promoters as follows may be used to target gene expression in other tissues. Examples of more tissue specific promoters include in (a) pancreas: insulin, elastin, amylase, pdr-I, pdx-I, glucokinase; (b) liver: albumin PEPCK, HBV enhancer, a fetoprotein, apolipoprotein C, α-I antitrypsin, vitellogenin, NF-AB, Transthyretin; (c) skeletal muscle: myosin H chain, muscle creatine kinase, dystrophin, calpain p94, skeletal α-actin, fast troponin 1; (d) skin: keratin K6, keratin KI; (e) lung: CFTR, human cytokeratin IS (K 18), pulmonary surfactant proteins A, B and C, CC-10, Pi; (f) smooth muscle: sm22 α, SM-α-actin; (g) endothelium: endothelin-I, E-selectin, von Willebrand factor, TIE, KDR/flk-I; (h) melanocytes: tyrosinase; (i) adipose tissue: lipoprotein lipase, adipsin, acetyl-CoA carboxylase, glycerophosphate dehydrogenase, adipocyte P2; (j) blood: P-globin; and (k) mammary: MMTV, and whey acidic protein (WAP).

In certain embodiments, it may be desirable to activate transcription at specific times after administration of a vector comprising a nucleic acid having activity to reduce c-Myb protein level or the level of a nucleic acid encoding c-Myb or the activity of c-Myb protein in a cell. This may be done with such promoters as those that may be regulated by hormone or cytokine. For example, in a gonadal tissue where specific steroids are produced or routed to, use of androgen or estrogen regulated promoters may be advantageous. Such promoters that are hormone regulatable include MMTV, MT-1, ecdysone and RuBisco. Other hormone regulated promoters such as those responsive to thyroid, pituitary and adrenal hormones are expected to be useful with the nucleic acids described herein. Cytokine and inflammatory protein responsive promoters that could be used include K and T Kininogen, c-fos, TNF-α, C-reactive protein, haptoglobin, serum amyloid A2, C/EBP α, IL-1, IL-6, Complement C3, IL-8, α-1 acid glycoprotein, α-1 antitrypsin, lipoprotein lipase, angiotensinogen, fibrinogen, c-jun (inducible by phorbol esters, TNF α, UV radiation, retinoic acid, and hydrogen peroxide), collagenase (induced by phorbol esters and retinoic acid), metallothionein (heavy metal and glucocorticoid inducible), Stromelysin (inducible by phorbol ester, interleukin-1 and EGF), α-2 macroglobulin and α-I antichymotrypsin. It is envisioned that any of the promoters described herein, alone or in combination with another, may be useful depending on the action desired.

Nucleic acid constructs having activity to reduce c-Myb protein levels or the level of a nucleic acid encoding c-Myb or the activity of c-Myb protein in a cell and described herein can be introduced in vivo as naked DNA plasmids, for example, using transfection, electroporation (e.g., transcutaneous electroporation), microinjection, transduction, cell fusion, DEAE dextran, calcium phosphate precipitation, use of a gene gun, or use of a DNA vector transporter (Wu et al. J. Biol. Chem., 267:963-967, 1992; Wu and Wu J. Biol. Chem., 263:14621-14624, 1988; and Williams et al. Proc. Natl. Acad. Sci. USA 88:2726-2730, 1991). A needleless delivery device, such as a BIOJECTOR® needleless injection device can be utilized to introduce nucleic acid constructs in vivo. Receptor-mediated DNA delivery approaches can also be used (Curiel et al. Hum. Gene Ther., 3:147-154, 1992; and Wu and Wu, J. Biol. Chem., 262:4429-4432, 1987). Methods for formulating and administering naked DNA to mammalian muscle tissue are disclosed in U.S. Pat. Nos. 5,580,859 and 5,589,466, both of which are herein incorporated by reference in their entireties. Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931), the disclosures of which are incorporated herein by reference in their entireties.

Alternatively, electroporation can be utilized conveniently to introduce nucleic acid constructs, having activity to reduce c-Myb protein levels or the level of a nucleic acid encoding c-Myb or the activity of c-Myb protein in a cell and described herein, into cells. Electroporation is well known by those of ordinary skill in the art (see, for example: Lohr et al. Cancer Res. 61:3281-3284, 2001; Nakano et al. Hum Gene Ther. 12:1289-1297, 2001; Kim et al. Gene Ther. 10:1216-1224, 2003; Dean et al. Gene Ther. 10:1608-1615, 2003; and Young et al. Gene Ther 10:1465-1470, 2003). For example, in electroporation, a high concentration of vector DNA is added to a suspension of host cell (such as isolated autologous peripheral blood or bone marrow cells) and the mixture shocked with an electrical field. Transcutaneous electroporation can be utilized in animals and humans to introduce heterologous nucleic acids into cells of solid tissues (such as muscle) in vivo. Typically, the nucleic acid constructs are introduced into tissues in vivo by introducing a solution containing the DNA into a target tissue, for example, using a needle or trochar in conjunction with electrodes for delivering one or more electrical pulses. For example, a series of electrical pulses can be utilized to optimize transfection, for example, between 3 and ten pulses of 100 V and 50 msec. In some cases, multiple sessions or administrations are performed.

Another well known method that can be used to introduce nucleic acid constructs, having activity to reduce c-Myb protein levels or the level of a nucleic acid encoding c-Myb or the activity of c-Myb protein in a cell and described herein, into host cells is biolistic transformation. One method of biolistic transformation involves propelling inert or biologically active particles at cells, e.g., U.S. Pat. Nos. 4,945,050, 5,036,006; and 5,100,792, the disclosures of which are hereby incorporated by reference in their entireties. Generally, this procedure involves propelling inert or biologically active particles at the cells under conditions effective to penetrate the outer surface of the cell and to be incorporated within the interior thereof. When inert particles are utilized, the plasmid can be introduced into the cell by coating the particles with the plasmid containing the exogenous DNA. Alternatively, the target cell can be surrounded by the plasmid so that the plasmid is carried into the cell by the wake of the particle.

Alternatively, nucleic acid constructs, having activity to reduce c-Myb protein levels or the level of a nucleic acid encoding c-Myb or the activity of c-Myb protein in a cell and described herein, can be introduced in vivo by lipofection. Synthetic cationic lipids designed to limit the difficulties and dangers encountered with liposome mediated transfection can be used to prepare liposomes for in vivo transfection of a gene encoding a marker (Felgner et al. Proc. Natl. Acad. Sci. USA 84:7413-7417, 1987; Mackey, et al. Proc. Natl. Acad. Sci. USA 85:8027-8031, 1988; Ulmer et al. Science 259:1745-1748, 1993, the disclosures of which are incorporated herein by reference in their entireties). The use of cationic lipids can promote encapsulation of negatively charged nucleic acids, and also promote fusion with negatively charged cell membranes (Felgner and Ringold Science 337:387-388, 1989, the disclosure of which is incorporated by reference herein in its entirety). Particularly useful lipid compounds and compositions for transfer of nucleic acids are described in WO95/18863 and WO96/17823, and in U.S. Pat. No. 5,459,127, incorporated herein by reference in their entireties.

In some embodiments, the nucleic acid constructs, having activity to reduce c-Myb protein levels or the level of a nucleic acid encoding c-Myb or the activity of c-Myb protein in a cell and described herein, are viral vectors. Methods for constructing and using viral vectors are known in the art (See e.g., Miller and Rosman, BioTech., 7:980-990, 1992). Preferably, the viral vectors are replication defective, that is, they are unable to replicate autonomously in the target cell. In some cases, the replication defective virus retains the sequences of its genome that are necessary for encapsulating the viral particles. DNA viral vectors commonly include attenuated or defective DNA viruses, including, but not limited to, herpes simplex virus (HSV), papillomavirus, Epstein Barr virus (EBV), adenovirus, adeno-associated virus (AAV), Moloney leukemia virus (MLV) and human immunodeficiency virus (HIV) and the like. Defective viruses, that entirely or almost entirely lack viral genes, are preferred, as defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al. Mol. Cell. Neurosci., 2:320-330, 1991, the disclosure of which is incorporated herein by reference in its entirety), defective herpes virus vector lacking a glycoprotein L gene (See for example, Patent Publication RD 371005 A, incorporated herein by reference in its entirety), or other defective herpes virus vectors (See e.g., WO 94/21807; and WO 92/05263, incorporated herein by reference in their entireties); an attenuated adenovirus vector, such as the vector described by Stratford-Perricaudet et al. (J. Clin. Invest., 90:626-630 1992; La Salle et al., Science 259:988-990, 1993, the disclosure of which is incorporated herein by reference in its entirety); and a defective adeno-associated virus vector (Samulski et al., J. Virol., 61:3096-3101, 1987; Samulski et al., J. Virol., 63:3822-3828, 1989; and Lebkowski et al., Mol. Cell. Biol., 8:3988-3996, 1988, the disclosures of which are incorporated herein by reference in their entireties).

In some embodiments, the viral vectors, having activity to reduce c-Myb protein levels or the level of a nucleic acid encoding c-Myb or the activity of c-Myb protein in a cell and described herein, may be adenovirus vectors. Adenoviruses are eukaryotic DNA viruses that can be modified to efficiently deliver a nucleic acid of the disclosure to a variety of cell types. Various serotypes of adenovirus exist. Of these serotypes, preference is given, within the scope of the present disclosure, to type 2, type 5 or type 26 human adenoviruses (Ad 2 or Ad 5), or adenoviruses of animal origin (See e.g., WO94/26914 and WO2006/020071, the disclosures of which are incorporated herein by reference in their entireties). Those adenoviruses of animal origin that can be used within the scope of the present disclosure include adenoviruses of canine, bovine, murine (e.g., Mav1, Beard et al. Virol., 75-81, 1990, the disclosure of which is incorporated herein by reference in its entirety), ovine, porcine, avian, and simian (e.g., SAV) origin. In some embodiments, the adenovirus of animal origin is a canine adenovirus, such as a CAV2 adenovirus (e.g. Manhattan or A26/61 strain (ATCC VR-800)).

Some embodiments include pharmaceutical compositions comprising a nucleic acid which reduces c-Myb protein levels or the level of a nucleic acid encoding c-Myb or the activity of c-Myb protein and a suitable carrier. While any suitable carrier known to those of ordinary skill in the art may be employed in the pharmaceutical compositions described herein, the type of carrier will typically vary depending on the mode of administration. Compositions described herein may be formulated for any appropriate manner of administration, including for example, topical, oral, nasal, mucosal, intravenous, intracranial, intraperitoneal, subcutaneous and intramuscular administration. Carriers for use within such pharmaceutical compositions are biocompatible, and may also be biodegradable. In certain embodiments, the formulation preferably provides a relatively constant level of active component release.

The pharmaceutical compositions described herein can further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions described herein may be formulated as a lyophilizate.

Pharmaceutical compositions described herein can be administered to a subject, such as a mammal, such as a human. Pharmaceutical compositions can be administered at a therapeutically effective amount. A "therapeutically effective amount" is a quantity of a chemical composition (such as a nucleic acid construct, vector, or polypeptide) used to achieve a desired effect in a subject being treated. Pharmaceutical compositions may be administered either prior to or following surgical removal of primary tumors and/or treatment such as administration of radiotherapy or conventional chemotherapeutic drugs. Pharmaceutical compositions may be administered in combination with at least one additional therapeutic compound, such as a chemotherapeutic compound.

Indications

Methods and compositions described herein can be used to treat disorders that relate to increased activity of c-Myb. Examples of such disorders include cancers, for example, pancreatic cancer and prostate cancer, including castration-resistant prostate cancer. More examples include any cancer that may be treated with the therapeutic compounds described herein. In addition, the role of c-Myb has been investigated in a variety of other cancers such as, leukemia, colorectal, breast and Glioma (See e.g., Biroccio A, et al., Am J. Pathol. 2001 April; 158(4):1289-99; Cesi V, et al., Cell Cycle. 2011 Dec. 1; 10(23):4149-61; Miyazaki T, et al., Clin Cancer Res. 2012 Mar. 1; 18(5):1268-80; Tanno B, et al J Biol. Chem. 2010 Sep. 17; 285(38):29434-45; Wallrapp C, et al. Cancer Res 1997; 57:3135-9).

Methods to Increase Sensitivity of Cells to Therapeutic Compounds

It has been discovered that reducing c-Myb protein levels or the level of a nucleic acid encoding c-Myb or the activity of c-Myb protein in a cell increases the sensitivity of the cell to particular therapeutic compounds. Accordingly, some embodiments relate to methods for increasing the sensitivity of a cell or a subject to a therapeutic compound. As will be understood, increasing the sensitivity of a cell or a subject to a therapeutic compound can decrease the therapeutically effective amount of a therapeutic compound needed to treat the cell or subject.

In some embodiments, a cell or a subject may be treated with an agent that reduces c-Myb protein levels or the level of a nucleic acid encoding c-Myb or the activity of c-Myb protein. Reducing c-Myb protein levels or the level of a nucleic acid encoding c-Myb or the activity of c-Myb protein in certain cells can increase the sensitivity of those cells to particular therapeutic compounds. Such cells can include cells in which c-Myb expression is increased compared to normal cells, for example, in certain neoplastic cells.

Therapeutic compounds for which the therapeutic dosage may be reduced can include chemotherapeutic agents. Examples of chemotherapeutic agents include taxanes, such as, docetaxel and paclitaxel.

Methods for Identifying Agents

More embodiments include methods of identifying compounds and agents useful for the methods and compositions described herein. Some such methods can be useful to evaluate test compounds useful to treat disorders related to increased expression of c-Myb or activity of c-Myb protein. More methods can be useful to evaluate test compounds useful to increase the sensitivity of certain cells to particular therapeutic compounds.

In some embodiments, a test compound is evaluated by contacting the cell with the test compound. A test compound that reduces the level of c-Myb protein or the level of a nucleic acid encoding c-Myb or the activity of c-Myb protein may be useful to decrease the activity of pathways that include c-Myb. Such a test compound can be useful to treat or ameliorate disorders related to increased activity of c-Myb. More methods include comparing the level of a nucleic acid encoding c-Myb or the level of c-Myb protein or the activity of c-Myb protein in a target cell to the level of a nucleic acid encoding c-Myb or the level of c-Myb protein or the activity of c-Myb protein in a target cell contacted with the test compound.

More methods can also include selecting a test compound that, in addition to reducing the level of the c-Myb protein or the level of a nucleic acid encoding c-Myb or the activity of c-Myb protein also reduces the expression level of prostate-specific antigen (PSA) protein or level of a nucleic acid encoding PSA. More methods include determining whether the test compound reduces the level of a nucleic acid encoding CXCR4 or the level of CXCR4 protein in the target cell. Some such methods include comparing the level of a nucleic acid encoding CXCR4 or the level of CXCR4 protein in a target cell which has not been contacted with the test compound to the level of a nucleic acid encoding CXCR4 or the level of CXCR4 protein in a target cell contacted with the test compound.

More embodiments include methods and compositions for assessing the effectiveness of a compound or agent. In some such embodiments, the compound or agent comprises a nucleic acid. Some embodiments include determining whether a test nucleic acid reduces the level of a nucleic acid encoding c-Myb or the level of c-Myb protein or the activity of c-Myb protein in a target cell, wherein the test nucleic acid is identified as having potential effectiveness as a therapeutic agent if the test nucleic acid reduces the level of the nucleic acid encoding c-Myb or the level of the c-Myb protein or the activity of c-Myb protein in a target cell. A compound or agent, such as a nucleic acid, that reduces the level of the nucleic acid encoding c-Myb or the level of the c-Myb protein or the activity of c-Myb protein in a target cell is indicative of an effective compound or agent. Some embodiments also include determining whether the test nucleic acid reduces the level of a nucleic acid encoding PSA in the target cell. Some such embodiments also include comparing the level of a nucleic acid encoding PSA in a target cell which has not been contacted with the test nucleic acid to the level of a nucleic acid encoding PSA in a target cell contacted with the test nucleic acid. A compound or agent, such as a nucleic acid, that reduces the level of the nucleic acid encoding PSA in a target cell is indicative of an effective compound or agent. Some embodiments also include determining whether the test nucleic acid reduces the level of a nucleic acid encoding CXCR4 or the level of CXCR4 protein in the target cell. Some such embodiments also include comparing the level of a nucleic acid encoding CXCR4 or the level of CXCR4 protein in a target cell which has not been contacted with the test nucleic acid to the level of a nucleic acid encoding CXCR4 or the level of CXCR4 protein in a target cell contacted with the test nucleic acid. A compound or agent, such as a nucleic acid, that reduces the level of the nucleic acid encoding c-CXCR4 or the level of the CXCR4 protein in a target cell is indicative of an effective compound or agent.

Kits

Some methods and compositions provided herein include kits for evaluating the presence of a cancer or the stage of a cancer in a sample, such as pancreatic cancer or prostate cancer, such as castration-resistant prostate cancer. In some embodiments a kit can include at least one reagent for determining the level of c-Myb protein or the level of a nucleic acid encoding c-Myb or the activity of c-Myb protein. In some embodiments, kits can include one or more antibodies or fragments thereof that specifically bind to c-Myb. Such antibodies or fragments may be provided attached to a support material, as described herein. Kits can also include additional elements, such as reagents or buffers, to be used in an assay. Such kits may also, or alternatively, contain a detection reagent as described above that contains a reporter group suitable for direct or indirect detection of antibody binding. In some embodiments, kits can include at least one oligonucleotide probe or primer that hybridizes to a polynucleotide encoding c-Myb. Such an oligonucleotide may be used, for example, within a PCR or hybridization assay. Additional components that may be present within such kits include a second oligonucleotide and/or a diagnostic reagent or container to facilitate the detection of a polynucleotide encoding an additional marker.

Some methods and compositions provided herein include kits for ameliorating a cancer in subject, such as pancreatic cancer or prostate cancer, such as castration-resistant prostate cancer. In some embodiments, a kit can include a therapeutic agent that reduces the level of c-Myb protein or level of a nucleic acid encoding c-Myb or the activity of c-Myb protein in a cell. In some embodiments, kits can include instruments for administering a therapeutic agent to a subject.

EXAMPLES

Materials and Methods

Cell culture. LNCaP, DU145, PC3 (ATCC, Rockville, Md.) and C4-2 (UroCor Inc., Oklahoma City, Okla.) cell lines were maintained in RPMI 1640 media (Invitrogen, Carlsbad, Calif.) supplemented with 5.0% fetal bovine serum (FBS), and 100 µM each of penicillin and streptomycin (Invtrogen). RWPE1 and RWPE2 (ATCC) were maintained in keratinocyte serum free medium (Gelantis San Diego, Calif.) containing 50 mg/ml gentamycin, 0.05 mg/ml bovine pituitary extract (BPE), and 5 ng/ml epidermal growth factor. All cell lines were cultured in humidified atmosphere at 37° C. with 5% CO2 and media was replaced every alternate day. Short tandem repeats (STR) genotyping and intermittent testing for androgen-responsiveness (growth and androgen-receptor activity) was used as a way to authenticate the cell lines.

Constructs, transfections, and treatments. Short hairpin RNA (shRNA) expression constructs for Myb (pGFP-V-RS-shMyb) and scrambled control (pGFP-V-RS-Scr) were purchased from Origene (Rockville, Md.), while a Myb overexpression construct was generated through sub-cloning of Myb insert from pCMV6-XL5-Myb plasmid (Origene) into pCMV6-NEO vector (Origene). The shRNA for Myb included the following sequence: CGTTGGTCTGTTATTGCCAAGCACTTAAA (SEQ ID NO:06).

For ectopic Myb overexpression and knockdown, LNCaP and C4-2 cell lines were transfected with pCMV6-Myb and pGFP-V-RS-shMyb, respectively, along with their respective control plasmids, using FuGENE as a transfection reagent as per the manufacturer's instructions. Stable pooled population of transfected cells were selected in RPMI-media containing G148 (200 µg/ml; for overexpression) or Puromycin (2 µg/ml; for shRNA), expanded and examined for stable Myb overexpression or silencing. To assess androgen-independence, cells were grown in culture media supplemented with 5% charcoal-stripped serum (CSS, steroid-reduced) (Gemini Bio-Products, West Sacramento, Calif.).

RNA Isolation and reverse transcription polymerase chain reaction (RT-PCR). Total RNA was isolated using RNeasy Purification Kit (Qiagen, Maryland, USA) and reverse transcribed using the High Capacity cDNA Reverse Transcription Kit (Applied Biosystems, Carlsbad, Calif.) following manufacturer's instructions. Quantitative real-time PCR was performed in 96-well plates using SYBRGreen Master Mix (Applied Biosystems, Warrington, UK) on an iCycler system (Bio-Rad, Hercules, Calif.). The following PCR primer pairs were used: Myb forward (SEQ ID NO:01) [5'-TCAGGAAACTTCTTCTGCTCACA-3']; Myb reverse (SEQ ID NO:02) [5'-AGGTTCCCAGGTACTGCT-3'] and GAPDH forward (SEQ ID NO:03) [5'-GCTGTGTGGCAAAGTC-CAAG-3'] and GAPDH reverse (SEQ ID NO:04) [5'-GGTCAGGCTCCTGGAAGATA-3']. The thermal conditions for real-time PCR assays were as follows: cycle 1: 95° C. for 10 min, cycle 2 (×40): 95° C. for 10 sec and 58° C. for 45 sec.

Western blot analysis. Cells were processed for protein extraction and western blotting as described (24). Immunodetection was carried out using specific antibodies against: Myb, PSA, AR and Vimentin (all rabbit monoclonal) (Epitomics, Burlingame, Calif.), SLUG, SNAIL, BAD, Bcl-xL (all rabbit monoclonal), Bax (rabbit polyclonal) (Cell Signaling Technology, Beverly, Mass.), E-cadherin and N-cadherin (mouse monoclonal) (BD transduction laboratories, Bedford, Mass.), p21 (mouse monoclonal), p27, Cyclin A1, Cyclin D1, Cyclin E1, Twist (all rabbit polyclonal) (Santa Cruz Biotechnology, Santa Cruz, Calif.) and β-actin (mouse monoclonal) (Sigma-Aldrich, St. Louis Mo.). All secondary antibodies (Santa Cruz) were used at 1:2500 dilutions. Blots were processed with ECL plus Western Blotting detection kit (Thermo Scientific, Logan, Utah) and the signal detected using an LAS-3000 image analyzer (Fuji Photo Film Co., Tokyo, Japan).

Immunofluorescence assay. Cells were grown at low density on sterilized coverslips, washed with 0.1 mol/L HEPES containing Hanks' buffer, and fixed in ice-cold methanol at −20° C. for 2 min. After nonspecific blocking with 10% goat serum containing 0.05% Tween 20 for at least 30 min, cells were incubated with anti-Myb rabbit monoclonal antibody in PBS (1:100) for 90 min at room temperature followed by washing. Cells were then incubated with TRITC-conjugated goat anti-rabbit secondary antibodies (Santa Cruz) for 60 min and after washing, the coverslips were mounted on glass slides in antifade Vectashield mounting medium (Vector Laboratories, Burlingame, Calif.). For actin filament staining, cells grown on glass coverslips were fixed with 4% formaldehyde in PBS for 10 min at room temperature. The fixed cells were washed with PBS and permeabilized with 0.2% Triton X-100 in PBS for 5 min. After washing, the cells were stained with Alexafluor 488 phalloidin (Molecular Probes, Invitrogen, Eugene, Oreg.) for 20 min, washed twice with PBS-Tween 20 and mounted on glass slides in antifade Vectashield mounting medium. Immunostaining was observed under Nikon Eclipse TE2000-U fluorescent microscope (Nikon Instruments Inc, Melville, N.Y.).

Growth kinetics assay. Cells ($1 \times 10^4$/well) were seeded in triplicate in 6-well plates and allowed to grow for different time intervals. The growth rate was determined by counting the number of cells on a hemocytometer, every day for eight days. Cell population doubling time (Td) was calculated during exponential growth phase (96-144 h) using the following formula: Td=0.693 t/ln(Nt/N0), where t is time (in h), Nt is the cell number at time t, and N0 is the cell number at initial time (25).

Soft-agar colony formation and plating efficiency assay. Equal volumes of agarose (1.6%) and growth medium were mixed and plated to form bottom layer (0.8% agar growth medium) in 6-well plates. Cells ($2.5 \times 10^3$ cells/mL) were suspended in regular media, mixed with equal volume of 0.6% agarose and cell suspension-agar mix (2 mL) seeded as top layer in each well. Plates were incubated under normal culture conditions for 3 weeks for colony formation. Colonies were stained with 0.005% crystal violet (Sigma-Aldrich) in PBS, observed using Nikon Eclipse microscope (Nikon Instruments Inc.), and counted in ten randomly selected fields (×100 magnification). For plating efficiency, single cell suspensions were plated in 6-well plates at a density of $2.5 \times 10^3$ cells/well in complete or steroid-reduced media for colony formation. After two weeks, colonies were fixed with methanol, stained with crystal violet, photographed and counted using Image analysis software (Gene Tools, Syngene, Frederick, Md.).

Cell cycle analysis. Cells were synchronized by culturing them in serum-free media for 72 h, and then incubated in either regular or steroid-reduced media for 24 h. After washing and trypsinization, cells were fixed with 70% ethanol overnight at 4° C., washed with cold PBS and stained with propidium iodide using PI/RNase staining buffer for 1 h at 37° C. Stained cells were analyzed by flow-cytometry on a BD-FACS Canto™ II (Becton-Dickinson, San Jose, Calif.). The percentage of cell population in various phases of cell cycle was calculated using Mod Fit LT software (Verity Software House, Topsham, Me.).

Apoptosis assay. Apoptosis was measured by using the PE Annexin V apoptosis detection kit (BD Biosciences, San Diego, Calif.). The cells were grown in steroidsupplemented (FBS) or -reduced (CSS) condition for 96 h. Apoptosis was detected by staining the cells with PE Annexin V and 7AAD solution followed by flow cytometry.

Motility and invasion assays. For motility assay, cells ($2\times10^5$) were plated in the top chamber of non-coated polyethylene teraphthalate membrane (6-well inserts, pore size 8 µM; BD Biosciences). For the invasion assay, $5\times10^4$ cells were plated in the top chamber of the transwell with a Matrigel-coated polycarbonate membrane (24-well inserts 0.8 µM, BD Biosciences). RPMI-1640 medium with 10% FBS was added to the lower chamber as a chemoattractant. After 16 hours of incubation, cells remaining on the upper surface of the insert membrane were removed by cotton swab. Cells that had migrated or invaded through the membrane/Matrigel to the bottom of the insert were fixed and stained with Diff-Quick cell staining kit (Dade Behring, Inc., Newark, Del.), and mounted on slide.

Aggregation assay. Cells were tested for their ability to aggregate in hanging drop suspension cultures as previously demonstrated (25). In brief, drops of cell suspension (20 µl each containing 20,000 cells) were placed onto the inner surface of the lid of a Petri dish. The lid was then placed on the Petri dish so that the drops were hanging from the lid with the cells suspended within them. To eliminate evaporation, 8 ml of serumfree culture medium were placed in the bottom of the Petri dish. After overnight incubation at 37° C., the lid of the Petri dish was inverted and photographed using Nikon Eclipse microscope (Nikon Instruments Inc.).

Results

Myb Expression in Cell-Lines

Figure 1A:
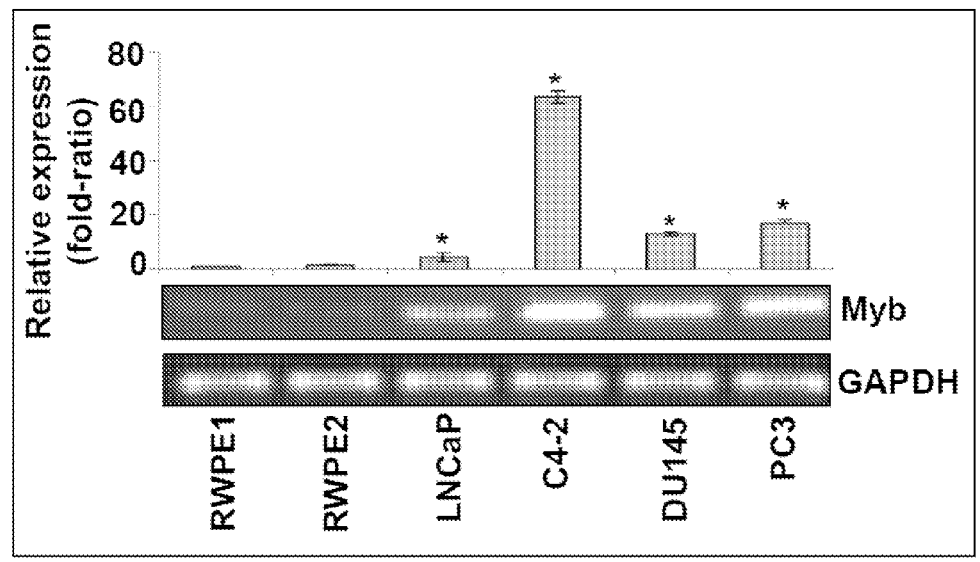
FIG. 1A, FIG. 1B, and FIG. 1C show Myb expression in normal/benign prostate epithelial and cancer cells.
Figure 1B:
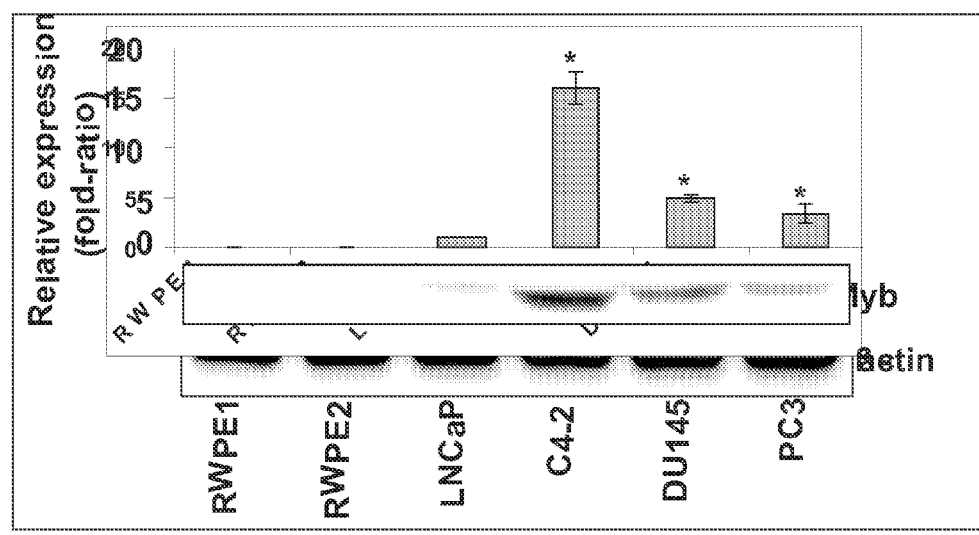
Figure 1C:
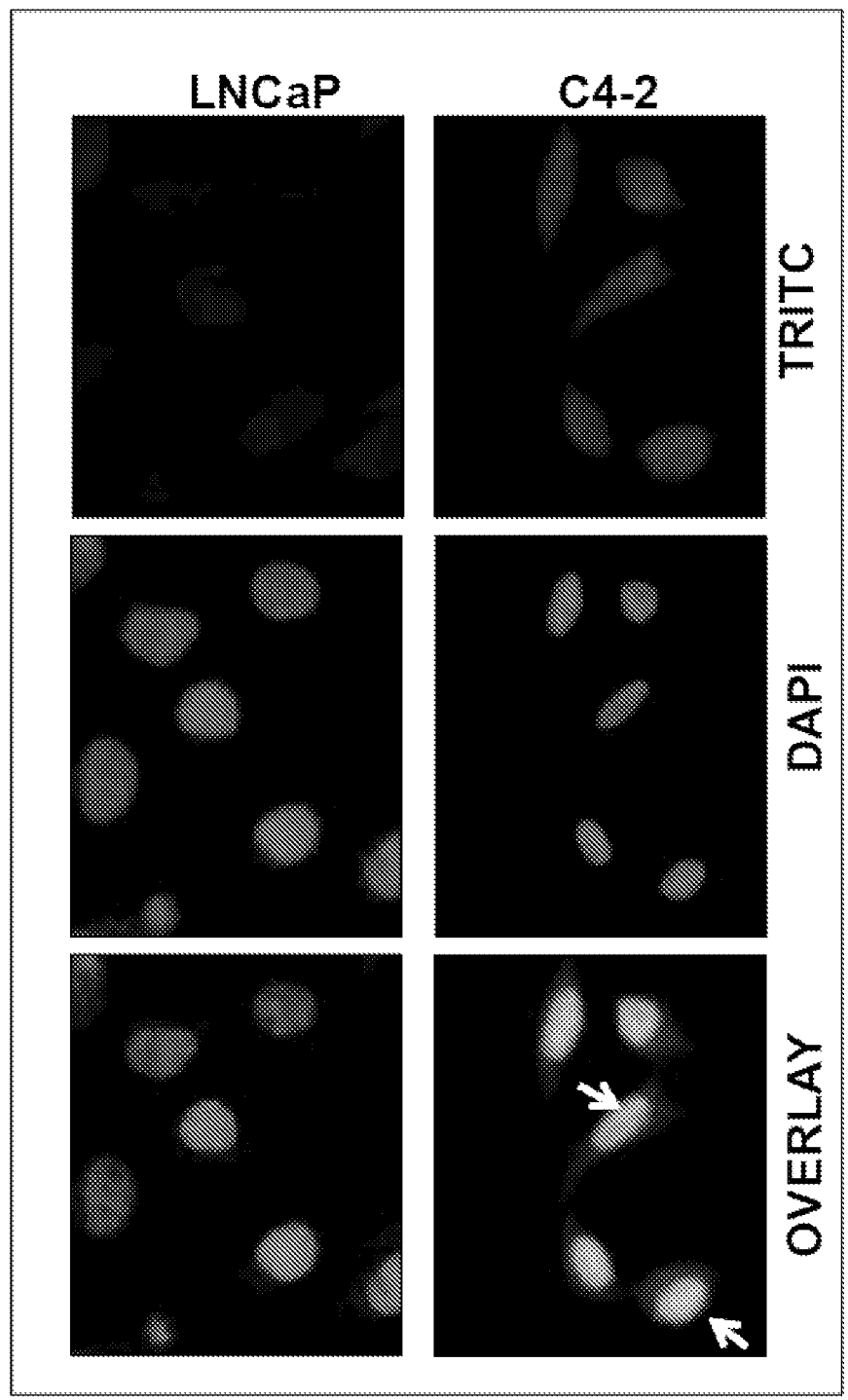

Myb is overexpressed and associated with enhanced growth and clonogenicity in prostate cancer cells. Myb is one of several genes amplified in prostate cancer, in particular, in castration-resistant prostate cancer (8). The expression of Myb in a panel of normal/benign prostate epithelial (RWPE1 and RWPE2) and cancer (LNCaP, C4-2, DU145 and PC3) cell lines was examined. The data demonstrated Myb expression in all the prostate cancer cell lines both at transcript and protein levels, while no expression or negligible expression was observed in prostate epithelial cell lines (FIG. 1A and FIG. 1B). Myb expression was significantly greater in all castration-resistant (AI: C4-2, PC3 and DU145) cells compared to androgen-dependent (AD) prostate cancer cells (AD: LNCaP). Highest level of Myb expression was observed in AI C4-2 cells, which exhibited more than 60-fold and 15-fold increase at mRNA and protein levels, respectively, compared to its parental AD LNCaP cells. In an immunofluorescence assay, an intense staining of Myb in C4-2 cells, which was predominantly localized in the nucleus with some low diffuse staining in the cytoplasm was observed (FIG. 1C).

Functional Analyses in Myb Overexpressing Cells and Myb Knockdown Cells

Figure 2A:
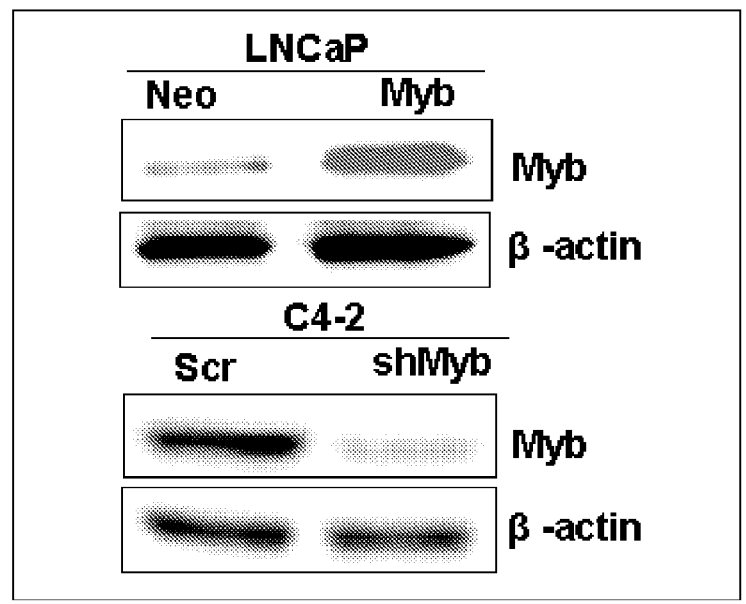
FIG. 2A, FIG. 2B, FIG. 2C, and FIG. 2D show Myb promotes growth and clonogenecity of prostate cancer cells.
Figure 2B:
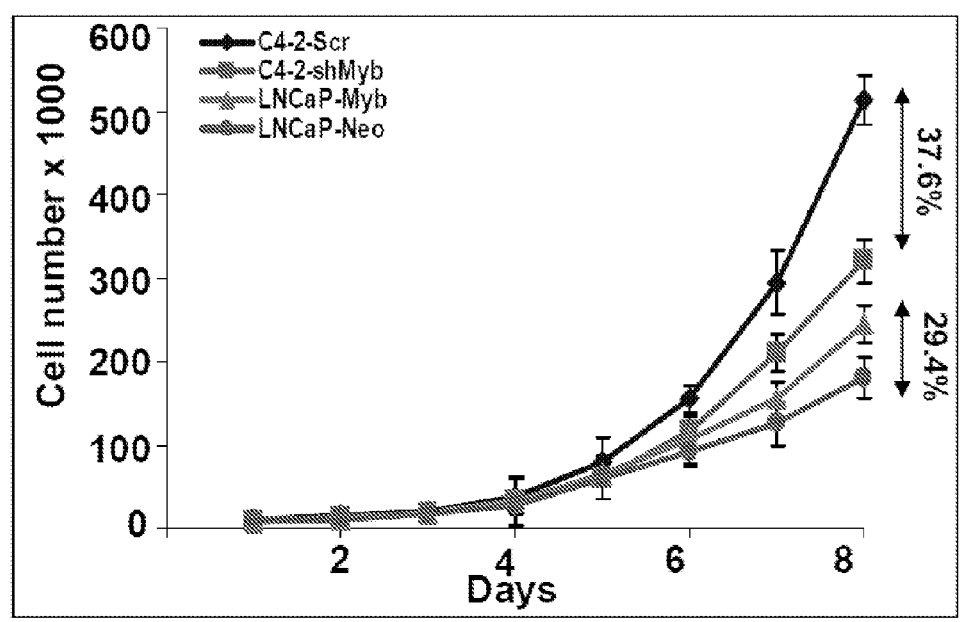
Figure 2C:
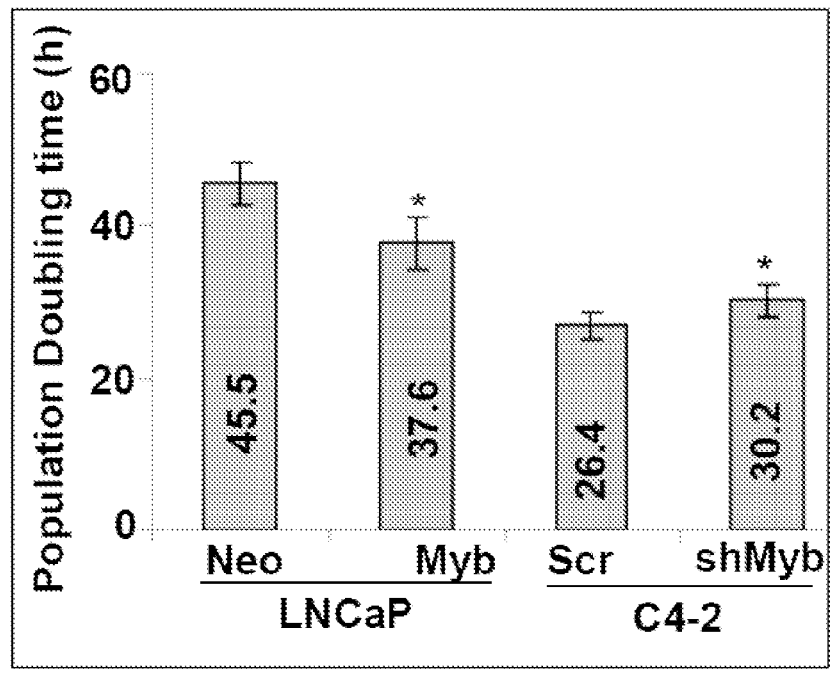
Figure 2D:
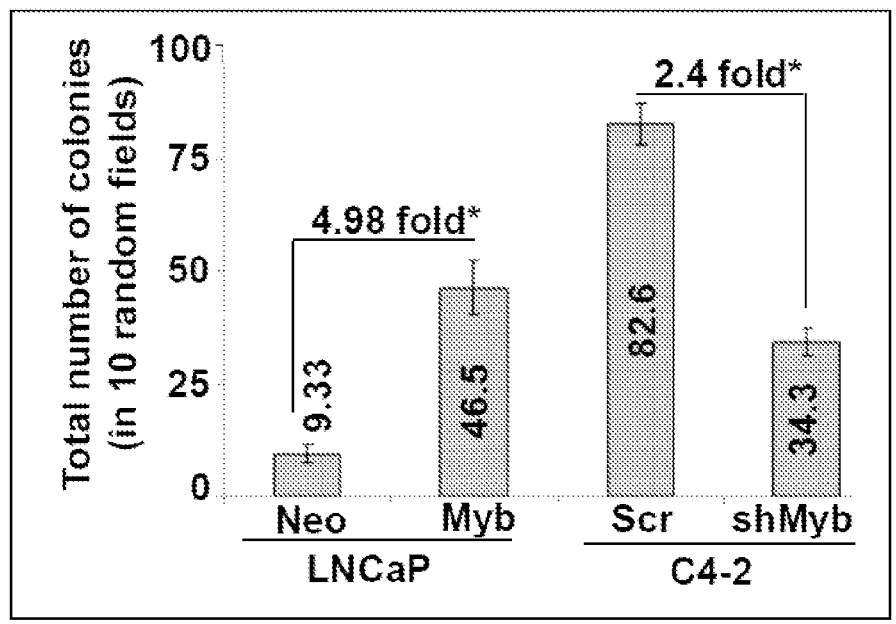

For functional analyses, Myb-overexpressing (LNCaP-Myb) or knockdown (C4-2-shMyb) sub-lines by stable transfection of LNCaP and C4-2 cells, respectively, were generated. Corresponding control transfectants (LNCaP-Neo and C4-2-Scr) were also generated and Myb overexpression or silencing was confirmed by immunoblot analysis (FIG. 2A). We next examined the effect of Myb overexpression and knockdown on growth and clonogenicity of LNCaP and C4-2 cells, respectively. Our data demonstrated that overexpression of Myb in LNCaP cells significantly enhanced their growth rate, while it decreased in Myb-silenced C4-2 cells as compared to their respective control cells (FIG. 2B). The total number of LNCaP-Myb cells on 8th day of culture indicated 29.4% increase in growth as compared to LNCaP-Neo cells, whereas 37.6% growth inhibition was observed in Myb-silenced C4-2-shMyb cells relative to C4-2-Scr cells (FIG. 2B). Growth analysis during exponential phase (96-144 h) demonstrated a decrease in population doubling time (PDT) of LNCaP-Myb (37.6 h) cells as compared to LNCaPNeo (45.5 h) cells, while C4-2-shMyb cells exhibited an increase (30.2 h) compared to C4-2-Scr (26.4 h) cells (FIG. 2C). In an anchorage-independent clonogenicity assay, LNCaP-Myb cells showed ~4.98-fold enhanced clonogenic ability as compared to LNCaP-Neo cells. In accordance with this data, clonogenicity was decreased by ~2.4-fold in C4-2-shMyb cells as compared to the C4-2-Scr cells (FIG. 2D). Altogether, our findings demonstrate a role of Myb in potentiating growth and clonogenicity of prostate cancer cells.

Plating Efficiency in Myb Overexpressing Cells and Myb Knockdown Cells

Figure 3A:
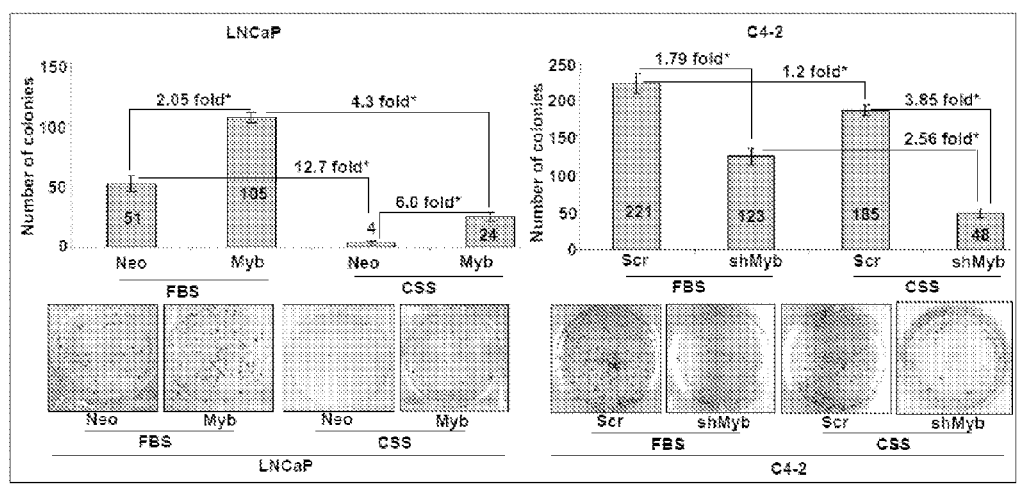
FIG. 3A and FIG. 3B show overexpression of Myb favors castration-resistant growth and upregulates PSA expression.

Overexpression of Myb supports castration-resistant growth of prostate cancer cells and upregulates prostate-specific antigen expression. Thus, the role of Myb in androgen independence was investigated. Plating efficiency is a useful indicator for long-term growth. Plating efficiency was measured in Myb overexpressing cells and Myb-knockdown cells under steroid-supplemented and steriod-reduced conditions. The data showed an increased (~2.05-fold) plating efficiency in LNCaP-Myb cells as compared to LNCaP-Neo cells under steroid-supplemented condition (FIG. 3A). Similarly, C4-2-Scr cells also exhibited greater (~1.79-fold) plating efficiency as compared to Myb-silenced C4-2 cells. Notably, when the plating efficiency was examined under steroid-deprived conditions, a >12-fold reduction was observed in LNCaP-Neo cells, whereas it only decreased to ~4.0-fold in LNCaP-Myb cells as compared to that in steroid-supplemented condition (FIG. 3A). Likewise, C4-2-Scr cells exhibited a 1.2-fold decrease under steroid-reduced condition, while it was reduced by 2.56-fold in C4-2-shMyb cells as compared to the plating efficiency in steroid supplemented condition.

Figure 3B:
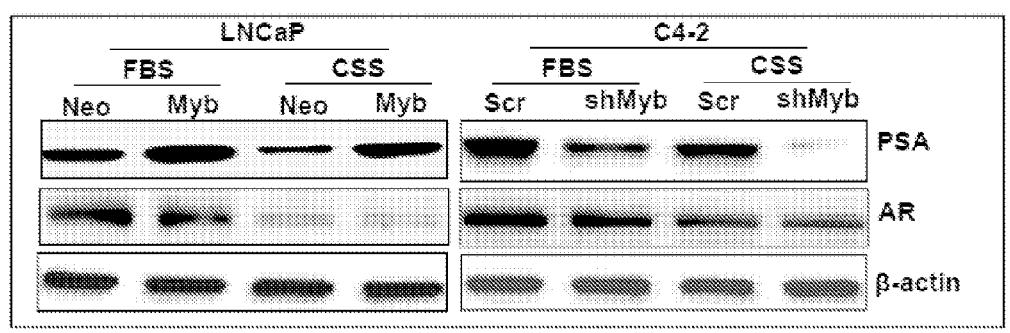

Myb-Induced Androgen-Independence and Prostate-Specific Antigen (PSA) Expression A correlation between Myb-induced androgen-independence and changes in prostate-specific antigen (PSA) expression was investigated. PSA is elevated in majority of prostate cancers and its expression is decreased (being an androgen-regulated gene) following androgen-deprivation therapy (26). However, a rebound of PSA is generally observed as the prostate cancer progress to androgen independence (27; 28). Interestingly, an elevated expression of PSA in Myb-overexpressing LNCaP cells was observed, while PSA expression was reduced in Myb-silenced C4-2 cells, compared to their respective controls (FIG. 3B). Furthermore, under steroid-reduced condition, PSA expression was considerably reduced in low Myb-expressing (LNCaP-Neo and C4-2-shMyb) cells, whereas it was fairly sustained in Myb-overexpressing (LNCaP-Myb and C4-2-Scr) prostate cancer cells. Notably, while AR expression reduced significantly upon steroid-deprivation, no change was observed in Myb-overexpressing or -silenced cells as compared to their respective controls (FIG. 3B). Altogether, the data suggest that Myb overexpression supports castration-resistant growth and is associated with elevated expression of PSA in prostate cancer cells.

Figure 4A:
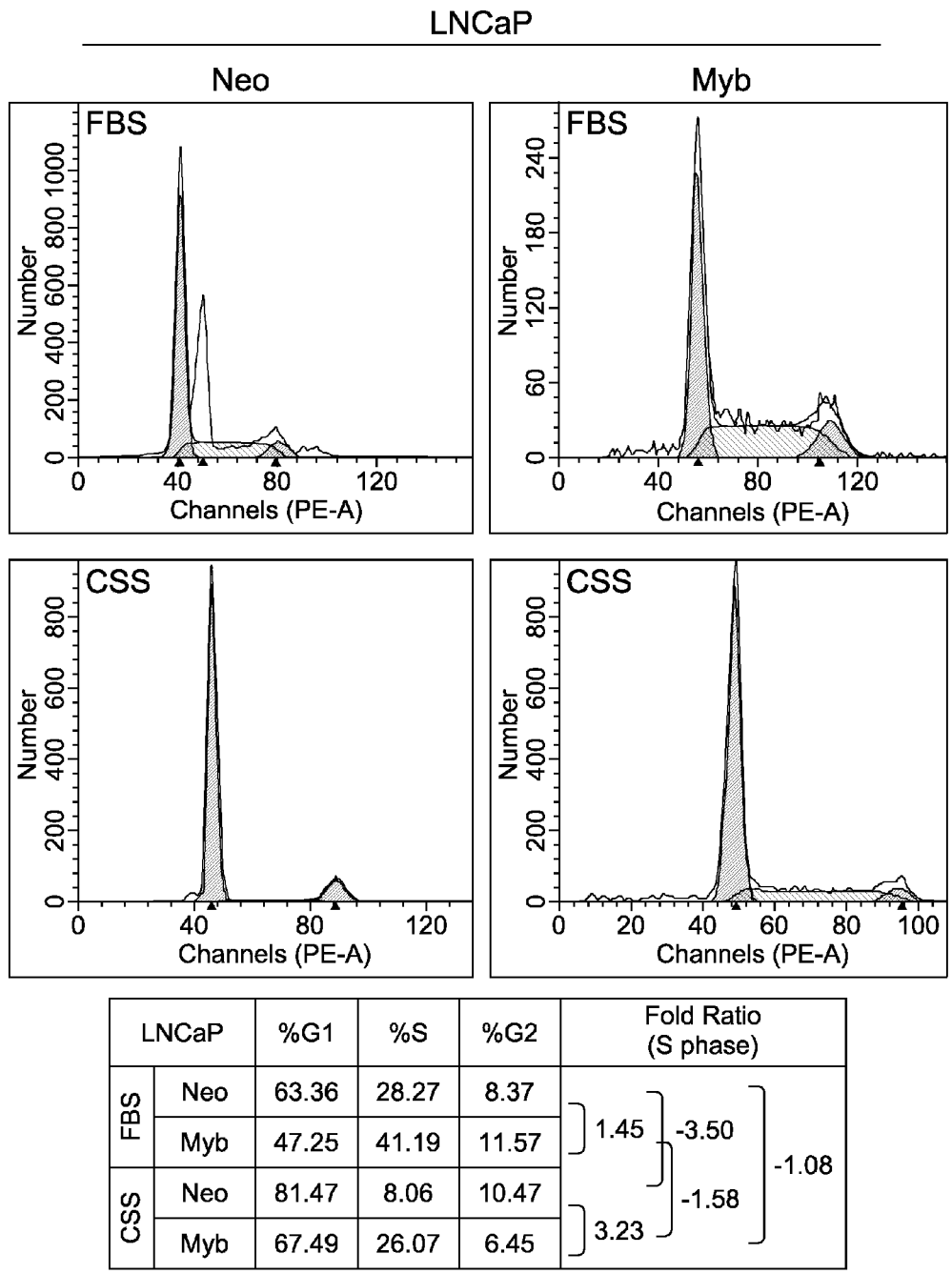
FIG. 4A and FIG. 4B show Myb overexpression facilitates cell cycle progression and prevents apoptosis.

Effects of Myb Expression on Cell Cycle Progression and Apoptosis of Prostate Cancer Cells Myb promotes cell cycle progression and confers apoptosis resistance to prostate cancer cells. Growth suppression in androgen-dependent prostate cancer cells upon androgen-ablation is associated with cell cycle arrest and induction of apoptosis, while castration-resistant cancer cells have developed mechanisms to sustain their growth under steroid-reduced condition (29). Therefore, the effect of Myb expression on cell cycle progression and apoptosis of prostate cancer cells under both steroid-supplemented and -depleted conditions was examined. The data on cell cycle showed an enhanced fraction of cells in S-phase in Myb-overexpressing (LNCaP-Myb, 41.19%; C4-2-Scr, 30.34%) cells as compared to low Myb-expressing (LNCaP-Neo, 28.27%; C4-2-shMyb, 20.63%) cells (FIG. 4A). Upon steroid-depletion, LNCaP-Neo cells exhibited a 3.5-fold decrease in the number of cells in S-phase, whereas only 1.58-fold decrease was observed in LNCaP-Myb cells. Similarly, about 1.98-fold decrease in the number of cells in S-phase was observed in low Myb-expressing C4-2-shMyb cells, while it only decreased to only 1.15-fold in C4-2-Scr cells upon steroid deprivation (FIG. 4A).

Effect of Myb on Apoptosis-Resistance of Prostate Cancer Cells

Figure 4B:
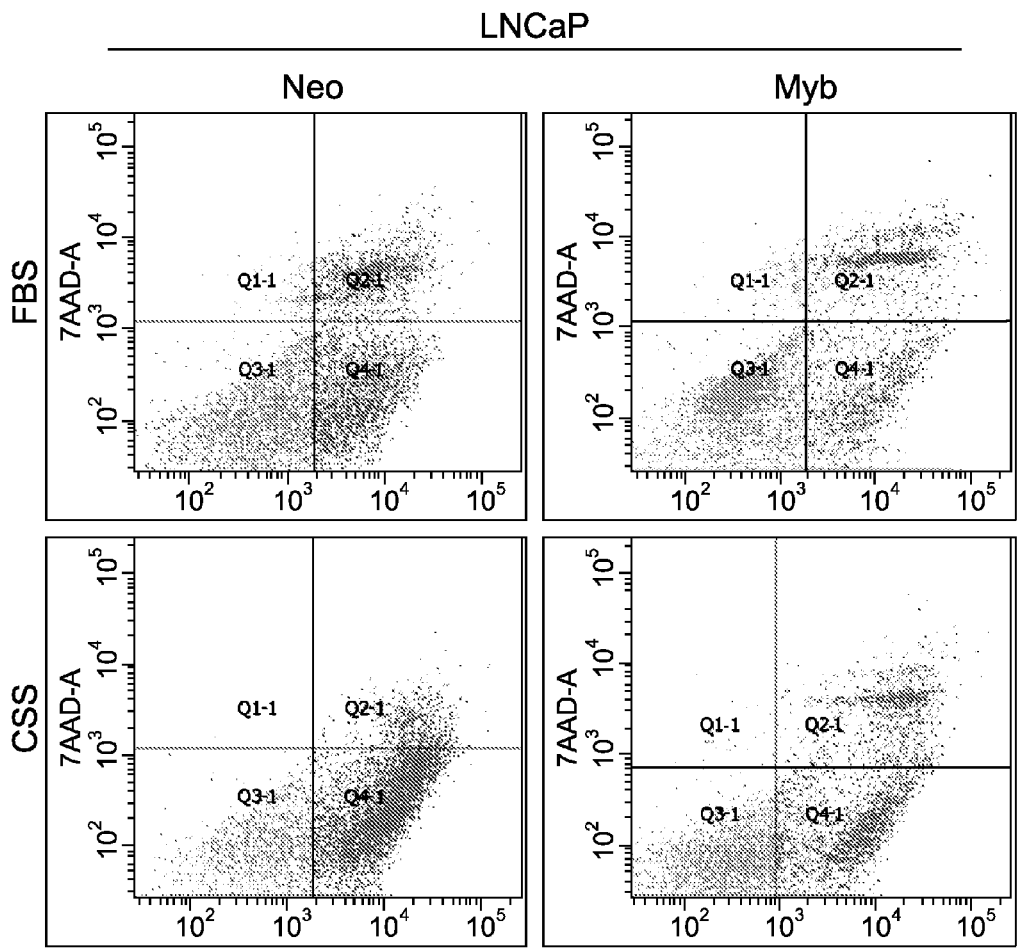

The effect of Myb on apoptosis-resistance of prostate cancer cells was examined. Sub-confluent cultures of Myb-overexpressing and knockdown cells were incubated in steroid-supplemented or steroid-reduced conditions for 96 h and the extent of apoptosis was determined by PE Annexin V and 7AAD staining followed by flow cytometry (FIG. 4B). The data showed a lower apoptotic index (Annexin V positive/7AAD negative cells) in Myb-overexpressing LNCaP-Myb (23.7%) and C4-2-Scr (9.6%) cells as compared to low Myb-expressing LNCaP-Neo (34.4%) and C4-2-shMyb (20.2%) cells, respectively. Upon steroid deprivation, apoptotic indices increased considerably in both low and high Myb-expressing cells. However, greater increases (2.03- and 2.13-folds, respectively) were observed in low Myb-expressing LNCaP-Neo and C4-2-shMyb cells as compared to Myb-overexpressing LNCaP-Myb and C4-2-Scr cells (1.36- and 1.62-folds, respectively) (FIG. 4B). Together, these findings indicate that Myb is able to suppress steroid deprivation-induced cell cycle arrest and apoptosis to support androgen independent growth of prostate cancer cells.

Effects of Altered Myb Expression on Cell Proliferation and Survival

Modulation of Myb expression alters the expression of cell cycle- and survival associated proteins. Having observed a role of Myb in cell cycle progression and resistance to apoptosis, we next examined the effect of altered Myb expression on key proteins involved in cell proliferation and survival. Our data demonstrated an induced expression of cyclins (A1, D1 and E1) upon Myb overexpression in LNCaP cells, while it was decreased upon Myb silencing in C4-2 cells under both steroid-supplemented and -reduced conditions (FIG. 5). In contrast, we observed a downregulation of p27/KIP1 (cyclin-dependent kinase inhibitor 1B) in Myb-overexpressing LNCaP, while it was upregulated in Myb-silenced C4-2 cells. Interestingly, a slight increase in the expression of another cyclin-dependent kinase inhibitor, p21/WAF1, was observed upon Myb overexpression in LNCaP cells, while it was decreased in Myb-silenced C4-2 cells. Among the survival proteins, the expression of both Bcl-xL and Bcl-2 was upregulated upon Myb overexpression in LNCaP cells, while it was downregulated in Myb knockdown C4-2 cells. A decrease in the expression of proapoptotic Bax protein in Myb-overexpressing LNCaP cells was observed; and Bax was upregulated in Myb-silenced C4-2 cells. No change, however, was observed in the expression of another pro-apoptotic protein, BAD, in either Myb-overexpressing or -silenced cells (FIG. 5).

Role of Myb in Promoting the Malignant Behavior of Prostate Cancer Cells

Myb overexpression promotes cell motility and invasion, and diminishes cell-cell interaction. As progression to androgen-independence is associated with increased aggressiveness (30), a role of Myb in promoting the malignant behavior of prostate cancer cells was investigated. First, the effect of altered Myb expression on motility and invasiveness, which are important characteristics of the aggressive cancer cells was studied. Cell motility was examined by following the migration of tumor cells under chemotactic drive in a Boyden's chamber assay. Our data showed that there was a 2.7-fold increase in the motility of LNCaP cells upon Myb overexpression, whereas a 5.0-fold decrease was observed in Myb-knockdown C4-2 cells as compared to their respective controls (FIG. 6A). For comparing the invasiveness, we monitored the capacity of Myb-overexpressing or -silenced prostate cancer cells to invade through a Matrigel-coated membrane. Similar to cell motility, we observed that LNCaP-Myb cells were more (3.2-fold) invasive as compared to the LNCaP-Neo cells, whereas C4-2-shMyb cells exhibited decreased (5.4-fold) invasiveness as compared to C4-2-Scr cells (FIG. 6B). As malignant cells tend to lose cell-cell interaction during progression towards more aggressive and metastatic phenotype, we examined the effect of Myb on prostate cancer cells in a cell aggregation assay. Our data showed a decreased cell-cell interaction in Myb-overexpressing LNCaP cells, while it was increased in Myb-silenced C4-2 cells as compared to their respective controls (FIG. 6C). Altogether, our data indicate that Myb overexpression is associated with aggressive behavior of the prostate cancer cells.

Role of Myb in EMT of Prostate Cancer Cells

Myb overexpression favors epithelial to mesenchymal transition of prostate cancer cells. Cancer cells gain mesenchymal features during their progression, a process referred to as epithelial to mesenchymal transition (EMT) (31). Mesenchymal cells are relatively more motile and exhibit less cell-cell communication; therefore, whether Myb had a role in EMT of prostate cancer cells was investigated. Considering the fact that actin-dependent membrane protrusions serve as a critical determinant of mesenchymal transition (32), actin-organization in Myb-overexpressing or Myb-knockdown prostate cancer cells was examined. Staining of filamentous-actin with FITC-conjugated phalloidin revealed the presence of many filopodial structures in Myb-overexpressing (LNCaP-Myb and C4-2-Scr) cells, while they were absent or less obvious in the low Myb-expressing (LNCaP-Neo and C4-2-shMyb) cells (FIG. 7A). Expression of a series of EMT marker proteins in Myb-overexpressing or -silenced prostate cancer cells was examined. The data demonstrated decreased expression of epithelial (E-cadherin) and increased expression of mesenchymal markers (N-cadherin, Vimentin, Slug, Snail and Twist) in Myb-overexpressing (LNCaPMyb and C4-2-Scr) cells as compared to low Myb-expressing (LNCaP-Neo and C4-2-shMyb) cells (FIG. 7B). These findings support a role of Myb in favoring EMT of prostate cancer cells.

The data described herein also demonstrate a role of Myb in potentiating malignant behavior of prostate cancer cells and favoring epithelial to mesenchymal transition. This is highly significant considering the fact that the relapsed castration-resistant cancers are also highly aggressive and more metastatic than the hormone-dependent disease (30). Myb has been shown previously to promote migration and invasion by direct or indirect mechanisms in smooth muscle and hepatocellular carcinoma cells (47; 48). Furthermore, in two recent reports, a role of Myb in inducing EMT has also been demonstrated (49; 50). In one study, it was shown that Myb acted downstream of BMP4 signaling cascade and its elevated expression cooperated with BMP4 to trigger EMT and migration of neural crest cells (50). The other study showed that Myb regulated the expression of Slug in tumor cells of different origin and altered the expression of a variety of epithelial and mesenchymal markers (49). Importantly, it was also shown that Myb-dependent Slug expression was essential for the homing of chronic myeloid leukemia K562 cells to the bone marrow (49). These observations together with our findings strongly support a role of Myb in aggressive behavior and metastasis of the cancer cells.

In summary, evidence is provided in this application for a functional role of Myb in growth, androgen-independence and malignant behavior of the prostate cancer cells. These are important observations suggesting that Myb is a marker for predicting the response to hormone therapy and should provide the impetus for future studies on prognostic and therapeutic assessments of Myb in prostate cancer.

Example 2

Effects of Myb Silencing in Castration-Resistant Prostate Cancer Cells

The expression of c-Myc and CXCR4 in castration-resistant prostate cancer cells (C4-2-SCR), and Myb-knockdown castration-resistant prostate cancer cells (C4-2 shMyb) was investigated. FIG. 8 shows that both c-Myc and CXCR4 are downregulated in Myb-knockdown castration-resistant prostate cancer cells Example 3

Myb Expression is Associated with Chemoresistance

Castration-resistant prostate cancer cells (C4-2), Myb-knockdown castration-resistant prostate cancer cells (C4-2 shMyb), androgen-dependent prostate cancer cells (LNCap-Neo), Myb-overexpressing androgen-dependent prostate cancer cells (LNCaP-Myb), were treated with increasing concentrations of Docetaxel and the viability tested at 48 hr and 72 hr post-treatment. FIG. 9 shows that in castration-resistant prostate cancer cells, decreasing expression of Myb results in an increased sensitivity to docetaxel; in androgen-dependent prostate cancer cells, increasing expression of Myb results in a decreased sensitivity to docetaxel. Table 2 summarizes the $IC_{50}$ values for docetaxel in the various cell lines.

TABLE 2

| | Docetaxel $IC_{50}$ (μM) for each cell line | | | |
|---|---|---|---|---|
| Time (hours) | C4-2 | C4-2shMyb | LNCaP-Neo | LNCaP-Myb |
| 48 | 18.2 | 7.0 | 7.6 | 20.6 |
| 72 | 13.1 | 4.8 | 4.9 | 14.8 |

Example 4

Myb is a Novel AR-Interacting Protein

Co-immunoprecipitation assays were performed using castration-resistant prostate cancer cells (C4-2), and Myb-overexpressing androgen-dependent prostate cancer cells (LNCap-Myb), with anti-Myb (rabbit monoclonal) and anti-AR (rabbit polyclonal) antibodies. FIG. 10 shows that in both C4-2 cells and LNCap-Myb cells, immunoprecipitation assays using either anti-Myb or anti-AR detect complexes containing both Myb and AR.

Example 5

Myb is Aberrantly Expressed in Pancreatic Cancer Cell Lines and Tumor Tissues

Myb expression was examiner in normal pancreas, pancreatic cancer tissues and in a panel of pancreatic cancer cell lines by immunoblot analysis. Expression of Myb was analyzed by real-time RT-PCR and Western blot, and in tissues (normal and malignant) by Western blot analysis. β-actin was used as an internal control.

An aberrant expression of Myb was observed in majority of pancreatic cancer cell lines (9 of 12, BxPC3 was weakly positive) and pancreatic cancer tissues (20 of 21), whereas no expression was observed in normal pancreas (FIG. 11A and FIG. 11B). Paraffin-embedded tissue sections on a pancreatic cancer test tissue-array were processed for Immunohistochemical staining using a Myb-specific antibody. A strong nuclear signal was detected with some diffuse cytoplasmic staining in cancer tissues, while no staining was observed in adjacent normal pancreas (FIG. 11C).

Example 6

Silencing of Myb Suppresses Pancreatic Cancer Cell Growth and Clonogenicity

Myb expression was silenced in a pancreatic cancer cell line (Panc1) through stable transfection of Myb-targeted short-hairpin RNA (shRNA) expression construct (pGFP-V-RS-shMyb). Myb-silenced cells (Panc1-shMyb) along with scrambled sequence expressing control (Panc1-Scr) were characterized for Myb silencing (FIG. 12A) and the effect of Myb knockdown on growth and clonogenicity was examined (FIG. 12B, FIG. 12C). The data demonstrated remarkable differences in the morphology of control and Myb-silenced Panc1 cells (FIG. 12B). Furthermore, Myb-silenced Panc1 cells had significantly decreased growth rate as compared to the control cells (FIG. 12C). The total number of Panc1-shMyb cells on $8^{th}$ day of culture indicated 32.86% decrease in growth as compared to Panc1-Scr (FIG. 12C). Growth analysis during exponential phase (96-144 h) demonstrated a decrease in population doubling time (PDT) of Panc1-shMyb (48.7 h) cells as compared to Panc1-Scr (57.3 h) cells (FIG. 12C).

Anchorage-dependent and -independent clonogenicity assays were performed. For anchorage-dependent clonogenicity assay, single cell suspensions were plated in 6-well plates at a density of 500 cells/well for colony formation. After two weeks, colonies were fixed with methanol, stained with crystal violet, photographed and counted using Image analysis software (Gene Tools, Syngene, Frederick, Md.) (FIG. 13A). For anchorage independent clonogenicity assay, equal volumes of agarose (1.6%) and growth medium were mixed and plated to form bottom layer in 6-well plates. Cells ($2.5 \times 10^3$ cells/mL) were suspended in regular media, mixed with equal volume of 0.6% agarose and cell suspension-agar mix (2 mL) seeded as top layer in each well. Plates were incubated under normal culture conditions for 3 weeks for colony formation. Colonies were stained with 0.005% crystal violet (Sigma-Aldrich) in PBS, observed using Nikon Eclipse microscope (Nikon Instruments Inc.), and counted in ten randomly selected fields (×100 magnification), *, p<0.05 (FIG. 13B).

In anchorage-dependent and -independent clonogenicity assays, Panc1-shMyb cells showed ~3.3- and ~3.7-folds decreased clonogenic ability, respectively, as compared to the control cells. Altogether, these findings demonstrate a role of Myb in potentiating growth and clonogenicity of pancreatic cancer cells.

Example 7

Cell Cycle Analysis of Myb-Knockdown Pancreatic Cells

Cell cycle analysis: Myb-silenced Panc1 & MiaPaCa cells along with their respective controls were synchronized by culturing them in serum-free media for 48 h, and then incubated in regular culture medium for 24 h. Subsequently, distribution of cells in different phases of cell cycle was analyzed by propidium iodide (PI) staining followed by flow cytometry (FIG. 14A). Apoptosis assay: Control and Myb-silenced Panc1 & MiaPaCa cells were assessed for apoptosis, when cultured under serum free conditions for 96 h. Percentage of apoptotic cells were analyzed by flow cytometry using PE Annexin V (FIG. 14B). The above experiment demonstrates that Myb knockdown causes cell cycle arrest and induces apoptosis in pancreatic cancer cells Myb-silenced Panc1 & MiaPaCa cells along with their respective controls were examined for the expression of various cell-cycle and survival-associated proteins. β-actin was used as an internal control (FIG. 15). Knockdown of Myb alters expression of proteins associated with cell cycle and apoptosis. In Myb knockdown Panc1 cells, the levels of at least the following proteins were reduced: cyclin A1, cyclin D1, cyclin E, and BCL-xL. In Myb knockdown MiaPaCa cells, the levels of at least the following proteins were reduced: cyclin A1, cyclin D1, cyclin E, BCL-xL, and BCL2.

Example 8

Myb Silencing Causes Down-Regulation of CXCR4, c-Myc, and SHH

The expression of CXCR4, c-Myc, and Sonic Hedgehog (SHH) was examined in control and Myb knock-down Panc1 cells. The data showed that the expression of c-Myc, CXCR4, and SHH was decreased upon silencing of Myb (FIG. 16). At least c-Myc and CXCR4 are associated with pancreatic cancer progression and metastasis, and hence, can mediate the pathogenic involvement of Myb overexpression in pancreatic cancer cells.

Example 9

Myb Downregulation Decreases Pancreatic Cancer Cell Motility, Invasion and Cell-Cell Interaction Cell motility and invasion are important attributes that define the aggressiveness of the cancer cell. The effect of Myb silencing on cell migration was examined (by transwell chamber assays) and invasion (migration through a Matrigel-coated porous membrane) (Singh A P, et al. Cancer Res 2004; 64:622-30; Chaturvedi P, et al. Mol Cancer Res 2007; 5:309-20). Cells were seeded on noncoated or Matrigel-coated membranes for motility (FIG. 17A) and invasion assays (FIG. 17B), respectively, and incubated for 16 h. Media containing 10% FBS in the lower chamber was used as a chemoattractant. Cells that had migrated or invaded through the membrane/Matrigel to the bottom of the insert were fixed, stained and counted in 10 random view fields. Bars represent the mean±S.D (n=3) of number of migrated or invaded cells per field, *, p<0.005. The data demonstrated ~2.9-fold-decrease in cell motility of Panc1-shMyb cells relative to the control cells (FIG. 17A) Likewise, we also observed ~2.6-fold reduced invasiveness in Panc1-shMyb cells (FIG. 17B).

Another behavioral property associated with tumor cells is decreased cell-cell adhesion that is required to facilitate its dissemination. The effect of Myb silencing on cell-cell interaction was examined in a hanging drop assay and observed an enhanced cell-cell aggregation in Panc1-shMyb as compared to the control cells. Drops of cell suspension (20 µl each containing 20,000 cells) of Panc1-Scr and Panc1-shMyb were placed onto the inner surface of the lid of a Petri dish. The lid was then placed on the Petri dish so that the drops were hanging from the lid with the cells suspended within them. After overnight incubation at 37° C., the lid of the Petri dish was inverted and photographed using Nikon Eclipse microscope (FIG. 17C). Myb silenced cells exhibited enhanced cell-cell interaction in both Panc1 and MiaPaCa cancer cells.

Example 10

Myb Silencing Causes Reversal of Epithelial to Mesenchymal Transition (EMT)

Cancer cells gain mesenchymal features during their progression, a process referred to as epithelial to mesenchymal transition (EMT). Mesenchymal cells are relatively more motile and exhibit less cell-cell communication; therefore, a role for Myb in EMT of pancreatic cancer cells was investigated. Considering the fact that actin-dependent membrane protrusions serve as a critical determinant of mesenchymal transition, the actin-organization in Myb-knockdown pancreatic cancer cells was examined.

Cells were grown on glass coverslips, fixed and stained with Alexa Fluor 488-conjugated phalloidin. Cells were then analyzed and photographed using fluorescent microscope. Myb-overexpressing (Panc1-Scr and MiaPaCa-Scr) cells exhibited several filopodial and lamellipodia-like projections as compared to low Myb-expressing (Panc1-shMyb and MiaPaCa-shMyb) cells (FIG. 18A). In particular, staining of filamentous-actin with FITC-conjugated phalloidin revealed the presence of many filopodial structures in the control cells, while they were absent or less obvious in Myb-silenced cells.

The expression of a series of EMT marker proteins in Myb-overexpressing or -silenced pancreatic cancer cells was examined by Western blot (FIG. 18B). The data demonstrated increased expression of epithelial (E-cadherin) and decreased expression of mesenchymal markers (N-cadherin, Vimentin, Slug, Snail and Twist) in Myb-silenced (Panc1-shMyb) cells as compared to the control (Panc1-Scr) cells. These findings support a role of Myb in favoring EMT of PC cells.

Example 11

Myb Over-Expression Promotes Growth of Pancreatic Cancer Cells

Stable Myb overexpressing (BCPC3-Myb) or control (BXPC3-Neo) were generated, and Myb expression was examined by Western blot assay. β-actin was used as an internal control (FIG. 19A). Growth of BXPC3-Myb and control BXPC3-Neo cells was monitored (by cell counting) each day for 8 days to assess their growth kinetics. BXPC3-Myb cells grew faster (population doubling time of 27.8 h) as compared to control cells (PDT of 38.7 h) with more than 49% increased growth in BXPC3 cells on 8th day (FIG. 19B). Thus, Myb over-expression promotes growth of pancreatic cancer cells Example 12

Myb Overexpression Releases Cell Cycle Arrest and Imparts Apoptosis Resistance in Pancreatic Cancer Cells Myb overexpressing BXPC3 cells along with their respective controls were synchronized by culturing them in serum-free media for 48 h, and then incubated in regular culture medium for 24 h. Subsequently, distribution of cells in different phases of cell cycle was analyzed by propidium iodide (PI) staining followed by flow cytometry (FIG. 20A). Control and Myb overexpressing BXPC3 cells were assessed for apoptosis, when cultured under serum free conditions for 96 h. Percentage of apoptotic cells were analyzed by flow cytometry using PE Annexin V (FIG. 20B). This data suggests that Myb overexpression releases cell cycle arrest and imparts apoptosis resistance in pancreatic cancer cells Example 12

Myb Overexpression Alters the Expression of Proteins Associated with Cell-Cycle and Apoptosis BXPC3-Myb and BXPC3-Neo cells were examined for the expression of various cell-cycle and survival-associated proteins (FIG. 21). In BXPC3 cells overexpressing Myb, the levels of at least the following were also increased: cyclin A1, cyclin D1, cyclin E, BCL-xL, and BCL2.

Example 14

Overexpression of Myb Enhances Motility, Invasion and Diminishes Cell-Cell Interaction In a migration and invasion assays, cells were seeded on noncoated or Matrigel-coated membranes for motility and invasion assays, respectively, and incubated for 16 h. Media containing 10% FBS in the lower chamber was used as a chemoattractant. Cells that had migrated or invaded through the membrane/Matrigel to the bottom of the insert were fixed, stained and counted in 10 random view fields. Bars represent the mean±S.D (n=3) of number of migrated or invaded cells per field, *, p<0.005. (FIG. 22A). In a cell-cell interaction assay the effect on cell-cell interaction was determined by hanging drop assay. Overexpression of Myb was associated with diminished cell-cell interaction in BXPC3 cells (FIG. 22B). Thus, overexpression of Myb enhances motility, invasion and diminishes cell-cell interaction.

Example 15

Overexpression of Myb Facilitates Epithelial to Mesenchymal Transition (EMT)

Expression profiles of various epithelial (E-cadherin) and mesenchymal markers (N-cadherin, Vimentin, Slug, Snail and Twist) were examined in BXPC3-Myb and BXPC3-Neo cells by western blot analyses (FIG. 23). In BXPC3 cells overexpressing Myb, the levels of at least the following were also increased: N-cadherin, vimentin, twist, slug, and snail. Thus, Myb overexpression was associated with gain of mesenchymal and loss of epithelial markers, indicating its role in EMT Example 16

Identification of Myb Target Genes

To map the regulatory regions across the genome and identify the true endogenous targets of Myb, unbiased ChIP-on-Chip assays are performed. GeneChip human promoter 1.0R array (Affymetrix) is used and standard procedures are followed (31). Briefly, Myb-overexpressing (endogenous and ectopic) pancreatic cancer cells are subjected to chromatin immunoprecipitation (ChIP) using anti-Myb antibody, and co-immunoprecipitated DNA is purified and amplified using a random primed PCR. Subsequently amplified DNA is fragmented enzymatically (by combined treatment of uracyl DNA glycosilase, UDG and apurinic or apyrimidinic endonuclease 1, APE1), labeled using GeneChip WT double-stranded DNA terminal labeling kit (Affymetrix) and hybridized using GeneChip hybridization, wash and stain kit. Next, whole-genome microarray analysis is performed using total RNA isolated from control and Myb-silenced/-overexpressing PC cells. This analysis identifies targets included in the Myb-regulated transcriptome. Differentially-expressed genes are subjected to pathway analysis as previously described (32) and candidate genes are further validated by quantitative RT-PCR. Through the above analyses, the precise targets and molecular pathways putatively involved in Myb-mediated cell growth and tumor formation are determined.

Example 17

In Vivo Tumorigenicity and Metastasis Analysis

The effect of Myb expression on PC cell tumorigenicity and metastasis is studied in athymic mice by orthotopic (OT) implantation of paired luciferase-tagged Myb-overexpressing and knockdown PC cell lines (11). There are six groups of cell lines (Panc1-Scr, Panc1-shMyb, MiaPaCa-Scr, MiaPaCa-shMyb, BxPC3-Neo, and BxPC3-Myb) and ten mice are used in each group (total 60 mice=10×6). This sample size provides 72% power to detect a difference of at least 1 standard deviation between group means based on a 2-tailed test with a type I error level of 0.05. In vivo optical imaging utilizes bioluminescence measurement for about 20 min after i.p. injection of 3 mg n-Luciferin into each animal using a Xenogen-IVIS-cooled CCD optical system (IVIS-Spectrum). In addition, tumor growth is assessed by the weighing and palpation of each animal on alternate days. All mice are sacrificed depending upon the tumor load (not more than 10% of the body weight at the time of tumor injection), and no later than 10 weeks after a final bioluminescence measurement. The presence of metastatic lesions in different organs is determined in sacrificed animals. Tumors are excised, weighed, and measured for their dimensions and preserved in formalin for histology. Proliferation and apoptosis indices are determined by IHC on orthotopically developed PC tissues using anti-proliferating cell nuclear antigen (PCNA) or rabbit polyclonal Ki67 antibodies, and terminal deoxyribonucleotidyl transferase-mediated dUTP nick end labeling (TUNEL) assays (33, 34).

The following references are incorporated herein by reference in their entireties.

REFERENCES (1) Jemal A, Siegel R, Xu J, Ward E. Cancer statistics, 2010. CA Cancer J Clin 2010; 60:277-300.
(2) Feldman B J, Feldman D. The development of androgen-independent prostate cancer. Nat Rev Cancer 2001; 1:34-45.
(3) Attard G, Swennenhuis J F, Olmos D, et al. Characterization of ERG, AR and PTEN gene status in circulating tumor cells from patients with castration-resistant prostate cancer. Cancer Res 2009; 69:2912-8.
(4) Chen T, Wang L H, Farrar W L. Interleukin 6 activates androgen receptormediated gene expression through a signal transducer and activator of transcription 3-dependent pathway in LNCaP prostate cancer cells. Cancer Res 2000; 60:2132-5.
(5) Culig Z, Hobisch A, Cronauer M V, et al. Mutant androgen receptor detected in an advanced-stage prostatic carcinoma is activated by adrenal androgens and progesterone. Mol Endocrinol 1993; 7:1541-50.
(6) Hobisch A, Eder I E, Putz T, et al. Interleukin-6 regulates prostate-specific protein expression in prostate carcinoma cells by activation of the androgen receptor. Cancer Res 1998; 58:4640-5.
(7) Schroder F H. Progress in understanding androgen-independent prostate cancer (AIPC): a review of potential endocrine-mediated mechanisms. Eur Urol 2008; 53:1129-37.
(8) Edwards J, Krishna N S, Witton C J, Bartlett J M. Gene amplifications associated with the development of hormone-resistant prostate cancer. Clin Cancer Res 2003; 9:5271-81.
(9) Ramsay R G, Gonda T J. MYB function in normal and cancer cells. Nat Rev Cancer 2008; 8:523-34.
(10) Kanei-Ishii C, Yasukawa T, Morimoto R I, Ishii S. c-Myb-induced trans-activation mediated by heat shock elements without sequence-specific DNA binding of c-Myb. J Biol Chem 1994; 269:15768-75.
(11) Gonda T J, Metcalf D. Expression of myb, myc and fos proto-oncogenes during the differentiation of a murine myeloid leukaemia. Nature 1984; 19-25; 310:249-51.
(12) Kauraniemi P, Hedenfalk I, Persson K, et al. MYB oncogene amplification in hereditary BRCA1 breast cancer. Cancer Res 2000; 60:5323-8.
(13) Melani C, Rivoltini L, Parmiani G, Calabretta B, Colombo M P. Inhibition of proliferation by c-myb antisense oligodeoxynucleotides in colon adenocarcinoma cell lines that express c-myb. Cancer Res 1991; 51:2897-901. (14) Park J G, Reddy E P. Large-scale molecular mapping of human c-myb locus: cmyb proto-oncogene is not involved in 6q-abnormalities of lymphoid tumors. Oncogene 1992; 7:1603-9.
(15) Torelli G, Venturelli D, Colo A, et al. Expression of c-myb protooncogene and other cell cycle-related genes in normal and neoplastic human colonic mucosa. Cancer Res 1987; 47:5266-9.
(16) Zorbas M, Sicurella C, Bertoncello I, et al. c-Myb is critical for murine colon development. Oncogene 1999; 18:5821-30.
(17) Mucenski M L, McLain K, Kier A B, et al. A functional c-myb gene is required for normal murine fetal hepatic hematopoiesis. Cell 1991; 65:677-89.
(18) Hess J L, Bittner C B, Zeisig D T, et al. c-Myb is an essential downstream target for homeobox-mediated transformation of hematopoietic cells. Blood 2006; 108:297-304.
(19) Calabretta B, Sims R B, Valtieri M, et al. Normal and leukemic hematopoietic cells manifest differential sensitivity to inhibitory effects of c-myb antisense oligodeoxynucleotides: an in vitro study relevant to bone marrow purging. Proc Natl Acad Sci USA 1991; 88:2351-5.
(20) Lidonnici M R, Corradini F, Waldron T, Bender T P, Calabretta B. Requirement of c-Myb for p210 (BCR/ABL)-dependent transformation of hematopoietic progenitors and leukemogenesis. Blood 2008; 111:4771-9.
(21) Hijiya N, Zhang J, Ratajczak M Z, et al. Biologic and therapeutic significance of MYB expression in human melanoma. Proc Natl Acad Sci USA 1994; 91:4499-503.
(22) Persson M, Andren Y, Mark J, et al. Recurrent fusion of MYB and NFIB transcription factor genes in carcinomas of the breast and head and neck. Proc Natl Acad Sci USA 2009; 106:18740-4.
(23) Thompson M A, Rosenthal M A, Ellis S L, et al. c-Myb down-regulation is associated with human colon cell differentiation, apoptosis, and decreased Bcl-2 expression. Cancer Res 1998; 58:5168-75. (24) Singh S, Srivastava S K, Bhardwaj A, Owen L B, Singh A P. CXCL12-CXCR4 signalling axis confers gemcitabine resistance to pancreatic cancer cells: a novel target for therapy. Br J Cancer 2010; 103:1671-9.
(25) Singh A P, Moniaux N, Chauhan S C, Meza J L, Batra S K. Inhibition of MUC4 expression suppresses pancreatic tumor cell growth and metastasis. Cancer Res 2004; 64:622-30.
(26) Stamey T A, Kabalin J N, Ferrari M, Yang N. Prostate specific antigen in the diagnosis and treatment of adenocarcinoma of the prostate. IV. Anti-androgen treated patients. J Urol 1989; 141:1088-90.
(27) Cheng H, Snoek R, Ghaidi F, Cox M E, Rennie P S. Short hairpin RNA knockdown of the androgen receptor attenuates ligand-independent activation and delays tumor progression. Cancer Res 2006; 66:10613-20.
(28) Ellis W J, Vessella R L, Buhler K R, et al. Characterization of a novel androgensensitive, prostate-specific antigen-producing prostatic carcinoma xenograft: LuCaP 23. Clin Cancer Res 1996; 2:1039-48.
(29) Bhardwaj A, Singh S, Srivastava S K, et al. Modulation of protein phosphatase 2A (PP2A) activity alters androgen-independent growth of prostate cancer cells: therapeutic implications. Mol Cancer Ther 2011.
(30) Jennbacken K, Gustaysson H, Welen K, Vallbo C, Damber J E. Prostate cancer progression into androgen independency is associated with alterations in cell adhesion and invasivity. Prostate 2006; 66:1631-40.
(31) Singh A, Settleman J. EMT, cancer stem cells and drug resistance: an emerging axis of evil in the war on cancer. Oncogene 2010; 29:4741-51.
(32) Shankar J, Messenberg A, Chan J, et al. Pseudopodial actin dynamics control epithelial-mesenchymal transition in metastatic cancer cells. Cancer Res 2010; 70:3780-90.
(33) Locke J A, Guns E S, Lubik A A, et al. Androgen levels increase by intratumoral de novo steroidogenesis during progression of castration-resistant prostate cancer. Cancer Res 2008; 68:6407-15. (34) Sun D, Lee Y S, Malhotra A, et al. miR-99 family of MicroRNAs suppresses the expression of prostate-specific antigen and prostate cancer cell proliferation. Cancer Res 2011; 71:1313-24.

(35) Yeung F, Li X, Ellett J, et al. Regions of prostate-specific antigen (PSA) promoter confer androgen-independent expression of PSA in prostate cancer cells. J Biol Chem 2000; 275:40846-55.

(36) Hernandez-Munain C, Krangel M S. c-Myb and core-binding factor/PEBP2 display functional synergy but bind independently to adjacent sites in the T-cell receptor delta enhancer. Mol Cell Biol 1995; 15:3090-9.

(37) Oelgeschlager M, Nuchprayoon I, Luscher B, Friedman A D. C/EBP, c-Myb, and PU.1 cooperate to regulate the neutrophil elastase promoter. Mol Cell Biol 1996; 16:4717-25.

(38) Shapiro L H. Myb and Ets proteins cooperate to transactivate an early myeloid gene. J Biol Chem 1995; 270:8763-71.

(39) Knudsen K E, Arden K C, Cavenee W K. Multiple G1 regulatory elements control the androgen-dependent proliferation of prostatic carcinoma cells. J Biol Chem 1998; 273:20213-22.

(40) Eto M, Bennouna J, Hunter O C, et al. C16 ceramide accumulates following androgen ablation in LNCaP prostate cancer cells. Prostate 2003; 57:66-79.

(41) Muller C, Yang R, Idos G, et al. c-myb transactivates the human cyclin A1 promoter and induces cyclin A1 gene expression. Blood 1999; 94:4255-62.

(42) Malaterre J, Carpinelli M, Ernst M, et al. c-Myb is required for progenitor cell homeostasis in colonic crypts. Proc Natl Acad Sci USA 2007; 104:3829-34.

(43) Biroccio A, Benassi B, D'Agnano I, et al. c-Myb and Bcl-x overexpression predicts poor prognosis in colorectal cancer: clinical and experimental findings. Am J Pathol 2001; 158:1289-99.

(44) Yuan J, Crittenden R B, Bender T P. c-Myb promotes the survival of CD4+CD8+ double-positive thymocytes through upregulation of Bcl-xL. J Immunol 2010; 184:2793-804.

(45) Salomoni P, Perrotti D, Martinez R, Franceschi C, Calabretta B. Resistance to apoptosis in CTLL-2 cells constitutively expressing c-Myb is associated with induction of BCL-2 expression and Myb-dependent regulation of bcl-2 promoter activity. Proc Natl Acad Sci USA 1997; 94:3296-301.

(46) Wilkins H R, Doucet K, Duke V, Morra A, Johnson N. Estrogen prevents sustained COLO-205 human colon cancer cell growth by inducing apoptosis, decreasing c-myb protein, and decreasing transcription of the anti-apoptotic protein bcl-2. Tumour Biol 2010; 31:16-22.

(47) Pitsch R J, Goodman G R, Minion D J, et al. Inhibition of smooth muscle cell proliferation and migration in vitro by antisense oligonucleotide to c-myb. J Vasc Surg 1996; 23:783-91.

(48) Chen R X, Xia Y H, Xue T C, Ye S L. Transcription factor c-Myb promotes the invasion of hepatocellular carcinoma cells via increasing osteopontin expression. J Exp Clin Cancer Res 2010; 29:172:172.

(49) Tanno B, Sesti F, Cesi V, et al. Expression of Slug is regulated by c-Myb and is required for invasion and bone marrow homing of cancer cells of different origin. J Biol Chem 2010; 285:29434-45. (50) Karafiat V, Dvorakova M, Krejci E, et al. Transcription factor c-Myb is involved in the regulation of the epithelial-mesenchymal transition in the avian neural crest. Cell Mol Life Sci 2005; 62:2516-25.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A method for increasing the sensitivity of a neoplastic cell to a chemotherapeutic agent comprising:
   reducing the expression level of a nucleic acid encoding c-Myb or the expression level of c-Myb protein in the cell or reducing activity of c-Myb protein by contacting the cell with a sufficient amount of an isolated nucleic acid to increase the sensitivity of said cell to said chemotherapeutic agent, wherein said isolated nucleic acid comprises at least 16 consecutive nucleotides having a sequence that is at least 90% identical to a sequence encoding c-Myb or complement thereof, wherein said isolated nucleic acid is selected from a small hairpin RNA (shRNA), a small interfering RNA (siRNA), a micro RNA (miRNA), an antisense polynucleotide, and a ribozyme, wherein the cell is selected from the group consisting of a prostate cancer cell, a castration-resistant prostate cancer cell, and an androgen-dependent prostate cancer cell; and
   contacting the cell with an effective amount of the chemotherapeutic agent, wherein the effective amount is sufficient to inhibit the growth of the cell, wherein the effective amount is reduced compared to the effective amount for a cell wherein the level of a nucleic acid encoding c-Myb or a fragment thereof or the level of c-Myb protein or a fragment thereof or the activity of c-Myb protein is not reduced.

2. The method of claim 1, wherein the isolated nucleic acid comprises a sequence selected from the group consisting of a sequence encoding antisense c-Myb or a fragment thereof, an antisense nucleic acid complementary to a sequence encoding c-Myb or a fragment thereof, and a sequence comprising SEQ ID NO:06.

3. The method of claim 1, wherein the chemotherapeutic agent is selected from the group consisting of docetaxel, and paclitaxel.

4. A method for increasing the sensitivity of a neoplastic cell to a chemotherapeutic agent comprising reducing the expression level of a nucleic acid encoding c-Myb or the expression level of c-Myb protein in the cell or reducing activity of c-Myb protein by contacting the cell with a sufficient amount of an isolated nucleic acid to increase the sensitivity of said cell to said chemotherapeutic agent, wherein said isolated nucleic acid comprises SEQ ID NO:06.

5. The method of claim 4, wherein the neoplastic cell is selected from the group consisting of a prostate cancer cell, a castration-resistant prostate cancer cell, and an androgen-dependent prostate cancer cell.

6. The method of claim 4, further comprising contacting the cell with a chemotherapeutic agent.

7. The method of claim 6, further comprising contacting the cell with an effective amount of the chemotherapeutic agent, wherein the effective amount is sufficient to inhibit the growth of the cell, wherein the effective amount is reduced compared to a cell wherein the level of a nucleic acid encoding c-Myb or a fragment thereof or the level of c-Myb protein or a fragment thereof or the activity of c-Myb protein is not reduced.

8. The method of claim 4, wherein the chemotherapeutic agent is selected from the group consisting of docetaxel, and paclitaxel.

9. The method of claim 1, wherein the isolated nucleic acid is selected from the group consisting of an siRNA and an shRNA.

10. The method of claim 1, wherein the neoplastic cell is a prostate cancer cell.

11. The method of claim 1, wherein the neoplastic cell is a castration-resistant prostate cancer cell.

12. The method of claim 1, wherein the neoplastic cell is an androgen-dependent prostate cancer cell.

13. The method of claim 1, wherein the chemotherapeutic agent is docetaxel.

14. The method of claim 1, wherein the chemotherapeutic agent is paclitaxel.

15. The method of claim 1, wherein the isolated nucleic acid comprises SEQ ID:06.

16. The method of claim 4, wherein the expression level of a nucleic acid encoding c-Myb is reduced.

17. The method of claim 4, wherein the expression level of c-Myb protein in the cell is reduced.

18. The method of claim 4, wherein the activity of c-Myb protein is reduced.

19. The method of claim 4, wherein the neoplastic cell is a prostate cancer cell.

20. The method of claim 4, wherein the neoplastic cell is a castration-resistant prostate cancer cell.

21. The method of claim 4, wherein the neoplastic cell is an androgen-dependent prostate cancer cell.

22. The method of claim 4, wherein the chemotherapeutic agent is docetaxel.

23. The method of claim 4, wherein the chemotherapeutic agent is paclitaxel.

24. The method of claim 6, wherein the chemotherapeutic agent is docetaxel.

25. The method of claim 6, wherein the chemotherapeutic agent is paclitaxel.

* * * * *

UNITED STATES PATENT AND TRADEMARK OFFICE
CERTIFICATE OF CORRECTION

| | |
|---|---|
| PATENT NO. | : 9,458,456 B2 |
| APPLICATION NO. | : 14/007938 |
| DATED | : October 4, 2016 |
| INVENTOR(S) | : Ajay Pratap Singh et al. |

It is certified that error appears in the above-identified patent and that said Letters Patent is hereby corrected as shown below:

On the Title Page

In Column 2 (page 2, item (56)) at Line 35, Under Other Publications, change "discruption" to --disruption--.

In the Specification

In Column 1 at Line 17 (approx.), Change "RESISITANCE" to --RESISTANCE--.

In Column 1 at Line 26 (approx.), Change "NIH/NCl." to --NIH/NCI.--.

In Column 4 at Line 57, Change "motily" to --motility--.

In Column 11 at Line 59, Change "clonogenecity" to --clonogenicity--.

In Column 12 at Line 5, Change "sh-Myb" to --shMyb--.

In Column 12 at Line 20, Change "steroidsupplemented" to --steroid supplemented--.

In Column 13 at Line 49, Change "Mybexpressing" to --Myb-expressing--.

In Column 22 at Line 58, Change "quantative" to --quantitative--.

In Column 37 at Line 2, Change "(Invtrogen)." to --(Invitrogen).--.

In Column 37 at Line 3, Change "(Gelantis" to --(Galantis--.

In Column 38 at Line 64, Change "steroidsupplemented" to --steroid supplemented--.

Signed and Sealed this
Fourteenth Day of February, 2017

Michelle K. Lee
*Director of the United States Patent and Trademark Office*

CERTIFICATE OF CORRECTION (continued)
U.S. Pat. No. 9,458,456 B2

In Column 39 at Line 3, Change "teraphthalate" to --terephthalate--.

In Column 40 at Line 21, Change "steriod-reduced" to --steroid-reduced--.

In Column 43 at Line 32 (approx.), After "cells" insert --.--.

In Column 45 at Line 29 (approx.), After "cells" insert --.--.

In Column 47 at Line 9 (approx.), After "cells'" insert --.--.

In Column 47 at Line 27 (approx.), After "cells" insert --.--.

In Column 47 at Line 29 (approx.), Change "12" to --13--.

In Column 48 at Line 7 (approx.), After "EMT" insert --.--.

In Column 48 at Line 24, Change "glycosilase," to --glycosylase,--.

In Column 49 at Lines 54-57, Delete "(14) Park J G. Reddy E P. Large-scale molecular mapping of human c-myb locus: cmyb proto-oncogene is not involved in 6q-abnormalities of lymphoid tumors. Oncogene 1992; 7:1603-9." and insert the same on Column 49, Line 55, as a new paragraph.

In Column 50 at Lines 25-29 (approx.), Delete "(24) Singh S, Srivastava S K, Bhardwaj A, Owen L B, Singh A P. CXCL12-CXCR4 signalling axis confers gemcitabine resistance to pancreatic cancer cells: a novel target for therapy. Br J Cancer 2010; 103:1671-9." and insert the same on Column 50, Line 26 (approx.), as a new paragraph.

In Column 50 at Lines 64-67, Delete "(34) Sun D, Lee Y S, Malhotra A, et al. miR-99 family of MicroRNAs suppresses the expression of prostate-specific antigen and prostate cancer cell proliferation. Cancer Res 2011;71:1313-24." and insert the same on Column 50, Line 65, as a new paragraph.

In Column 52 at Lines 8-12 (approx.), Delete "(34) Sun D, Lee Y S, Malhotra A, et al. miR-99 family of MicroRNAs suppresses the expression of prostate-specific antigen and prostate cancer cell proliferation. Cancer Res 2011;71:1313-24." and insert the same on Column 52, Line 9 (approx.), as a new paragraph.